US008224579B2

(12) United States Patent
Gobezie et al.

(10) Patent No.: US 8,224,579 B2
(45) Date of Patent: Jul. 17, 2012

(54) METHOD OF DIAGNOSING OSTEOARTHRITIS

(75) Inventors: Reuben Gobezie, Cleveland Heights, OH (US); David M. Lee, Needham, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 1378 days.

(21) Appl. No.: 11/638,254

(22) Filed: Dec. 13, 2006

(65) Prior Publication Data

US 2007/0207480 A1  Sep. 6, 2007

Related U.S. Application Data

(63) Continuation-in-part of application No. PCT/US2006/23619, filed on Jun. 16, 2006.

(60) Provisional application No. 60/692,040, filed on Jun. 17, 2005.

(51) Int. Cl.
*G01N 33/48* (2006.01)
*C12Q 1/68* (2006.01)
*G06F 7/60* (2006.01)
*G06G 7/58* (2006.01)

(52) U.S. Cl. ............... 702/19; 435/6; 702/20; 703/2; 703/11

(58) Field of Classification Search .................. None
See application file for complete search history.

(56) References Cited

U.S. PATENT DOCUMENTS

| 2002/0119452 A1 | 8/2002 | Phippard et al. ............ 435/6 |
| 2003/0224979 A1 | 12/2003 | Kuberasampath et al. ....... 514/2 |
| 2004/0209275 A1 | 10/2004 | Liew et al. ............ 435/6 |
| 2007/0207480 A1 | 9/2007 | Gobezie et al. |

FOREIGN PATENT DOCUMENTS

| WO | WO-9409155 | 4/1994 |
| WO | WO 02/070737 | 9/2002 |
| WO | WO 2004/092413 | 10/2004 |
| WO | WO-2006138646 | 12/2006 |

OTHER PUBLICATIONS

Danesh et al., JAMA, vol. 279, pp. 1477-1482, 1998.*
Hasenclever et al., The New England Journal of Medicine, vol. 339, p. 1506, 1998.*
Gerard HC, et al. "Frequency of apolipoprotein E allele types in patients with Chlamydia-associated arthritis and other arthritides." *Microbial Pathogenesis* (1999) 26:1 p. 35-43.
Gobezie et al. "Highly sensitive and specific synovial fluid protein biomarkers for osteoarthritis identified using proteomic analysis." Database Biosis; Biosciences Information Service (2006) Database accession No. XP002472065.
Gobezie et al. "High abundance synovial fluid proteome: disctint profiles in health and osteoarthritis." *Arthritis Research and Therapy* (2007) 9:2 p. R36.

International Search Report for PCT/US06/23619 (Mar. 1, 2007).
International Search Report for PCT/US07/87543 (Oct. 16, 2008).
Kan CC et al. "Nucleotide sequence of cDNA encoding human alpha2-macroglobulin and assignment of the chromosomal locus." *PNAS* (1985) 82:8 p. 2282-2286.
RDI Division of Fitzgeral Industries "Antibodies: Alpha 2-macroglobulin polyclonal antibodies." (2005) p. 1-2 http://www.researchd.com/miscabs/a2macro.htm>.
Written Opinion for PCT/US06/23619 (Mar. 1, 2007).
Written Opinion for PCT/US07/87543 (Oct. 16, 2008).
Zhang et al. "Microarray analysis reveals the involvement of beta-2 microglobulin in human osteoarthritis." *Osteoarthritis and Cartilage* (2002) 10:12 p. 950-960.
Bhoola et al., "Kinins—key mediators in inflammatory arthritis?", *Br. J. Rheumatol.*, 1992, 31: 509-518.
Bond et al., "Generation of kinins in synovial fluid from patients with arthropathy", *Immunopharmacology*, 1997, 36: 209-216.
Breitner et al., "Complement components C1q, C1r/C1s, and C1INH in rheumatoid arthritis. Correlation of in situ hybridization and northern blot results with function and protein concentration in synovium and primary cell cultures", *Arthritis Rheum.*, 1995, 38: 492-498.
Campion et al., "Levels of keratan sulfate in the serum and synovial fluid of patients with osteoarthritis of the knee", *Arthritis Rheum.*, 1991, 34: 1254-1259.
Carlson et al, "Synovial fluid biomarker levels predict articular cartilage damage following complete medial meniscectomy in the canine knee", *J. Orthop. Res.*, 2002, 20: 92-100.
Christgau et al., "Collagen type II C-telopeptide fragments as an index of cartilage degradation", *Bone*, 2001, 29: 209-215.
Collard et al., "Complement activation following oxidative stress", *Mol. Immunol.*, 1999, 36: 941-948.
Collins et al., "Regulation of early complement components C3 and C4 in the synovium", Clin. Diagn. Lab. Immunol., 1996, 3: 5-9.
Conrozier et al., "Serum levels of YKL-40 and C reactive protein in patients with hip osteoarthritis and healthy subjects: a cross sectional study", *Ann. Rheum. Dis.*, 2000, 59: 828-231. Corvetta et al., "Terminal complement complex in synovial tissue from patients affected by rheumatoid arthritis, osteoarthritis and acute joint trauma", *Clin. Exp. Rheumtol.*, 1992, 10: 433-438.
Doherty et al., "Relation between synovial fluid C3 degradation products and local joint inflammation in rheumatoid arthritis, osteoarthritis, and crystal associated arthropathy", *Ann. Rheum. Dis.*, 1988, 47: 190-197.
Firestein et al., "Gene expression (collagenase, tissue inhibitor of metalloproteinases, complement, and HLA-DR) in rheumatoid arthritis and osteoarthritis synovium. Quantitative analysis and effect of intraarticular corticosteroids", *Arthritis Rheum.*, 1991, 34: 1094-1105.

(Continued)

*Primary Examiner* — Shubo Zhou
(74) *Attorney, Agent, or Firm* — Tarolli, Sundheim, Covell & Tummino LLP

(57) ABSTRACT

The present invention relates to the identification and use of protein expression profiles with clinical relevance to osteoarthritis (OA). In particular, the invention provides the identity of marker proteins whose expressions are correlated with OA, OA subtype, and/or OA progression. Methods and kits are described for using these protein expression profiles in the study and/or diagnosis of OA, in the determination of the degree of advancement of OA, and in the selection and/or monitoring of treatment regimens. The invention also relates to the screening of drugs that modulate expression of these proteins or nucleic acid molecules encoding these proteins, in particular for the development of disease-modifying OA agents.

4 Claims, 32 Drawing Sheets

OTHER PUBLICATIONS

Garnero et al., "Molecular basis and clinical use of biochemical markers of bone, cartilage, and synovium in joint diseases.", *Arthritis Rheum.*, 2000, 43: 953-968.

Garnero et al., "Cross sectional evaluation of biochemical markers of bone, cartilage, and synovial tissue metabolism in patients with knee osteoarthritis: relations with disease activity and joint damage", *Ann. Rheum. Dis.*, 2001, 60: 619-626.

Harvey et al., "The relationship between serum levels of YKL-40 and disease progression in patients with early rheumatoid arthritis", *Scand. J. Rheumatol.*, 2000, 29: 391-393.

Hedbom et al., "Cartilage matrix proteins. An acidic oligomeric protein (COMP) detected only in cartilage", *J. Biol. Chem.*, 1992, 267: 6132-6136.

Hofmann et al., "RAGE mediates a novel proinflammatory axis: a central cell surface receptor for S100/calgranulin polypeptides", *Cell*, 1999, 97: 889-901.

Hou et al., "Comparison of cathepsins K and S expression within the rheumatoid and osteoarthritic synovium", *Arthritis Rheum.*, 2002, 46: 663-674.

Jay et al., "Homology of lubricin and superficial zone protein (SZP): products of megakaryocyte stimulating factor (MSF) gene expression by human synovial fibroblasts and articular chondrocytes localized to chromosome 1q25", *Orthop. Res.*, 2001, 19: 677-687.

Jerkovic et al., "Afamin is a novel human vitamin E-binding glycoprotein characterization and in vitro expression", *J. Proteome Res.*, 2005, 4: 889-999.

Johansen et al., "A new biochemical marker for joint injury. Analysis of YKL-40 in serum and synovial fluid", *Br. J. Rheumatol.*, 1993, 32: 949-955.

Johansen et al., "Serum YKL-40 levels in healthy children and adults. Comparison with serum and synovial fluid levels of YKL-40 in patients with osteoarthritis or trauma of the knee joint.", *Br. J. Rheumatol.*, 1996, 35: 553-559.

Katz and R.C. Strunk, "Synovial fibroblast-like cells synthesize seven proteins of the complement system", *Arthritis Rheum.*, 1988, 31: 1365-1370.

Keyszer et al., "Comparative analysis of cathepsin L, cathepsin D, and collagenase messenger RNA expression in synovial tissues of patients with rheumatoid arthritis and osteoarthritis, by in situ hybridization", *Arthritis Rheum.*, 1995, 38: 976-984.

Knudson et al., "Cartilage proteoglycans", *Semin. Cell Dev. Biol.*, 2001, 12: 69-78.

Konttinen et al., "Acidic cysteine endoproteinase cathepsin K in the degeneration of the superficial articular hyaline cartilage in osteoarthritis", *Arthritis Rheum.*, 2002, 46: 953-960.

Lenarcic et al., "Human cathepsin B and cysteine proteinase inhibitors (CPIs) in inflammatory and metabolic joint diseases", *Biol. Chem. Hoppe Seyler*, 1988, 369 Suppl: 257-261.

Liao et al., "Use of mass spectrometry to identify protein biomarkers of disease severity in the synovial fluid and serum of patients with rheumatoid arthritis", *Arthritis Rheum.*, 2004, 50: 3792-3803.

Lohmander et al., "Release of cartilage oligomeric matrix protein (COMP) into joint fluid after knee injury and in osteoarthritis", *Ann. Rheum. Dis.*, 1994, 53: 8-13.

Lohmander et al., "Changes in joint cartilage aggrecan after knee injury and in osteoarthritis", *Arthritis Rheum.*, 1999, 42: 534-544.

Lorenz et al., "From transcriptome to proteome: differentially expressed proteins identified in synovial tissue of patients suffering from rheumatoid arthritis and osteoarthritis by an initial screen with a panel of 791 antibodies", *Proteomics*, 2003, 3: 991-1002.

Lorenzo et al., "A novel cartilage protein (CILP) present in the mid-zone of human articular cartilage increases with age", *J. Biol. Chem.*, 1998, 273: 23463-23468.

Manicourt et al., "Synovial fluid levels of tumor necrosis factor a and oncostatin M correlated with levels of markers of the degradation of crosslinked collagen and cartilage aggrecan in rheumatoid arthritis but not in osteoarthritis", *Arthritis Rheum.*, 2000, 43: 281-288.

Mansson et al., "Cartilage and bone metabolism in rheumatoid arthritis. Differences between rapid and slow progression of disease identified by serum markers of cartilage metabolism", *J. Clin. Invest.*, 1995, 1071-1077.

Martel-Pelletier et al., "Cathepsin B and cysteine protease inhibitors in human osteoarthritis", *J. Orthop. Res.*, 1990, 8: 336-344.

Mehraban et al., "Serum keratan sulfate. Quantitative and qualitative comparisons in inflammatory versus noninflammatory arthritides", *Arthritis Rheum.*, 1991, 34: 383-392.

Morko et al., "Up regulation of cathepsin K expression in articular chondrocytes in a transgenic mouse model for osteoarthritis", *Ann. Rheum. Dis.*, 2004, 63: 649-655.

Neumann et al., "Local production of complement proteins in rheumatoid arthritis synovium", *Arthritis Rheum.*, 2002, 46: 934-945.

Olmez et al., "C3 activation products, C3 containing immune complexes, the terminal complement complex and native C9 in patients with rheumatoid arthritis", *Scand. J. Rheumatol.*, 1991, 20: 183-189.

Ott and J. Montes-Lucero, "Osteoarthritis and MR imaging", *Radiol. Technol.*, 2002, 74: 25-42.

Poole et al., "Changes in cartilage metabolism in arthritis are reflected by altered serum and synovial fluid levels of the cartilage proteoglycan aggrecan. Implications for pathogenesis", *J. Clin. Invest.*, 1994, 94: 35-33.

Rhee et al., "The secreted glycoprotein lubricin protects cartilage surfaces and inhibits synovial cell overgrowth", *J. Clin. Invest.*, 2005, 115: 622-631.

Rhee et al., "Consequences of disease-causing mutations on lubricin protein synthesis, secretion, and post-translational processing", *J. Biol. Chem.*, 2005, 280: 31325-3133.

Recklies et al., "Regulation of cartilage oligomeric matrix protein synthesis in human synovial cells and articular chondrocytes", *Arthritis Rheum.*, 1998, 41: 997-1006.

Rizkalla et al., "Studies of the articular cartilage proteoglycan aggrecan in health and osteoarthritis. Evidence for molecular heterogeneity and extensive molecular changes in disease", *J. Clin. Invest.*, 1992, 90: 2268-2277.

Rieg et al., "Generation of multiple stable dermcidin-derived antimicrobial peptides in sweat of different body sites", *J. Invest. Dermatol.*, 2006, 126: 354-365.

Ruiz-Romero et al., "Proteomic characterization of human normal articular chondrocytes: a novel tool for the study of osteoarthritis and other rheumatic diseases", *Proteomics*, 2005, 5:3048-3059.

Saxne et al., "Release of cartilage macromolecules into the synovial fluid in patients with acute and prolonged phases of reactive arthritis", *Arthritis Rheum.*, 1993, 36: 20-25.

Schittek et al., "Dermcidin: a novel human antibiotic peptide secreted by sweat glands", *Nat. Immunol.*, 2001, 2: 1133-1137.

Sharif et al., "Relationship between serum cartilage oligomeric matrix protein levels and disease progression in osteoarthritis of the knee joint", *Br. J. Rheumatol.*, 1995, 34: 306-310.

Sharif et al., "The relevance of chondroitin and keratan sulphate markers in normal and arthritic synovial fluid", *Br. J. Rheumatol.*, 1996, 35: 951-957.

Sharif et al., "Suggestion of nonlinear or phasic progression of knee osteoarthritis based on measurements of serum cartilage oligomeric matrix protein levels over five years", *Arthritis Rheum.*, 2004, 50: 2479-2488.

Sheikh and Kaplan, "Assessment of kininases in rheumatic diseases and the effect of therapeutic agents", *Arthritis Rheum.*, 1987, 30: 138-145.

Sinz et al., "Mass spectrometric proteome analyses of synovial fluids and plasmas from patient suffering from rheumatoid arthritis and comparison to reactive arthritis or osteoarthritis", *Electrophoresis*, 2002, 23: 3445-3456.

Skoumal et al., "Serum levels of cartilage oligomeric matrix protein. A predicting factor and a valuable parameter for disease management in rheumatoid arthritis.", *Scand. J. Rheumatol.*, 2003, 32: 156-161.

Swoboda et al., "Increased content of type-VI collagen epitopes in human osteoarthritic cartilage: quantitation by inhibition ELISA", *J. Orthop. Res.*, 1998, 16: 96-99.

Turk and Bode, "The cystatins: protein inhibitors of cysteine proteinases", *FEBS Lett.*, 1991, 285: 213-219.

Valencia et al., "Divergent pathways of gene expression are activated by the RAGE ligands S100b and AGE-BSA", *Diabetes*, 2004, 53: 743-751.

Vilim et al., "Characterization of monoclonal antibodies recognizing different fragments of cartilage oligomeric matrix protein in human body fluids", *Arch. Biochem. Biophys.*, 1997, 341: 8-16.

Worthy et al., "Kallikreins and kinins: mediators in inflammatory joint disease?", *Int. J. Exp. Pathol.*, 1990, 71: 587-601.

Yamagiwa et al., "Two dimensional gel electrophoresis of synovial fluid: method for detecting candidate protein markers for osteoarthrits", *Journal of Orthopaedic Science*, 2003, 8: 482-490.

\* cited by examiner

| |
|---|
| apolipoprotein E |
| complement component 3 |
| fibrinogen, A alpha polypeptide |
| afamin |
| alpha-2-macroglobulin |
| apolipoprotein B (including Ag(x) antigen) |
| fibrinogen, gamma polypeptide |
| plasminogen |
| orosomucoid 1 |
| group-specific component (vitamin D binding protein) |
| apolipoprotein H (beta-2-glycoprotein I) |
| alpha-1-microglobulin/bikunin precursor |
| complement component 4A |
| serine (or cysteine) proteinase inhibitor, clade G |
| fibrinogen, B beta polypeptide |
| ceruloplasmin (ferroxidase) |
| fibronectin 1 |
| H factor 1 (complement) |
| serine (or cysteine) proteinase inhibitor, clade A |
| transferrin |
| inter-alpha (globulin) inhibitor H1 |
| inter-alpha (globulin) inhibitor H2 |
| orosomucoid 2 |
| pregnancy-zone protein |
| kininogen 1 |
| B-factor, properdin |

Figure 1

| |
|---|
| complement component 3 0 |
| ceruloplasmin (ferroxidase) |
| apolipoprotein H (beta-2-glycoprotein I) |
| group-specific component (vitamin D binding protein) |
| H factor 1 (complement) |
| orosomucoid 1 |
| serine (or cysteine) proteinase inhibitor, clade A |
| haptoglobin |
| alpha-1-microglobulin/bikunin precursor |
| fibrinogen, gamma polypeptide |
| fibrinogen, B beta polypeptide |
| apolipoprotein B (including Ag(x) antigen) |
| apolipoprotein E |
| transferrin |
| fibronectin 1 |
| complement component 4A |
| alpha-2-macroglobulin |
| transferrin // 3q22.1 |
| fibrinogen, A alpha polypeptide |
| fibronectin 1 |
| complement component 1, q subcomponent, beta polypeptide |
| haptoglobin-related protein |
| serine proteinase inhibitor, clade A , member 3 |
| orosomucoid 2 |
| plasminogen |
| afamin |
| lumican |

Figure 2

| |
|---|
| serine proteinase inhibitor, clade A |
| apolipoprotein B antigen) |
| paraoxonase 1 |
| keratin 6A |
| fibronectin 1 |
| alpha-2-macroglobulin |
| keratin 2A |
| transferrin |
| group-specific component |
| complement component 3 |
| ceruloplasmin (ferroxidase) |
| keratin 4 |
| keratin 14 |

Figure 3

| |
|---|
| aggrecan 1 |
| paraoxonase 1 |
| keratin 6A |
| keratin 6B |
| keratin 4 |
| keratin 14 |
| keratin 10 |
| keratin 8 |
| keratin 2A |
| keratin 1 |

Figure 4

| |
|---|
| aggrecan 1 |
| gelosin (amyloidosis) |
| albumin |
| keratin 4 |
| keratin 6A |
| keratin 6B |

Figure 5

| |
|---|
| aggrecan 1 |
| albumin |
| kininogen |
| inter-alpha (globulin) inhibitor H1 |
| inter-alpha (globulin) inhibitor H2 |
| alpha-1-microglobulin/bikunin precursor |

| |
|---|
| fibronectin 1 isoform 1 preproprotein |
| ceruloplasmin (ferroxidase) |
| serine (or cysteine) proteinase inhibitor, clade A (alpha-1 antiproteinase, antitrypsin), member 1 (NP_001002236) |
| PREDICTED: similar to Apolipoprotein A-I precursor (Apo-AI) (XP_496536) |
| haptoglobin |
| transferrin |
| group-specific component (vitamin D binding protein) |
| complement component 3 |
| orosomucoid 1 |
| fibrinogen, B beta polypeptide |
| fibrinogen, gamma chain isoform gamma-A precursor |
| H factor 1 (complement) |
| complement component 3 |
| alpha-2-macroglobulin |
| apolipoprotein E |
| haptoglobin |
| transferrin |
| transferrin |
| apolipoprotein H (beta-2-glycoprotein I) |
| complement component 4B preproprotein (NP_001002029) |
| fibrinogen, alpha chain isoform alpha-E preproprotein |
| alpha-1-microglobulin/bikunin precursor |
| retinol-binding protein 4, plasma precursor (NP_006735) |
| serine (or cysteine) proteinase inhibitor, clade A (alpha-1 antiproteinase, antitrypsin), member 1 (NP_000286) |
| fibrinogen, B beta polypeptide |
| apolipoprotein B (including Ag(x) antigen) |
| fibrinogen, alpha chain isoform alpha-E preproprotein |
| dermcidin |
| cystatin A (stefin A) |
| aggrecan 1 (chondroitin sulfate proteoglycan 1, large aggregating proteoglycan, antigen identified by monoclonal antibody A0122) |

(B)

| |
|---|
| haptoglobin |
| serine (or cysteine) proteinase inhibitor, clade A, member 3 precursor (NP_001076) |
| serine (or cysteine) proteinase inhibitor, clade A, member 3 precursor (NP_001076) |
| inter-alpha (globulin) inhibitor H2 |
| complement component 3 |
| alpha-2-macroglobulin |
| alpha-2-macroglobulin |

Figure 7

| slice | gid | Name | P-value (E-N) |
|---|---|---|---|
| 9 | 4826762 | haptoglobin | 0.000 |
| 9 | 47132551 | fibronectin 1 isoform 2 preproprotein | 0.000 |
| 6 | 50659080 | serine (or cysteine) proteinase inhibitor, clade A, member 3 precursor (NP_001076) | 0.000 |
| 5 | 19923106 | paraoxonase 1 | 0.000 |
| 9 | 50659080 | serine (or cysteine) proteinase inhibitor, clade A, member 3 precursor (NP_001076) | 0.000 |
| 9 | 4504783 | inter-alpha (globulin) inhibitor H2 | 0.000 |
| 6 | 4502153 | apolipoprotein B (including Ag(x) antigen) | 0.000 |
| 1 | 4504783 | inter-alpha (globulin) inhibitor H2 | 0.000 |
| 1 | 4502153 | apolipoprotein B (including Ag(x) antigen) | 0.000 |
| 4 | 4502027 | *albumin* | 0.000 |
| 5 | 4557871 | transferrin | 0.000 |
| 3 | 47132557 | fibronectin 1 isoform 1 preproprotein | 0.000 |
| 9 | 50363219 | serine (or cysteine) proteinase inhibitor, clade A (alpha-1 antiproteinase, antitrypsin), member 1 (NP_001002236) | 0.000 |
| 8 | 4557225 | alpha-2-macroglobulin | 0.000 |
| 9 | 51472914 | PREDICTED: similar to KIAA1501 protein (XP_370973) | 0.000 |
| 7 | 4557871 | transferrin | 0.000 |
| 8 | 4557385 | complement component 3 | 0.000 |
| 3 | 4557485 | ceruloplasmin (ferroxidase) | 0.000 |
| 6 | 16933542 | fibronectin 1 isoform 3 preproprotein | 0.000 |
| 6 | 4557385 | complement component 3 | 0.000 |
| 5 | 47132549 | fibronectin 1 isoform 6 preproprotein | 0.000 |
| 7 | 4557225 | alpha-2-macroglobulin | 0.000 |
| 7 | 47132620 | keratin 2A (epidermal ichthyosis bullosa of Siemens) | 0.000 |
| 6 | 4557225 | alpha-2-macroglobulin | 0.000 |
| 6 | 32483410 | group-specific component (vitamin D binding protein) | 0.000 |
| 9 | 4504781 | inter-alpha (globulin) inhibitor H1 | 0.000 |
| 8 | 4504783 | inter-alpha (globulin) inhibitor H2 | 0.000 |
| 7 | 15431310 | keratin 14 (epidermolysis bullosa simplex, Dowling-Meara, Koebner) | 0.000 |
| 1 | 4502067 | alpha-1-microglobulin/bikunin precursor | 0.000 |
| 2 | 4504893 | kininogen 1 | 0.000 |
| 1 | 4504781 | inter-alpha (globulin) inhibitor H1 | 0.000 |
| 5 | 4502027 | albumin | 0.000 |
| 5 | 50363219 | serine (or cysteine) proteinase inhibitor, clade A (alpha-1 antiproteinase, antitrypsin), member 1 (NP_001002236) | 0.000 |
| 6 | 4502027 | albumin | 0.000 |
| 7 | 51476111 | PREDICTED: similar to Apolipoprotein A-I precursor (Apo-AI) (XP_496536) | 0.000 |
| 7 | 4502027 | albumin | 0.000 |
| 5 | 4826762 | haptoglobin | 0.000 |
| 8 | 4502027 | albumin | 0.000 |
| 3 | 4557871 | transferrin | 0.000 |
| 5 | 32483410 | group-specific component (vitamin D binding protein) | 0.000 |
| 2 | 47132555 | fibronectin 1 isoform 4 preproprotein | 0.000 |
| 5 | 4557385 | complement component 3 | 0.000 |
| 5 | 9257232 | orosomucoid 1 | 0.000 |

Figure 8(A)

| slice | gid | Name | P-value (E-N) |
|---|---|---|---|
| 5 | 11761631 | fibrinogen, B beta polypeptide | 0.000 |
| 3 | 4503715 | fibrinogen, gamma chain isoform gamma-A precursor | 0.000 |
| 2 | 4504375 | H factor 1 (complement) | 0.000 |
| 3 | 4557225 | alpha-2-macroglobulin | 0.000 |
| 3 | 4557385 | complement component 3 | 0.000 |
| 5 | 4557225 | alpha-2-macroglobulin | 0.000 |
| 6 | 4557325 | apolipoprotein E | 0.001 |
| 3 | 4502397 | B-factor, properdin | 0.001 |
| 8 | 4826762 | haptoglobin | 0.001 |
| 3 | 4557379 | serine (or cysteine) proteinase inhibitor, clade G (C1 inhibitor), member 1, (angioedema, hereditary) | 0.001 |
| 6 | 4557871 | transferrin | 0.001 |
| 8 | 4557871 | transferrin | 0.001 |
| 5 | 4557327 | apolipoprotein H (beta-2-glycoprotein I) | 0.001 |
| 9 | 4557385 | complement component 3 | 0.001 |
| 3 | 4505881 | plasminogen | 0.001 |
| 6 | 50363221 | serine (or cysteine) proteinase inhibitor, clade A (alpha-1 antiproteinase, antitrypsin), member 1 (NP_001002235) | 0.001 |
| 5 | 4502151 | apolipoprotein A-IV | 0.001 |
| 6 | 50345296 | complement component 4B preproprotein (NP_001002029) | 0.002 |
| 6 | 4503689 | fibrinogen, alpha chain isoform alpha-E preproprotein | 0.002 |
| 3 | 4501987 | afamin | 0.002 |
| 6 | 4502067 | alpha-1-microglobulin/bikunin precursor | 0.002 |
| 9 | 51476113 | PREDICTED: similar to Apolipoprotein C-III precursor (Apo-CIII) (XP_496537) | 0.002 |
| 6 | 4826762 | haptoglobin | 0.002 |
| 6 | 42740907 | clusterin (complement lysis inhibitor, SP-40,40, sulfated glycoprotein 2, testosterone-repressed prostate message 2, apolipoprotein J) | 0.003 |
| 5 | 4505529 | orosomucoid 2 | 0.003 |
| 8 | 55743122 | retinol-binding protein 4, plasma precursor (NP_006735) | 0.003 |
| 8 | 50363217 | serine (or cysteine) proteinase inhibitor, clade A (alpha-1 antiproteinase, antitrypsin), member 1 (NP_000286) | 0.003 |
| 8 | 51476111 | PREDICTED: similar to Apolipoprotein A-I precursor (Apo-AI) (XP_496536) | 0.004 |
| 5 | 4502005 | alpha-2-HS-glycoprotein | 0.004 |
| 6 | 4503715 | fibrinogen, gamma chain isoform gamma-A precursor | 0.004 |
| 6 | 11761631 | fibrinogen, B beta polypeptide | 0.005 |
| 2 | 4502153 | apolipoprotein B (including Ag(x) antigen) | 0.005 |
| 7 | 11038662 | complement component 1, q subcomponent, beta polypeptide | 0.005 |
| 3 | 4502153 | apolipoprotein B (including Ag(x) antigen) | 0.005 |
| 3 | 4505047 | lumican | 0.006 |
| 8 | 16933542 | fibronectin 1 isoform 3 preproprotein | 0.007 |
| 9 | 4503689 | fibrinogen, alpha chain isoform alpha-E preproprotein | 0.008 |
| 8 | 4503689 | fibrinogen, alpha chain isoform alpha-E preproprotein | 0.009 |
| 8 | 4557393 | complement component 8, gamma polypeptide | 0.009 |
| 2 | 4504781 | inter-alpha (globulin) inhibitor H1 | 0.010 |
| 8 | 4557485 | ceruloplasmin (ferroxidase) | 0.010 |
| 2 | 6995994 | aggrecan 1 (chondroitin sulfate proteoglycan 1, large aggregating proteoglycan, antigen identified by monoclonal antibody A0122) | 0.010 |
| 9 | 16751921 | dermcidin | 0.011 |

Figure 8(B)

| slice | gid | Name | P-value (E-N) |
|---|---|---|---|
| 9 | 4885165 | cystatin A (stefin A) | 0.011 |
| 9 | 4504351 | hemoglobin, delta | 0.012 |
| 3 | 6995994 | aggrecan 1 (chondroitin sulfate proteoglycan 1, large aggregating proteoglycan, antigen identified by monoclonal antibody A0122) | 0.012 |
| 9 | 55956899 | keratin 9 (NP_000217) | 0.013 |
| 3 | 47132620 | keratin 2A (epidermal ichthyosis bullosa of Siemens) | 0.014 |
| 9 | 40354192 | keratin 10 (epidermolytic hyperkeratosis; keratosis palmaris et plantaris) | 0.014 |
| 9 | 17318569 | keratin 1 (epidermolytic hyperkeratosis) | 0.014 |
| 3 | 40354192 | keratin 10 (epidermolytic hyperkeratosis; keratosis palmaris et plantaris) | 0.016 |
| 2 | 4557225 | alpha-2-macroglobulin | 0.017 |
| 2 | 31542984 | inter-alpha (globulin) inhibitor H4 (plasma Kallikrein-sensitive glycoprotein) | 0.017 |
| 2 | 4504783 | inter-alpha (globulin) inhibitor H2 | 0.018 |
| 7 | 4557385 | complement component 3 | 0.018 |
| 3 | 4504783 | inter-alpha (globulin) inhibitor H2 | 0.020 |
| 6 | 4502163 | apolipoprotein D | 0.021 |
| 1 | 4503689 | fibrinogen, alpha chain isoform alpha-E preproprotein | 0.022 |
| 8 | 4504349 | hemoglobin, beta | 0.022 |
| 3 | 38016947 | complement component 5 | 0.022 |
| 8 | 11761631 | fibrinogen, B beta polypeptide | 0.022 |
| 3 | 4503635 | coagulation factor II (thrombin) | 0.022 |
| 6 | 11038662 | complement component 1, q subcomponent, beta polypeptide | 0.022 |
| 6 | 4557485 | ceruloplasmin (ferroxidase) | 0.024 |
| 1 | 11761633 | fibrinogen, gamma chain isoform gamma-B precursor | 0.026 |
| 8 | 32483410 | group-specific component (vitamin D binding protein) | 0.026 |
| 8 | 10835095 | serum amyloid A4, constitutive | 0.028 |
| 3 | 4502067 | alpha-1-microglobulin/bikunin precursor | 0.029 |
| 6 | 19923106 | paraoxonase 1 | 0.029 |
| 8 | 4502501 | complement component 4A | 0.031 |
| 1 | 4557225 | alpha-2-macroglobulin | 0.033 |
| 5 | 14577919 | complement component 4A | 0.039 |
| 6 | 4504579 | I factor (complement) | 0.039 |
| 2 | 14577919 | complement component 4A | 0.039 |
| 8 | 4557890 | keratin 4 | 0.041 |
| 3 | 4557890 | keratin 4 | 0.041 |
| 1 | 24430192 | keratin 16 (focal non-epidermolytic palmoplantar keratoderma) | 0.041 |
| 9 | 24430192 | keratin 16 (focal non-epidermolytic palmoplantar keratoderma) | 0.043 |
| 9 | 15431310 | keratin 14 (epidermolysis bullosa simplex, Dowling-Meara, Koebner) | 0.043 |
| 2 | 47132620 | keratin 2A (epidermal ichthyosis bullosa of Siemens) | 0.043 |
| 5 | 39725934 | serine (or cysteine) proteinase inhibitor, clade F (alpha-2 antiplasmin, pigment epithelium derived factor), member 1 | 0.043 |
| 2 | 40354192 | keratin 10 (epidermolytic hyperkeratosis; keratosis palmaris et plantaris) | 0.043 |
| 2 | 55956899 | keratin 9 (NP_000217) | 0.045 |
| 5 | 55956899 | keratin 9 (NP_000217) | 0.045 |
| 9 | 5031925 | proteoglycan 4, (megakaryocyte stimulating factor, articular superficial zone protein, camptodactyly, arthropathy, coxa vara, pericarditis syndrome) | 0.047 |
| 9 | 47132620 | keratin 2A (epidermal ichthyosis bullosa of Siemens) | 0.047 |

Figure 8(C)

| slice | gid | Name | P-value (L-N) without 3 LOA Outliers |
|---|---|---|---|
| 5 | 4557385 | complement component 3 | 0.000 |
| 6 | 4557385 | complement component 3 | 0.000 |
| 6 | 4557871 | transferrin | 0.000 |
| 3 | 4557485 | ceruloplasmin (ferroxidase) | 0.000 |
| 7 | 51476111 | PREDICTED: similar to Apolipoprotein A-I precursor (Apo-AI) (XP_496536) | 0.000 |
| 8 | 4557385 | complement component 3 | 0.000 |
| 6 | 50345296 | complement component 4B preproprotein (NP_001002029) | 0.000 |
| 6 | 4502067 | alpha-1-microglobulin/bikunin precursor | 0.000 |
| 5 | 4557327 | apolipoprotein H (beta-2-glycoprotein I) | 0.000 |
| 5 | 32483410 | group-specific component (vitamin D binding protein) | 0.000 |
| 6 | 4503689 | fibrinogen, alpha chain isoform alpha-E preproprotein | 0.000 |
| 6 | 4557325 | apolipoprotein E | 0.000 |
| 6 | 4502027 | albumin | 0.000 |
| 5 | 9257232 | orosomucoid 1 | 0.000 |
| 5 | 11761631 | fibrinogen, B beta polypeptide | 0.000 |
| 3 | 4557385 | complement component 3 | 0.000 |
| 2 | 4504375 | H factor 1 (complement) | 0.000 |
| 8 | 4826762 | haptoglobin | 0.000 |
| 5 | 50363219 | serine (or cysteine) proteinase inhibitor, clade A (alpha-1 antiproteinase, antitrypsin), member 1 (NP_001002236) | 0.000 |
| 5 | 4826762 | haptoglobin | 0.000 |
| 8 | 55743122 | retinol-binding protein 4, plasma precursor (NP_006735) | 0.000 |
| 5 | 4557225 | alpha-2-macroglobulin | 0.000 |
| 3 | 6995994 | aggrecan 1 (chondroitin sulfate proteoglycan 1, large aggregating proteoglycan, antigen identified by monoclonal antibody A0122) | 0.000 |
| 6 | 11761631 | fibrinogen, B beta polypeptide | 0.000 |
| 9 | 4885165 | cystatin A (stefin A) | 0.000 |
| 3 | 4503715 | fibrinogen, gamma chain isoform gamma-A precursor | 0.000 |
| 8 | 4557871 | transferrin | 0.000 |
| 5 | 4502027 | albumin | 0.000 |
| 7 | 11038662 | complement component 1, q subcomponent, beta polypeptide | 0.000 |
| 9 | 16751921 | dermcidin | 0.000 |
| 2 | 4502153 | apolipoprotein B (including Ag(x) antigen) | 0.000 |
| 6 | 16933542 | fibronectin 1 isoform 3 preproprotein | 0.000 |
| 8 | 4503689 | fibrinogen, alpha chain isoform alpha-E preproprotein | 0.000 |
| 8 | 4557485 | ceruloplasmin (ferroxidase) | 0.000 |
| 3 | 47132557 | fibronectin 1 isoform 1 preproprotein | 0.000 |
| 9 | 40354192 | keratin 10 (epidermolytic hyperkeratosis; keratosis palmaris et plantaris) | 0.000 |
| 9 | 17318569 | keratin 1 (epidermolytic hyperkeratosis) | 0.000 |
| 8 | 50363217 | serine (or cysteine) proteinase inhibitor, clade A (alpha-1 antiproteinase, antitrypsin), member 1 (NP_000286) | 0.000 |
| 7 | 4502027 | albumin | 0.000 |
| 5 | 4557871 | transferrin | 0.000 |
| 8 | 4502027 | albumin | 0.000 |
| 9 | 51476113 | PREDICTED: similar to Apolipoprotein C-III precursor (Apo-CIII) (XP_496537) | 0.000 |

Figure 9(A)

| slice | gid | Name | P-value (L-N) without 3 LOA Outliers |
|---|---|---|---|
| 6 | 50659080 | serine (or cysteine) proteinase inhibitor, clade A, member 3 precursor (NP_001076) | 0.000 |
| 3 | 47132620 | keratin 2A (epidermal ichthyosis bullosa of Siemens) | 0.000 |
| 6 | 4826762 | haptoglobin | 0.000 |
| 3 | 4557871 | transferrin | 0.001 |
| 6 | 50363221 | serine (or cysteine) proteinase inhibitor, clade A (alpha-1 antiproteinase, antitrypsin), member 1 (NP_001002235) | 0.001 |
| 6 | 4503715 | fibrinogen, gamma chain isoform gamma-A precursor | 0.001 |
| 3 | 4505881 | plasminogen | 0.001 |
| 3 | 4501987 | afamin | 0.001 |
| 9 | 4826762 | haptoglobin | 0.001 |
| 5 | 4502151 | apolipoprotein A-IV | 0.001 |
| 9 | 55956899 | keratin 9 (NP_000217) | 0.002 |
| 2 | 4504781 | inter-alpha (globulin) inhibitor H1 | 0.002 |
| 8 | 51476111 | PREDICTED: similar to Apolipoprotein A-I precursor (Apo-AI) (XP_496536) | 0.002 |
| 7 | 4557225 | alpha-2-macroglobulin | 0.002 |
| 6 | 42740907 | clusterin (complement lysis inhibitor, SP-40,40, sulfated glycoprotein 2, testosterone-repressed prostate message 2, apolipoprotein J) | 0.002 |
| 3 | 4505047 | lumican | 0.004 |
| 4 | 4502027 | *albumin* | 0.004 |
| 6 | 4557225 | alpha-2-macroglobulin | 0.004 |
| 3 | 4557379 | serine (or cysteine) proteinase inhibitor, clade G (C1 inhibitor), member 1, (angioedema, hereditary) | 0.004 |
| 9 | 47132620 | keratin 2A (epidermal ichthyosis bullosa of Siemens) | 0.004 |
| 9 | 4504351 | hemoglobin, delta | 0.004 |
| 9 | 4504783 | inter-alpha (globulin) inhibitor H2 | 0.006 |
| 9 | 4557385 | complement component 3 | 0.006 |
| 3 | 4502153 | apolipoprotein B (including Ag(x) antigen) | 0.006 |
| 8 | 16933542 | fibronectin 1 isoform 3 preproprotein | 0.006 |
| 1 | 11761633 | fibrinogen, gamma chain isoform gamma-B precursor | 0.006 |
| 2 | 6995994 | aggrecan 1 (chondroitin sulfate proteoglycan 1, large aggregating proteoglycan, antigen identified by monoclonal antibody A0122) | 0.006 |
| 3 | 4502397 | B-factor, properdin | 0.008 |
| 6 | 4502163 | apolipoprotein D | 0.009 |
| 3 | 4557225 | alpha-2-macroglobulin | 0.009 |
| 2 | 4504783 | inter-alpha (globulin) inhibitor H2 | 0.011 |
| 2 | 55956899 | keratin 9 (NP_000217) | 0.011 |
| 5 | 55956899 | keratin 9 (NP_000217) | 0.012 |
| 9 | 47132551 | fibronectin 1 isoform 2 preproprotein | 0.013 |
| 6 | 4502153 | apolipoprotein B (including Ag(x) antigen) | 0.013 |
| 8 | 11761631 | fibrinogen, B beta polypeptide | 0.013 |
| 3 | 4503635 | coagulation factor II (thrombin) | 0.013 |
| 6 | 11038662 | complement component 1, q subcomponent, beta polypeptide | 0.013 |
| 6 | 4557485 | ceruloplasmin (ferroxidase) | 0.013 |
| 1 | 4557225 | alpha-2-macroglobulin | 0.013 |
| 5 | 14577919 | complement component 4A | 0.013 |

Figure 9(B)

| slice | gid | Name | P-value (L-N) without 3 LOA Outliers |
|---|---|---|---|
| 9 | 4507725 | transthyretin (prealbumin, amyloidosis type I) | 0.013 |
| 5 | 4502005 | alpha-2-HS-glycoprotein | 0.013 |
| 8 | 4557393 | complement component 8, gamma polypeptide | 0.015 |
| 8 | 47132620 | keratin 2A (epidermal ichthyosis bullosa of Siemens) | 0.016 |
| 2 | 47132555 | fibronectin 1 isoform 4 preproprotein | 0.017 |
| 1 | 4503689 | fibrinogen, alpha chain isoform alpha-E preproprotein | 0.017 |
| 5 | 39725934 | serine (or cysteine) proteinase inhibitor, clade F (alpha-2 antiplasmin, pigment epithelium derived factor), member 1 | 0.019 |
| 2 | 31542984 | inter-alpha (globulin) inhibitor H4 (plasma Kallikrein-sensitive glycoprotein) | 0.019 |
| 9 | 4503689 | fibrinogen, alpha chain isoform alpha-E preproprotein | 0.020 |
| 8 | 4557225 | alpha-2-macroglobulin | 0.021 |
| 5 | 4505529 | orosomucoid 2 | 0.024 |
| 3 | 40354192 | keratin 10 (epidermolytic hyperkeratosis; keratosis palmaris et plantaris) | 0.024 |
| 7 | 4557385 | complement component 3 | 0.025 |
| 8 | 4507557 | tetranectin (plasminogen binding protein) | 0.025 |
| 9 | 24430192 | keratin 16 (focal non-epidermolytic palmoplantar keratoderma) | 0.025 |
| 8 | 10835095 | serum amyloid A4, constitutive | 0.025 |
| 5 | 4504489 | histidine-rich glycoprotein | 0.027 |
| 4 | 21071030 | alpha-1-B glycoprotein | 0.027 |
| 5 | 47132549 | fibronectin 1 isoform 6 preproprotein | 0.028 |
| 9 | 4504781 | inter-alpha (globulin) inhibitor H1 | 0.028 |
| 8 | 4504783 | inter-alpha (globulin) inhibitor H2 | 0.028 |
| 8 | 32483410 | group-specific component (vitamin D binding protein) | 0.028 |
| 3 | 4502067 | alpha-1-microglobulin/bikunin precursor | 0.028 |
| 2 | 4557225 | alpha-2-macroglobulin | 0.028 |
| 9 | 15431310 | keratin 14 (epidermolysis bullosa simplex, Dowling-Meara, Koebner) | 0.035 |
| 9 | 5031925 | proteoglycan 4, (megakaryocyte stimulating factor, articular superficial zone protein, camptodactyly, arthropathy, coxa vara, pericarditis syndrome) | 0.038 |
| 1 | 24430192 | keratin 16 (focal non-epidermolytic palmoplantar keratoderma) | 0.042 |
| 1 | 55956899 | keratin 9 (NP_000217) | 0.043 |
| 3 | 4502493 | complement component 1, r subcomponent | 0.045 |
| 8 | 4507725 | transthyretin (prealbumin, amyloidosis type I) | 0.045 |
| 2 | 40354192 | keratin 10 (epidermolytic hyperkeratosis; keratosis palmaris et plantaris) | 0.045 |
| 9 | 51472914 | PREDICTED: similar to KIAA1501 protein (XP_370973) | 0.045 |
| 5 | 4505047 | lumican | 0.045 |
| 3 | 55956899 | keratin 9 (NP_000217) | 0.046 |
| 8 | 4557890 | keratin 4 | 0.048 |
| 3 | 4557890 | keratin 4 | 0.048 |
| 6 | 4502397 | B-factor, properdin | 0.049 |

Figure 9(C)

| Name | P-value (E-N)) | Avg_E-Avg_N | P-value (L-N) without 3 LOA Outliers | Avg_L-Avg_N without 3 LOA Outliers | P-value (L-E) without 3 LOA Outliers | Avg_L-Avg_E without 3 LOA Outliers | P-value ((E,L)-N) without 3 LOA Outliers | Avg_(E,L)-Avg_N without 3 LOA Outliers |
|---|---|---|---|---|---|---|---|---|
| haptoglobin | 0.3962 | 53.4548 | 0.0011 | 1506.43 | 0.0048 | 1452.98 | 0.0220 | 724.06 |
| serine (or cysteine) proteinase inhibitor, clade A, member 3 precursor (NP_001076) | 0.3291 | 1.481 | 0.0004 | 339.3 | 0.0010 | 337.819 | 0.0143 | 157.397 |
| serine (or cysteine) proteinase inhibitor, clade A, member 3 precursor (NP_001076) | 0.1300 | -19.178 | 0.1888 | 291.877 | 0.0075 | 311.056 | 0.9455 | 124.386 |
| inter-alpha (globulin) inhibitor H2 | 1.0000 | 0 | 0.0057 | 244.722 | 0.0047 | 244.722 | 0.0670 | 112.949 |
| fibronectin 1 isoform 1 preproprotein | 0.0000 | 1446.9 | 0.0002 | 3445.78 | 0.0423 | 1998.88 | 0.0000 | 2369.46 |
| ceruloplasmin (ferroxidase) | 0.0000 | 491.532 | 0.0000 | 1017.39 | 0.0650 | 525.859 | 0.0000 | 734.236 |
| complement component 3 | 0.0030 | 401.299 | 0.0000 | 864.213 | 0.0059 | 462.914 | 0.0000 | 614.952 |
| alpha-2-macroglobulin | 0.3291 | 3.3714 | 0.0025 | 281.767 | 0.0075 | 278.395 | 0.0314 | 131.862 |
| alpha-2-macroglobulin | 0.9324 | 71.0169 | 0.0041 | 323.999 | 0.0088 | 252.983 | 0.0821 | 187.778 |
| serine (or cysteine) proteinase inhibitor, clade A (alpha-1 antiproteinase, antitrypsin), member 1 (NP_001002236) | 0.0000 | 36660.6 | 0.0000 | 40135.2 | 0.5925 | 3474.67 | 0.0000 | 38264.3 |
| PREDICTED: similar to Apolipoprotein A-I precursor (Apo-AI) (XP_496536) | 0.0000 | 38234 | 0.0000 | 34376.2 | 0.9775 | -3857.9 | 0.0000 | 36453.5 |
| haptoglobin | 0.0003 | 8955.93 | 0.0000 | 8635.93 | 0.9101 | -320 | 0.0000 | 8808.24 |
| transferrin | 0.0001 | 7574.3 | 0.0006 | 6148.2 | 0.5541 | -1426.1 | 0.0000 | 6916.1 |
| group-specific component (vitamin D binding protein) | 0.0000 | 5901.35 | 0.0000 | 6044.71 | 0.9103 | 143.359 | 0.0000 | 5967.52 |
| complement component 3 | 0.0000 | 4469.66 | 0.0000 | 4288.33 | 0.9103 | -181.33 | 0.0000 | 4385.97 |
| orosomucoid 1 | 0.0000 | 4562.55 | 0.0000 | 3412.44 | 0.2367 | -1150.1 | 0.0000 | 4031.73 |
| fibrinogen, B beta polypeptide | 0.0000 | 6069.55 | 0.0000 | 3415.22 | 0.7564 | -2654.3 | 0.0000 | 4844.47 |
| fibrinogen, gamma chain isoform gamma-A precursor | 0.0000 | 3884.9 | 0.0001 | 3363.34 | 0.6623 | -521.57 | 0.0000 | 3644.18 |
| H factor 1 (complement) | 0.0001 | 2892.89 | 0.0000 | 3430.41 | 0.8658 | 537.518 | 0.0000 | 3140.97 |
| complement component 3 | 0.0000 | 1866.37 | 0.0000 | 2358.95 | 0.3673 | 492.578 | 0.0000 | 2093.72 |
| alpha-2-macroglobulin | 0.0000 | 4270 | 0.0000 | 1881.86 | 0.1946 | -2388.1 | 0.0000 | 3167.78 |
| apolipoprotein E | 0.0000 | 3419.95 | 0.0000 | 1899.5 | 0.1354 | -1520.4 | 0.0000 | 2718.2 |
| haptoglobin | 0.0000 | 1619.37 | 0.0000 | 1848.43 | 0.7998 | 229.06 | 0.0000 | 1725.09 |
| transferrin | 0.0008 | 809.706 | 0.0000 | 1827.5 | 0.0166 | 1017.79 | 0.0000 | 1279.46 |
| transferrin | 0.0000 | 1009.26 | 0.0001 | 1736.58 | 0.2844 | 727.325 | 0.0000 | 1344.94 |
| apolipoprotein H (beta-2-glycoprotein I) | 0.0000 | 1513.4 | 0.0000 | 1557.98 | 0.7673 | 44.5889 | 0.0000 | 1533.97 |

Figure 10(A)

| Name | P-value (E-N)) | Avg_E-Avg_N | P-value (L-N) without 3 LOA Outliers | Avg_L-Avg_N without 3 LOA Outliers | P-value (L-E) without 3 LOA Outliers | Avg_L-Avg_E without 3 LOA Outliers | P-value ({E,L}-N) without 3 LOA Outliers | Avg_{E,L}-Avg_N without 3 LOA Outliers |
|---|---|---|---|---|---|---|---|---|
| complement component 4B preproprotein (NP_001002029) | 0.0000 | 933.256 | 0.0000 | 1121.36 | 0.4812 | 188.109 | 0.0000 | 1020.08 |
| fibrinogen, alpha chain isoform alpha-E preproprotein | 0.0000 | 1507.06 | 0.0000 | 994.02 | 0.2835 | -513.04 | 0.0000 | 1270.27 |
| alpha-1-microglobulin/bikunin precursor | 0.0000 | 744.625 | 0.0000 | 923.104 | 0.2481 | 178.479 | 0.0000 | 827 |
| retinol-binding protein 4, plasma precursor (NP_006735) | 0.0000 | 778.87 | 0.0000 | 723.771 | 0.5731 | -55.098 | 0.0000 | 753.44 |
| serine (or cysteine) proteinase inhibitor, clade A (alpha-1 antiproteinase, antitrypsin), member 1 (NP_000286) | 0.0002 | 388.115 | 0.0002 | 728.049 | 0.1022 | 339.935 | 0.0000 | 545.008 |
| fibrinogen, B beta polypeptide | 0.0001 | 562.291 | 0.0001 | 549.656 | 0.6653 | -12.635 | 0.0000 | 556.459 |
| apolipoprotein B (including Ag(x) antigen) | 0.0000 | 752.219 | 0.0001 | 463.422 | 0.6205 | -288.8 | 0.0000 | 618.928 |
| fibrinogen, alpha chain isoform alpha-E preproprotein | 0.0005 | 532.486 | 0.0002 | 301.933 | 0.9284 | -230.55 | 0.0001 | 426.077 |
| dermcidin | 0.0000 | -143.86 | 0.0001 | -143.86 | 1.0000 | 0 | 0.0000 | -143.86 |
| cystatin A (stefin A) | 0.0000 | -176.01 | 0.0001 | -176.01 | 1.0000 | 0 | 0.0000 | -176.01 |
| aggrecan 1 (chondroitin sulfate proteoglycan 1, large aggregating proteoglycan, antigen identified by monoclonal antibody A0122) | 0.0001 | -299.76 | 0.0001 | -320.9 | 0.3545 | -21.143 | 0.0000 | -309.52 |

Figure 10(B)

| Protein Identification | Sensitivity Healthy | Sensitivity Early OA | Sensitivity Late OA | Specificity Healthy | Specificity Early OA | Specificity Late OA |
|---|---|---|---|---|---|---|
| PREDICTED: similar to Apolipoprotein A-I precursor (Apo-AI) (XP_496536) | 0.718 | 0.857 | 0.889 | 0.950 | 0.900 | 0.850 |
| group-specific component (vitamin D binding protein | 0.744 | 0.810 | 0.889 | 1.000 | 0.850 | 0.850 |
| complement component 3 | 0.744 | 0.857 | 0.944 | 1.000 | 0.900 | 0.900 |
| orosomucoid 1 | 0.667 | 0.810 | 0.833 | 0.850 | 0.850 | 0.800 |
| fibrinogen, gamma chain isoform gamma-A precursor | 0.744 | 0.857 | 0.833 | 1.000 | 0.900 | 0.800 |
| complement component 3 | 0.718 | 0.810 | 0.889 | 0.950 | 0.850 | 0.850 |
| alpha-2-macroglobulin | 0.718 | 0.810 | 0.778 | 0.950 | 0.850 | 0.750 |
| apolipoprotein E | 0.744 | 0.952 | 0.889 | 1.000 | 1.000 | 0.850 |
| haptoglobin | 0.718 | 0.810 | 0.889 | 0.950 | 0.850 | 0.850 |
| apolipoprotein H (beta-2-glycoprotein I) | 0.744 | 0.857 | 0.889 | 1.000 | 0.900 | 0.850 |
| complement component 4B preproprotein (NP_001002029) | 0.744 | 0.810 | 0.889 | 1.000 | 0.850 | 0.850 |
| fibrinogen, alpha chain isoform alpha-E preproprotein | 0.718 | 0.857 | 0.833 | 0.950 | 0.900 | 0.850 |
| dermcidin | 1.000 | 1.000 | 1.000 | 0.600 | 0.600 | 0.600 |
| cystatin A (stefin A) | 1.000 | 1.000 | 1.000 | 0.650 | 0.650 | 0.650 |
| aggrecan 1 (chondroitin sulfate proteoglycan 1, large aggregating proteoglycan, antigen identified by monoclonal antibody A0122) | 0.974 | 0.952 | 1.000 | 0.650 | 0.650 | 0.650 |

Figure 13

| G# | Protein Description | Upregulated in | Specificity | Sensitivity | p value Fisher Exact 2-sided | # Samples with area > median Control | # Samples with area ≤ median OA |
|---|---|---|---|---|---|---|---|
| 4885165 | cystatin A (stefin A) | Control | 0.650 | 1.000 | 1.92E-08 | | |
| 6995994 | aggrecan 1 | Control | 0.650 | 0.974 | 2.30E-07 | | |
| 16751921 | dermcidin | Control | 0.600 | 1.000 | 1.13E-07 | | |
| 4502027 | albumin | OA | 0.950 | 0.718 | 7.96E-07 | | |
| 4502067 | alpha-1-microglobulin/bikunin precursor | OA | 0.950 | 0.718 | 7.96E-07 | | |
| 4503689 | fibrinogen, alpha chain isoform alpha-E preproprotein | OA | 0.950 | 0.718 | 7.96E-07 | | |
| 4503715 | fibrinogen, gamma chain isoform gamma-A precursor | OA | 1.000 | 0.744 | 1.43E-08 | | |
| 4557225 | alpha-2-macroglobulin | OA | 0.950 | 0.718 | 7.96E-07 | | |
| 4557325 | apolipoprotein E | OA | 1.000 | 0.744 | 1.43E-08 | | |
| 4557327 | apolipoprotein H (beta-2-glycoprotein I) | OA | 1.000 | 0.744 | 1.43E-08 | | |
| 4557385 | complement component 3 gel slice 3 | OA | 0.950 | 0.718 | 7.96E-07 | | |
| 4557385 | complement component 3 gel slice 5 | OA | 1.000 | 0.744 | 1.43E-08 | | |
| 4557485 | ceruloplasmin (ferroxidase) | OA | 0.950 | 0.718 | 7.96E-07 | | |
| 4826762 | haptoglobin | OA | 0.950 | 0.718 | 7.96E-07 | | |
| 9257232 | orosomucoid 1 | OA | 0.850 | 0.667 | 2.51E-04 | | |
| 32483410 | group-specific component (vitamin D binding protein) | OA | 1.000 | 0.744 | 1.43E-08 | | |
| 50345296 | complement component 4B preproprotein (NP_001002029) | OA | 1.000 | 0.744 | 1.43E-08 | | |
| 51476111 | PREDICTED: similar to Apolipoprotein A-I precursor (Apo-AI) (XP_496536) | OA | 0.950 | 0.718 | 7.96E-07 | | |
| 55743122 | retinol-binding protein 4, plasma precursor (NP_006735) | OA | 0.900 | 0.692 | 1.87E-05 | | |

Figure 14 alpha-2-macroglobulin
ceruloplasmin (ferroxidase)
albumin
group-specific component (vitamin D binding protein)
inter-alpha (globulin) inhibitor H4 (plasma Kallikrein-sensitive glycoprotein)
complement component 3
apolipoprotein E
fibrinogen, alpha chain isoform alpha-E preproprotein
apolipoprotein H (beta-2-glycoprotein I)
fibronectin 1 isoform 3 preproprotein
histidine-rich glycoprotein
inter-alpha (globulin) inhibitor H2

Figure 15

METHOD OF DIAGNOSING OSTEOARTHRITIS

RELATED APPLICATIONS

The present application is a Continuation-in-Part of co-pending International Application No. PCT/US06/23619 filed on Jun. 16, 2006, which itself claims priority to Provisional Application No. 60/692,040 filed on Jun. 17, 2005. Both the International and Provisional Applications, which are entitled "Protein Profile for Osteoarthritis", are incorporated herein by reference.

BACKGROUND OF THE INVENTION

Musculoskeletal conditions affect hundreds of millions of people around the world and this figure is expected to increase sharply due to the predicted doubling of the population over 50 by the year 2020 ("*The Global Burden of Disease. A Comprehensive Assessment of Mortality and Disability from Diseases, Injuries, and Risk Factors in* 1990 *and Projected to* 2020", C. J. L. Murray and A. D. Lopez (Eds.), 1996, Harvard University Press: Cambridge, Mass.). Musculoskeletal conditions give rise to enormous healthcare expenditures and loss of economic productivity, and therefore have a huge impact on society. In the U.S. alone, musculoskeletal conditions were estimated to have cost $214 billion in 1995 (A. Praemer et al., "*Musculoskeletal Conditions in the United States*", 2nd Ed., 1999, American Academy of Orthopaedic Surgeons: Rosemont, Ill.). At the start of this millennium, the United Nations declared the years 2000-2010 the "Bone and Joint Decade" in an attempt to highlight the growing impact orthopedic conditions will have on world health as life expectancy increases, and to promote research efforts with the goal of advancing the understanding of these conditions and developing improved, cost-effective treatments (http://www.bone-andjointdecade.org). While there are many types of musculoskeletal conditions, osteoarthritis is one of the most common chronic musculoskeletal disorders encountered by physicians throughout the world.

Osteoarthritis (OA) is a non-inflammatory joint disease, which is characterized by the breakdown of joint cartilage. It may affect one or more joints in the body, including those of the fingers, neck, shoulder, hips, knees, lower spine region, and feet. OA can cause pain and severely impair mobility and lower extremity function (E. Bagge et al., Age Ageing, 1992, 21: 160-167; D. Hamerman, Ann. Rheum. Dis., 1995, 54: 82-85; J. Jordan et al., J. Rheumatol., 1997, 24: 1344-1349; S. M. Ling and J. M. Bathon, J. Am. Geriatr. Soc., 1998, 46: 216-225), which can lead to disability and difficulty maintaining independence (A. A. Guccione et al., Am. J. Public Health, 1994, 84: 351-358; M. A Gignac et al., J. Gerontol. B: Psychol. Sci. Soc. Sci., 2000, 55: 362-372; M. C. Corti and C. Rignon, Aging Clin. Exp. Res., 2003, 15: 359-363). OA is associated with ageing: the prevalence of radiographic osteoarthritis is less than 1% in people under 30 years of age but, with increasing age, the prevalence rises sharply and was found to be approximately 80% in individuals over 65 (R. C. Lawrence et al., J. Rheumatol., 1989, 16: 427-441; E. Bagge and P. Brooks, Drugs Aging, 1995, 7: 176-183; N. J. Manek and N. E. Lane, Am. Fam. Physician., 2000, 61: 1795-1804). Despite being a condition that causes most problems to populations after retirement age, OA is also rated the highest cause of work loss in the U.S. and Europe. In addition to age, risk factors known to be associated with OA include obesity, traumatic injury and overuse due to sports or occupational stresses. However, the precise etiology of osteoarthritis is still unknown.

Currently, diagnosis of OA is typically based upon radiological examination as well as clinical observations including localized tenderness, use-related pain, bony or soft tissue swelling, joint instability, limited joint function, muscle spasm, and crepitus (i.e., cracking or grinding sensation). While the diagnosis of OA is often suggested on physical examination, radiographic evaluation is generally used to confirm the diagnosis or assess the severity of the disease. The radiographic hallmarks of OA include non-uniform joint space loss, osteophyte formation, cyst formation, and subchondral sclerosis. While these characteristic features are generally present in X-ray images of "severe" or "late" OA, patients with "early" OA may not show radiographic evidence of bony changes, joint space narrowing and/or osteophytosis, making the diagnosis unclear or difficult to establish. In the absence of a reliable diagnosis, physicians cannot intervene early in the course of the disease, i.e. before signs of joint destruction arise. Magnetic resonance imaging (MRI) is particularly useful for delineating articular cartilage morphology and composition, particularly in large joints such as the knee, and can reveal cartilage defects and thinning regions of the joint not visible with radiography (K. Ott and J. Montes-Lucero, Radiol. Technol., 2002, 74: 25-42; F. Eckstein and C. Glaser, Semin. Mucculoskelet. Radiol., 2004, 8: 329-353; G. A. Tung, Med. Health R. I., 2004, 87: 172-175). However, this imaging technique is not routinely performed in patients with OA unless other conditions such as meniscal tears or ligament injuries need to be eliminated for diagnosis purposes.

There is currently no cure for OA, and available osteoarthritis therapies are directed at the symptomatic relief of pain, and at improving and maintaining joint function. Furthermore, in the context of the recent withdrawals of COX-2 inhibitors, physicians are even more limited in their choice of treatments for OA. The demand for disease-modifying drugs for OA has grown considerably as awareness of the profound social and economic impact of this prevalent and debilitating disorder has become widespread. However, clinical trials of such drugs rely on the assessment of changes in joint space observed using plain X-rays (S. A. Mazzuca et al., Osteoarthritis and Cartilage, 1997, 5: 217-226). Since changes caused by articular cartilage loss are small (1-2 mm per year), a minimum of one year is required before sufficient changes have occurred to be detectable and, therefore, before a drug's efficacy can be assessed.

Clearly, there is a great need for biological markers of OA and OA progression. In particular, biomarkers that would allow reliable diagnosis and monitoring in the early stages of the disease and permit early intervention to potentially prevent pain and long-term disability are highly desirable. Also needed are biomarkers and design assay systems that could evaluate the efficacy of disease-modifying OA drugs in a time frame significantly shorter than the year currently required for assessment of radiological changes.

SUMMARY OF THE INVENTION

The present invention relates to the use of protein expression profiles with clinical relevance to osteoarthritis. In particular, the invention provides the identity of proteins, whose expression is correlated with OA, with different phases of advancement of the disease, and/or with different subtypes of OA. These protein expression profiles may be applied to the diagnosis and staging as well as defining subcategories of disease useful for prognostic purposes in OA. Compared to existing methods of diagnosis, the protein expression profiles disclosed herein constitute a more robust signature of OA and OA progression, and provide a more reliable basis for the selection of appropriate therapeutic regimens. The invention also relates to the screening of drugs that target these biomarkers, in particular for the development of new therapeutics for the treatment of OA.

In general, the invention involves the use of expression profiles of the marker proteins listed in FIGS. 1 through 7 for diagnosing osteoarthritis.

More specifically, the present invention provides methods for distinguishing two previously unrecognized subtypes of OA, subtype I and subtype II. Methods are provided that comprise steps of: providing a biological sample obtained from a subject to be tested; determining, in the biological sample, the level of expression of a one or more of polypeptides selected from the group consisting of proteins presented in FIG. 15 (i.e., alpha-2-macroglobulin, ceruloplasmin (ferroxidase), albumin, group-specific component (vitamin D binding protein), inter-alpha (globulin) inhibitor H4 (plasma Kallikrein-sensitive glycoprotein), complement component 3, apolipoprotein E, fibrinogen, alpha chain isoform alpha-E preproprotein, apolipoprotein H (beta-2-glycoprotein I), fibronectin 1 isoform 3 preproprotein, histidine-rich glycoprotein, inter-alpha (globulin) inhibitor H2), analogs and fragments thereof, to obtain a test protein expression profile; and based on the test protein expression obtained, providing an osteoarthritis diagnosis to the subject. In certain preferred embodiments, providing an osteoarthritis diagnosis to the subject comprises identifying osteoarthritis suffered by the subject as subtype I osteoarthritis or subtype II osteoarthritis.

In certain inventive methods, providing an osteoarthritis diagnosis to the subject comprises comparing the test protein expression profile to a control protein expression profile, wherein a difference between the test protein expression profile and the control protein expression profile is indicative of the subtype of osteoarthritis in the subject; and based on the comparison, identifying osteoarthritis in the subject as subtype I osteoarthritis or subtype II osteoarthritis.

In certain embodiments, the control protein expression profile is a subtype I osteoarthritis expression profile, and the difference is indicative of subtype II osteoarthritis. In such embodiments, the difference may be selected from the group consisting of an increase in the level of expression of one or more polypeptides selected from the group consisting of alpha-2-macroglobulin, ceruloplasmin (ferroxidase), albumin, group-specific component (vitamin D binding protein), inter-alpha (globulin) inhibitor H4 (plasma Kallikrein-sensitive glycoprotein), complement component 3, apolipoprotein E, fibrinogen, alpha chain isoform alpha-E preproprotein, apolipoprotein H (beta-2-glycoprotein I), inter-alpha (globulin) inhibitor H2, analogs and fragments thereof; a decrease in the level of expression of one or more polypeptides selected from the group consisting of fibronectin 1 isoform 3 preproprotein, histidine-rich glycoprotein, analogs and fragments thereof; and any combination thereof.

In other embodiments, the control protein expression profile is a subtype II osteoarthritis expression profile, and the difference is indicative of subtype I osteoarthritis. In such embodiments, the difference may be selected from the group consisting of a decrease in the level of expression of one or more polypeptides selected from the group consisting of alpha-2-macroglobulin, ceruloplasmin (ferroxidase), albumin, group-specific component (vitamin D binding protein), inter-alpha (globulin) inhibitor H4 (plasma Kallikrein-sensitive glycoprotein), complement component 3, apolipoprotein E, fibrinogen, alpha chain isoform alpha-E preproprotein, apolipoprotein H (beta-2-glycoprotein I), inter-alpha (globulin) inhibitor H2, analogs and fragments thereof; an increase in the level of expression of one or more polypeptides selected from the group consisting of, fibronectin 1 isoform 3 preproprotein, histidine-rich glycoprotein, analogs and fragments thereof; and any combination thereof.

In these methods, the biological sample can comprise a sample of blood or blood product, a sample of urine, a sample of joint fluid, a sample of saliva, or a sample of synovial fluid. In certain preferred embodiments, the biological sample comprises a sample of synovial fluid. Determination of the level of expression of one or more of polypeptides according to the present invention may comprise exposing the biological sample to at least one antibody specific for at least one of said polypeptides.

In certain embodiments, the subject is a human being, for example, a patient suspected of having osteoarthritis or a patient diagnosed with osteoarthritis but whose osteoarthritis subtype is unknown.

The inventive methods may further comprise a step of selecting a therapy for the subject based on the determination of the osteoarthritis subtype for the subject.

In yet another aspect, the present invention provides OA expression profile maps comprising expression level information for one or more of polypeptides selected from the group consisting of the proteins presented in FIG. 15, analogs and fragments thereof. The OA expression profile may comprise level information for at least one biological sample obtained from a healthy individual, an individual with subtype I osteoarthritis or an individual with subtype II osteoarthritis.

In still another aspect, the present invention provides kits for identifying osteoarthritis subtype in a subject. Inventive kits comprise at least one reagent that specifically detects expression levels of at least one biomarker selected from the group consisting of: polypeptides selected from the group consisting of the proteins presented in FIG. 15, analogs and fragments thereof, and nucleic acid molecules comprising polynucleotide sequences coding for polypeptides selected from the group consisting of the proteins presented in FIG. 15, analogs and fragments thereof; and instructions for using said kits for identifying osteoarthritis in a subject as subtype I osteoarthritis or subtype II osteoarthritis.

In certain embodiments, the reagent that specifically detects expression levels of at least one biomarker comprises an antibody that specifically binds to at least one the polypeptides. In other embodiments, the reagent comprises a nucleic acid probe complementary to a polynucleotide sequence coding for at least one of the polypeptides. For example, the nucleic acid probe may be a cDNA or an oligonucleotide, and, in certain embodiments, is immobilized on a substrate surface.

Kits of the present invention may further comprise instructions required by a regulatory agency (e.g., the United States Food and Drug Administration) for use in in vitro diagnostic products; one or more of: extraction buffer/reagents and protocol, amplification buffer/reagents and protocol, hybridization buffer/reagents and protocol, immunodetection buffer/reagents and protocol, and labeling buffer/reagents and protocol, and/or at least one OA expression profile map as described above.

These and other objects, advantages and features of the present invention will become apparent to those of ordinary skill in the art having read the following detailed description of the preferred embodiments.

BRIEF DESCRIPTION OF THE DRAWING

FIG. 1 shows a list of 26 proteins found to be up-regulated in synovial fluid samples of patients with early osteoarthritis compared to synovial fluid samples of normal individuals (p>0.001).

FIG. 2 shows a list of 27 proteins found to be up-regulated in synovial fluid samples of patients with late osteoarthritis compared to synovial fluid samples of normal individuals (p>0.001).

FIG. 3 shows a list of 13 proteins found to be up-regulated in synovial fluid samples of patients with late osteoarthritis compared to synovial fluid samples of patients with early osteoarthritis (p>0.05).

FIG. 4 shows a list of 10 proteins found to be down-regulated in synovial fluid samples of patients with early osteoarthritis compared to synovial fluid samples of normal individuals (p>0.001).

FIG. 5 shows a list of 6 proteins found to be down-regulated in synovial fluid samples of patients with late osteoarthritis compared to synovial fluid samples of normal individuals (p>0.001).

FIG. 6 shows a list of 6 proteins found to be down-regulated in synovial fluid samples of patients with late osteoarthritis compared to synovial fluid samples of patients with early osteoarthritis.

FIG. 7(A) shows a list of proteins found to discriminate between early osteoarthritis and normal/healthy samples or between late osteoarthritis and normal/healthy samples. FIG. 7(B) shows a list of proteins found to discriminate between early and late osteoarthritis.

FIG. 8 shows a list of candidate biomarkers for early osteoarthritis.

FIG. 9 shows a list of candidate biomarkers for late osteoarthritis.

FIG. 10 shows results obtained for the proteins listed in the Table presented on FIG. 7.

FIG. 13 shows a table summarizing results of a Supervised Wilcoxon's ranksum test, which returned 15 unique proteins with significant differential abundance between the Healthy and OA group (p<0.00001 and rank order within top 100 using PCA) (see Example 2).

FIG. 14 shows a table listing 19 proteins significantly abundant (protein area) across Control (N=20) and OA (N=39) group by Wilcoxon's ranksum test at $p<1\times10^{-6}$. Sensitivity and specificity for each protein are calculated with respect to the number of samples of each group having protein area above or below the median area across all samples. The significance of median area dichotomy and true group label is assessed by 2-sided Fisher's exact test.

FIG. 15 shows a table listing 12 proteins found to distinguish/differentiate between two subtypes of OA, subtype I and subtype II.

DEFINITIONS

Figure 11:
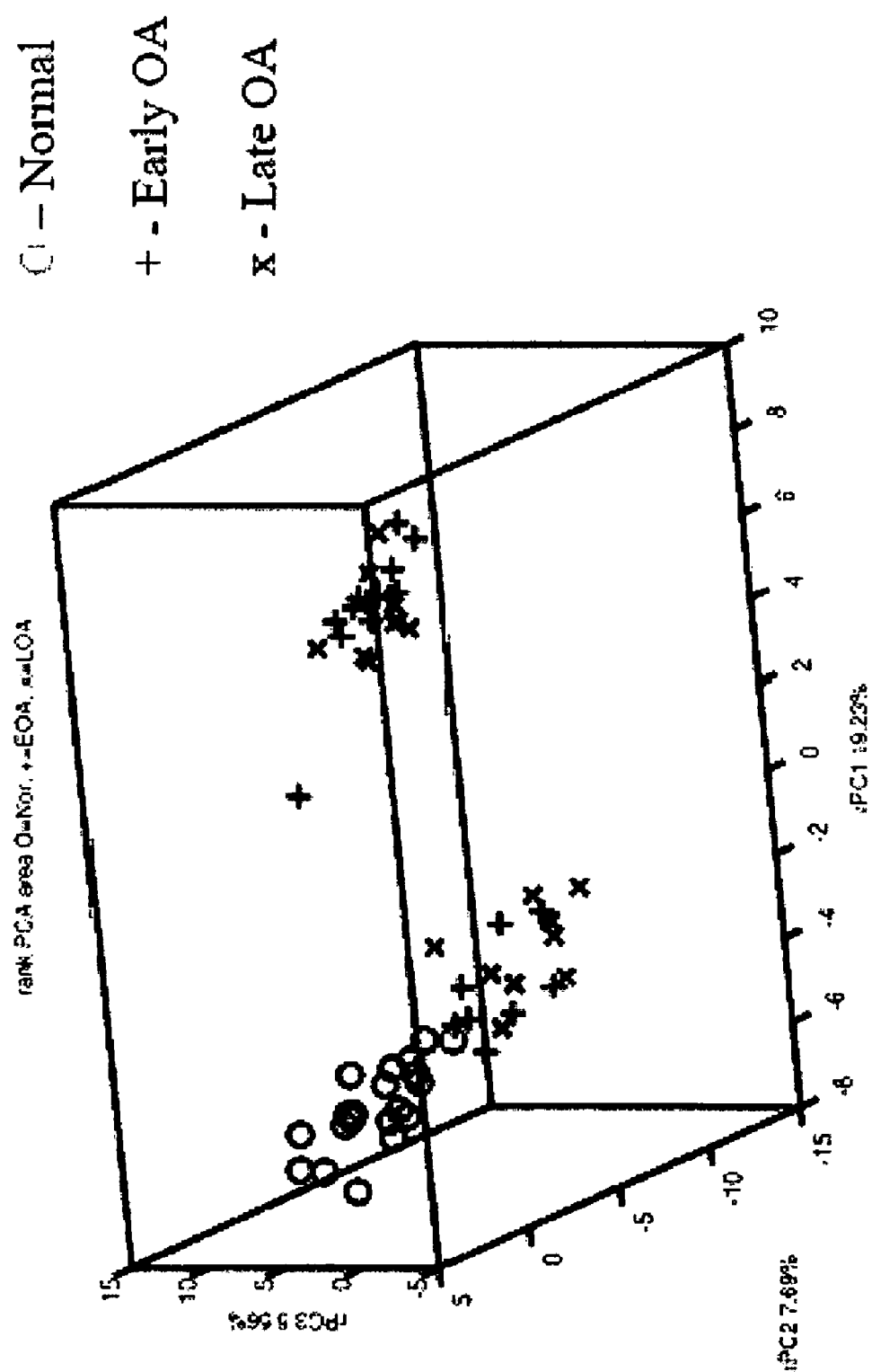
FIG. 11 is a graph showing the principal component analysis of all 342 protein spots (see Example 2). Differential expression of the protein profile for healthy subjects vs. late and early osteoarthritis is observed using this unsupervised analytical technique.

Throughout the specification, several terms are employed that are defined in the following paragraphs.

The term "subject", and "individual" are used herein interchangeably. They refer to a human or another mammal (e.g., primate, dog, cat, goat, horse, pig, mouse, rat, rabbit, and the like), that can be afflicted with osteoarthritis, but may or may not have the disease. In many embodiments, the subject is a human being.

The term "subject suspected of having OA" refers to a subject that presents one or more symptoms indicative of OA (e.g., joint pain, localized tenderness, bony or soft tissue swelling, joint instability, crepitus) or that is being screened for OA (e.g., during a routine physical examination). A subject suspected of having OA may also have one or more risk factors (e.g., age, obesity, traumatic injury, overuse due to sports or occupational stresses, family history). The term encompasses individuals who have not been tested for OA as well as individuals who have received an initial diagnosis (e.g., based on radiological examination) but for whom the stage of OA is not known, and/or for whom OA subtype is not known.

The terms "osteoarthritis stage" and "osteoarthritis phase" are used herein interchangeably and refer to the degree of advancement or progression of the disease. The present invention provides a means for determining the stage of the disease. In particular, the methods provided herein allows detection of "mild" or "early" OA, and of "severe" or "late" OA. Other staging systems known in the art include, for example, that developed by Marshall (W. Marshall, J. Rheumatol., 1996, 23: 582-584).

As used herein, the term "diagnosis" refers to a process aimed at determining if an individual is afflicted with a disease or ailment. In the context of the present invention, "diagnosis of OA" refers to a process aimed at one or more of: determining if an individual is afflicted with OA, identifying an OA subtype (i.e., subtype I or subtype II), and determining the stage of the disease (e.g., early OA or late OA).

The term "biological sample" is used herein in its broadest sense. A biological sample may be obtained from a subject (e.g., a human) or from components (e.g., tissues) of a subject. The sample may be of any biological tissue or fluid with which biomarkers of the present invention may be assayed. Frequently, the sample will be a "clinical sample", i.e., a sample derived from a patient. Such samples include, but are not limited to, bodily fluids which may or may not contain cells, e.g., blood, urine, synovial fluid, saliva, and joint fluid; tissue or fine needle biopsy samples, such as from bone or cartilage; and archival samples with known diagnosis, treatment and/or outcome history. Biological samples may also include sections of tissues such as frozen sections taken from histological purposes. The term biological sample also encompasses any material derived by processing the biological sample. Derived materials include, but are not limited to, cells (or their progeny) isolated from the sample, proteins or nucleic acid molecules extracted from the sample. Processing of the biological sample may involve one or more of: filtration, distillation, extraction, concentration, inactivation of interfering components, addition of reagents, and the like.

The terms "normal" and "healthy" are used herein interchangeably. They refer to an individual or group of individuals who have not shown any OA symptoms, including joint pain, and have not been diagnosed with cartilage injury or OA. Preferably, said normal individual (or group of individuals) is not on medication affecting OA and has not been diagnosed with any other disease. In certain embodiments, normal individuals have similar sex, age, body mass index as compared with the individual from which the sample to be tested was obtained. The term "normal" is also used herein to qualify a sample isolated from a healthy individual.

In the context of the present invention, the term "control sample" refers to one or more biological samples isolated from an individual or group of individuals that are normal (i.e., healthy). A control sample can also refer to a biological sample isolated from a patient or group of patients diagnosed with a specific OA subtype (i.e., subtype I or subtype II) or a specific stage of OA (e.g., early OA or late OA). The term "control sample" (or "control") can also refer to the compilation of data derived from samples of one or more individuals classified as normal, or one or more individuals diagnosed with OA, a specific OA subtype or a specific stage of OA, or one or more individuals having undergone treatment of OA.

The terms "OA biomarker" and "biomarker" are used herein interchangeably. They refer to a protein selected from the set of proteins provided by the present invention and whose expression profile was found to be indicative of OA and/or a particular stage of OA. The term "biomarker" also encompasses nucleic acid molecules comprising a nucleotide sequence which codes for a marker protein of the present invention as well as polynucleotides that hybridize with portions of these nucleic acid molecules.

As used herein, the term "indicative of OA", when applied to a biomarker, refers to an expression pattern or profile which is diagnostic of OA, OA subtype, or a stage of OA such that the expression pattern is found significantly more often in patients with the disease, disease subtype, or a stage of the disease than in patients without the disease or another subtype or stage of the disease (as determined using routine statistical methods setting confidence levels at a minimum of 95%). Preferably, an expression pattern which is indicative of OA is found in at least 60% of patients who have the disease and is found in less than 10% of subjects who do not have the disease. More preferably, an expression pattern which is indicative of OA is found in at least 70%, at least 75%, at least 80%, at least 85%, at least 90%, at least 95% or more in patients who have the disease and is found in less than 10%, less than 8%, less than 5%, less than 2.5%, or less than 1% of subjects who do not have the disease.

As used herein, the term "differentially expressed biomarker" refers to a biomarker whose level of expression is different in a subject (or a population of subjects) afflicted with OA relative to its level of expression in a healthy or normal subject (or a population of healthy or normal subjects). The term also encompasses a biomarker whose level of expression is different for a different disease subtype (i.e., OA subtype I and OA subtype II). The term further encompasses a biomarker whose level of expression is different at different stages of the disease (e.g., mild or early OA, severe or late OA). Differential expression includes quantitative, as well as qualitative, differences in the temporal or cellular expression pattern of the biomarker. As described in greater details below, a differentially expressed biomarker, alone or in combination with other differentially expressed biomarkers, is useful in a variety of different applications in diagnostic, staging, therapeutic, drug development and related areas. The expression patterns of the differentially expressed biomarkers disclosed herein can be described as a fingerprint or a signature of OA, OA subtype, OA stage and OA progression. They can be used as a point of reference to compare and characterize unknown samples and samples for which further information is sought.

The term "decreased level of expression", as used herein, refers to a decrease in expression of at least 10% or more, for example, 20%, 30%, 40%, or 50%, 60%, 70%, 80%, 90% or more, or a decrease in expression of greater than 1-fold, 2-fold, 3-fold, 4-fold, 5-fold, 10-fold, 50-fold, 100-fold or more as measured by one or more methods described herein. The term "increased level of expression", as used herein, refers to an increase in expression of at least 10% or more, for example, 20%, 30%, 40%, or 50%, 60%, 70%, 80%, 90% or more or an increase in expression of greater than 1-fold, 2-fold, 3-fold, 4-fold, 5-fold, 10-fold, 50-fold, 100-fold or more as measured by one or more methods, such as method described herein.

The terms "protein", "polypeptide", and "peptide" are used herein interchangeably, and refer to amino acid sequences of a variety of lengths, either in their neutral (uncharged) forms or as salts, and either unmodified or modified by glycosylation, side chain oxidation, or phosphorylation. In certain embodiments, the amino acid sequence is the full-length native protein. In other embodiments, the amino acid sequence is a smaller fragment of the full-length protein. In still other embodiments, the amino acid sequence is modified by additional substituents attached to the amino acid side chains, such as glycosyl units, lipids, or inorganic ions such as phosphates, as well as modifications relating to chemical conversion of the chains, such as oxidation of sulfhydryl groups. Thus, the term "protein" (or its equivalent terms) is intended to include the amino acid sequence of the full-length native protein, subject to those modifications that do not change its specific properties. In particular, the term "protein" encompasses protein isoforms, i.e., variants that are encoded by the same gene, but that differ in their pI or MW, or both. Such isoforms can differ in their amino acid sequence (e.g., as a result of alternative splicing or limited proteolysis), or in the alternative, may arise from differential post-translational modification (e.g., glycosylation, acylation, phosphorylation).

The term "protein analog", as used herein, refers to a polypeptide that possesses a similar or identical function as the full-length native protein but need not necessarily comprise an amino acid sequence that is similar or identical to the amino acid sequence of the protein, or possesses a structure that is similar or identical to that of the protein. Preferably, in the context of the present invention, a protein analog has an amino acid sequence that is at least 30% (more preferably, at least 35%, at least 40%, at least 45%, at least 50%, at least 55%, at least 60%, at least 65%, at least 70%, at least 75%, at least 80%, at least 85%, at least 90%, at least 95% or at least 99%) identical to the amino acid sequence of the full-length native protein.

The term "protein fragment", as used herein, refers to a polypeptide comprising an amino acid sequence of at least 5 amino acid residues (preferably, at least 10 amino acid residues, at least 15 amino acid residues, at least 20 amino acid residues, at least 25 amino acid residues, at least 40 amino acid residues, at least 50 amino acid residues, at least 60 amino acid residues, at least 70 amino acid residues, at least 80 amino acid residues, at least 90 amino acid residues, at least 100 amino acid residues, at least 125 amino acid residues, at least 150 amino acid residues, at least 175 amino acid residues, at least 200 amino acid residues, or at least 250 amino acid residues) of the amino acid sequence of a second polypeptide. The fragment of a marker protein may or may not possess a functional activity of the full-length native protein.

The terms "nucleic acid molecule" and "polynucleotide" are used herein interchangeably. They refer to a deoxyribonucleotide or ribonucleotide polymer in either single- or double-stranded form, and unless otherwise stated, encompass known analogs of natural nucleotides that can function in a similar manner as naturally occurring nucleotides. The terms encompass nucleic acid-like structures with synthetic backbones, as well as amplification products.

As used herein, the term "a reagent that specifically detects expression levels" refers to one or more reagents used to detect the expression level of one or more biomarkers (e.g., a polypeptide selected from the marker proteins provided herein, a nucleic acid molecule comprising a polynucleotide sequence coding for a marker protein, or a polynucleotide that hybridizes with at least a portion of the nucleic acid molecule). Examples of suitable reagents include, but are not limited to, antibodies capable of specifically binding to a marker protein of interest, nucleic acid probes capable of specifically hybridizing to a polynucleotide sequence of interest, or PCR primers capable of specifically amplifying a polynucleotide sequence of interest. The term "amplify" is used herein in the broad sense to mean creating/generating an amplification product. "Amplification", as used herein, generally refers to the process of producing multiple copies of a desired sequence, particularly those of a sample. A "copy" does not necessarily mean perfect sequence complementarity or identity to the template sequence.

The term "hybridizing" refers to the binding of two single stranded nucleic acids via complementary base pairing. The term "specific hybridization" refers to a process in which a nucleic acid molecule preferentially binds, duplexes, or hybridizes to a particular nucleic acid sequence under stringent conditions (e.g., in the presence of competitor nucleic acids with a lower degree of complementarity to the hybridizing strand). In certain embodiments of the present invention, these terms more specifically refer to a process in which a nucleic acid fragment (or segment) from a test sample preferentially binds to a particular probe and to a lesser extent or not at all, to other probes, for example, when these probes are immobilized on an array.

The terms "array", "micro-array", and "biochip" are used herein interchangeably. They refer to an arrangement, on a substrate surface, of hybridizable array elements, preferably, multiple nucleic acid molecules of known sequences. Each nucleic acid molecule is immobilized to a discrete spot (i.e., a defined location or assigned position) on the substrate surface. The term "micro-array" more specifically refers to an array that is miniaturized so as to require microscopic examination for visual evaluation.

The term "probe", as used herein, refers to a nucleic acid molecule of known sequence, which can be a short DNA sequence (i.e., an oligonucleotide), a PCR product, or mRNA isolate. Probes are specific DNA sequences to which nucleic acid fragments from a test sample are hybridized. Probes specifically bind to nucleic acids of complementary or substantially complementary sequence through one or more types of chemical bonds, usually through hydrogen bond formation.

The terms "labeled", "labeled with a detectable agent" and "labeled with a detectable moiety" are used herein interchangeably. These terms are used to specify that an entity (e.g., a probe) can be visualized, for example, following binding to an other entity (e.g., a polynucleotide or polypeptide). Preferably, the detectable agent or moiety is selected such that it generates a signal which can be measured and whose intensity is related to the amount of bound entity. In array-based methods, the detectable agent or moiety is also preferably selected such that it generates a localized signal, thereby allowing spatial resolution of the signal from each spot on the array. Methods for labeling polypeptides or polynucleotides are well-known in the art. Labeled polypeptides or polynucleotides can be prepared by incorporation of or conjugation to a label, that is directly or indirectly detectable by spectroscopic, photochemical, biochemical, immunochemical, electrical, optical, or chemical means. Suitable detectable agents include, but are not limited to, various ligands, radionuclides, fluorescent dyes, chemiluminescent agents, microparticles, enzymes, calorimetric labels, magnetic labels, and haptens. Detectable moieties can also be biological molecules such as molecular beacons and aptamer beacons.

The term "OA expression profile map" refers to a presentation of expression levels of a set of biomarkers in a particular status of OA (e.g., absence of disease, OA, subtype I OA, subtype II OA, early OA and late OA). The map may be presented as a graphical representation (e.g., on paper or a computer screen), a physical representation (e.g., a gel or array) or a digital representation stored in a computer-readable medium. Each map corresponds to a particular status of the disease (e.g., absence of disease, OA, subtype I OA, subtype II OA, early OA and late OA), and thus provides a template for comparison to a patient sample. In certain preferred embodiments, maps are generated from a plurality of samples obtained from a significant number of normal individuals or individuals with the same stage/status of OA. Maps may be established for individuals with matched age, sex and body mass index.

The term "computer readable medium" refers to any device or system for storing or providing information (e.g., data and instructions) to a computer processor. Examples of computer readable media include, but are not limited to, DVDs, CDs, hard disk drives, magnetic tape and servers for streaming media over networks.

The terms "compound" and "agent" are used herein interchangeably. They refer to any naturally occurring or non-naturally occurring (i.e., synthetic or recombinant) molecule, such as a biological macromolecule (e.g., nucleic acid, polypeptide or protein), organic or inorganic molecule, or an extract made from biological materials such as bacteria, plants, fungi, or animal (particularly mammalian, including human) cells or tissues. The compound may be a single molecule or a mixture or complex of at least two molecules.

The term "candidate compound" refers to a compound or agent (as defined above) that is to be tested for an activity of interest. In the screening methods of the present invention, candidate compounds are evaluated for their ability to modulate (e.g., increase or decrease) the expression level of one or more of the biomarkers provided herein. Particularly interesting are candidate compounds that can restore the expression profile of one or more disease-indicative biomarkers of a patient with OA to an expression profile more similar to that of an individual afflicted with an earlier stage of the disease or to that of a normal individual. Such compounds are potential "OA therapeutic agents".

As used herein, the term "effective amount" refers to an amount of a compound or agent that is sufficient to fulfill its intended purpose(s). In the context of the present invention, the purpose(s) may be, for example: to modulate the expression of at least one inventive biomarker; and/or to delay or prevent the onset of OA; and/or to slow down or stop the progression, aggravation, or deterioration of the symptoms of OA; and/or to bring about amelioration of the symptoms of OA, and/or to cure OA.

The term "system" and "biological system" are used herein interchangeably. A system may be any biological entity that can express or comprise at least one inventive biomarker. In the context of the present invention, in vitro, in vivo, and ex vivo systems are considered; and the system may be a cell, a biological fluid, a biological tissue, or an animal. For example, a system may originate from a living subject (e.g., it may be obtained by drawing blood, or by performing needle biopsy), or from a deceased subject (e.g., it may be obtained at autopsy).

A "pharmaceutical composition" is defined herein as comprising at least one compound of the invention (i.e., a candidate compound identified by an inventive screening method as a modulator of the expression of at least one inventive biomarker), and at least one pharmaceutically acceptable carrier.

As used herein, the term "pharmaceutically acceptable carrier" refers to a carrier medium which does not interfere with the effectiveness of the biological activity of the active ingredients and which is not excessively toxic to the host at the concentrations at which it is administered. The term includes solvents, dispersion media, coatings, antibacterial and antifungal agents, isotonic agents, absorption delaying agents, and the like. The use of such media and agents for pharmaceutically active substances is well known in the art (see, for example, Remington's Pharmaceutical Sciences, E. W. Martin, 18$^{th}$ Ed., 1990, Mack Publishing Co., Easton, Pa.).

The term "treatment" is used herein to characterize a method that is aimed at (1) delaying or preventing the onset of OA; or (2) slowing down or stopping the progression, aggravation, or deterioration of the symptoms of the condition; or (3) bringing about ameliorations of the symptoms of the condition; or (4) curing the condition. A treatment may be administered prior to the onset of the disease, for a prophylacetic or preventive action. It may also be administered after initiation of the disease, for a therapeutic action.

DETAILED DESCRIPTION OF CERTAIN PREFERRED EMBODIMENTS

As mentioned above, the present invention relates to improved systems and strategies for the diagnostic, characterization, and staging of OA. In particular, the present invention provides the identity of biomarkers whose expression has been found to correlate with OA, OA subtype, and OA progression.

I—Biomarkers

In one aspect, the present invention provides the identity of a set of proteins indicative of OA. As detailed in the Example Section, these proteins were identified using high-throughput proteomics technology.

Protein Markers. The protein markers provided herein are listed in the tables presented in FIGS. 1 through 7.

More specifically, by analyzing samples of synovial fluid obtained from healthy patients and from patients with early OA or late OA, the present Applicants have found that the proteins listed in FIG. 7(A) discriminate between normal/healthy and early OA and normal/healthy and late OA. They have also found that the proteins listed in FIG. 7(B) discriminate between early OA and late OA.

In addition, the present Applicants have found that samples of synovial fluid obtained from patients with early and late OA compared to samples of synovial fluid obtained from normal individuals exhibit an over-expression (i.e., increased expression levels) of the proteins listed in FIG. 1 and FIG. 2, respectively.

Similarly, the present Applicants have found that samples of synovial fluid obtained from patients with early OA and late OA compared to samples of synovial fluid obtained from normal individuals exhibit a lower expression (i.e., decreased levels of expression) of the proteins listed in FIG. 4 and FIG. 5, respectively.

Furthermore, the proteins listed in FIG. 3 have been found to exhibit increased levels of expression in synovial fluid samples from patients with late OA compared to synovial fluid samples obtained from patients with early OA; while the proteins listed in FIG. 7 have been found to exhibit decreased levels of expression in synovial fluid samples from patients with late OA compared to synovial fluid samples from patients with early OA.

The present Applicants have also found that 3 of the proteins listed in FIG. 14 (i.e., cystatin A, aggracan 1 and dermcidin) were significantly differentially abundant in healthy subjects, while the other proteins presented in FIG. 14 were significantly abundant in OA patients.

Therefore, the expression profiles of the proteins presented in FIGS. 1 through 7, and FIG. 14, can be used to diagnose OA as well as to determine the degree of advancement of the disease (i.e., to determine the stage of the disease).

In addition, the present Applicants have identified a set of 12 proteins (presented in FIG. 15) that allow distinction between two subtypes of OA (subtype I and subtype II) based on the relative expression of these proteins (e.g., in synovial fluid, see FIG. 16(A-L)). While it has long been known that there exist various phenotypes for patients with OA, molecular evidence to provide a mechanistic basis for this clinical observation was lacking until the present invention. The two OA subpopulations identified herein were not found to be segregated by age, gender, ethnicity, or number of medications taken. The inventive biomarkers differentiating OA subtypes can provide an accurate, highly reproducible means of identifying OA subsets and tracking response to therapy, thereby facilitating clinical trials and development of future therapies for patients with OA.

Nucleic Acid Markers Other OA biomarkers provided by the present invention include nucleic acid molecules comprising polynucleotide sequences coding for the inventive protein markers described above (or analogs and fragments thereof) and polynucleotides that hybridize with portions of these nucleic acid molecules.

OA Expression Profile Maps. Information on expression levels of a given set of biomarkers obtained using biological samples from individuals afflicted with a particular stage of the disease (e.g., healthy subjects, patients with OA, with subtype I OA, patients subtype II OA, with early OA, or with late OA) may be grouped to form an OA expression profile map. Preferably, an OA expression profile map results from the study of a large number of individuals with the same disease stage/status/subtype. In certain embodiments, an OA expression profile map is established using samples from individuals with matched age, sex, and body index. Each expression profile map provides a template for comparison to biomarker expression patterns generated from unknown biological samples. OA expression profile maps may be presented as a graphical representation (e.g., on paper or a computer screen), a physical representation (e.g., a gel or array) or a digital representation stored in a computer-readable medium.

II—Diagnosis Methods

As will be appreciated by those of ordinary skill in the art, sets of biomarkers whose expression profiles correlate with OA, can distinguish between different subtypes of OA and/or can discriminate between different stages of the disease may be used to identify, study or characterize unknown biological samples. Accordingly, the present invention provides methods for characterizing biological samples obtained from a subject suspected of having OA, for diagnosing OA in a subject, for identifying the subtype of OA, and for assessing the advancement of OA in a subject. In such methods, the biomarkers' expression levels determined for a biological sample obtained from the subject are compared to the levels in one or more control samples. The control samples may be obtained from a healthy individual (or a group of healthy individuals), from an individual (or group of individuals) afflicted with OA, from an individual (or group of individuals) afflicted with subtype I OA or subtype II OA, and/or from an individual (or group of individuals) afflicted with a specific stage of the disease (e.g., early OA or late OA). As mentioned above, the control expression levels of the biomarkers of interest are preferably determined from a significant number of individuals, and an average or mean is obtained. In certain preferred embodiments, the expression levels determined for the biological sample under investigation are compared to at least one expression profile map for OA, as described above.

Biological Samples

The methods of the invention may be applied to the study of any type of biological samples allowing one or more inventive biomarkers to be assayed. Examples of suitable biological samples include, but are not limited to, urine, blood, blood products, joint fluid, saliva, and synovial fluid. The biological samples used in the practice of the inventive methods of diagnostic may be fresh or frozen samples collected from a subject, or archival samples with known diagnosis, treatment and/or outcome history. Biological samples may be collected by any non-invasive means, such as, for example, by drawing blood from a subject, or using fine needle aspiration or needle biopsy. Alternatively, biological samples may be collected by an invasive method, including, for example, surgical biopsy.

In certain embodiments, the inventive methods are performed on the biological sample itself without or with limited processing of the sample.

In other embodiments, the inventive methods are performed at the single cell level (e.g., isolation of cells from the biological sample). However, in such embodiments, the inventive methods are preferably performed using a sample comprising many cells, where the assay is "averaging" expression over the entire collection of cells present in the sample. Preferably, there is enough of the biological sample to accurately and reliably determine the expression of the set of biomarkers of interest. Multiple biological samples may be taken from the same tissue/body part in order to obtain a representative sampling of the tissue.

In still other embodiments, the inventive methods are performed on a protein extract prepared from the biological sample. Preferably, the protein extract contains the total protein content. However, the methods may also be performed on extracts containing one or more of: membrane proteins, nuclear proteins, and cytosolic proteins. Methods of protein extraction are well known in the art (see, for example "*Protein Methods*", D. M. Bollag et al., $2^{nd}$ Ed., 1996, Wiley-Liss; "*Protein Purification Methods: A Practical Approach*", E. L. Harris and S. Angal (Eds.), 1989; "*Protein Purification Techniques: A Practical Approach*", S. Roe, $2^{nd}$ Ed., 2001, Oxford University Press; "*Principles and Reactions of Protein Extraction, Purification, and Characterization*", H. Ahmed, 2005, CRC Press: Boca Raton, Fla.). Numerous different and versatile kits can be used to extract proteins from bodily fluids and tissues, and are commercially available from, for example, BioRad Laboratories (Hercules, Calif.), BD Biosciences Clontech (Mountain View, Calif.), Chemicon International, Inc. (Temecula, Calif.), Calbiochem (San Diego, Calif.), Pierce Biotechnology (Rockford, Ill.), and Invitrogen Corp. (Carlsbad, Calif.). User Guides that describe in great detail the protocol to be followed are usually included in all these kits. Sensitivity, processing time and costs may be different from one kit to another. One of ordinary skill in the art can easily select the kit(s) most appropriate for a particular situation. After the protein extract has been obtained, the protein concentration of the extract is preferably standardized to a value being the same as that of the control sample in order to allow signals of the protein markers to be quantitated. Such standardization can be made using photometric or spectrometric methods or gel electrophoresis.

In yet other embodiments, the inventive methods are performed on nucleic acid molecules extracted from the biological sample. For example, RNA may be extracted from the sample before analysis. Methods of RNA extraction are well known in the art (see, for example, J. Sambrook et al., "*Molecular Cloning: A Laboratory Manual*", 1989, $2^{nd}$ Ed., Cold Spring Harbor Laboratory Press: Cold Spring Harbor, N.Y.). Most methods of RNA isolation from bodily fluids or tissues are based on the disruption of the tissue in the presence of protein denaturants to quickly and effectively inactivate RNases. Isolated total RNA may then be further purified from the protein contaminants and concentrated by selective ethanol precipitations, phenol/chloroform extractions followed by isopropanol precipitation or cesium chloride, lithium chloride or cesium trifluoroacetate gradient centrifugations. Kits are also available to extract RNA (i.e., total RNA or mRNA) from bodily fluids or tissues and are commercially available from, for example, Ambion, Inc. (Austin, Tex.), Amersham Biosciences (Piscataway, N.J.), BD Biosciences Clontech (Palo Alto, Calif.), BioRad Laboratories (Hercules, Calif.), GIBCO BRL (Gaithersburg, Md.), and Qiagen, Inc. (Valencia, Calif.).

In certain embodiments, after extraction, mRNA is amplified, and transcribed into cDNA, which can then serve as template for multiple rounds of transcription by the appropriate RNA polymerase. Amplification methods are well known in the art (see, for example, A. R. Kimmel and S. L. Berger, Methods Enzymol. 1987, 152: 307-316; J. Sambrook et al., "*Molecular Cloning: A Laboratory Manual*", 1989, $2^{nd}$ Ed., Cold Spring Harbour Laboratory Press: New York; "*Short Protocols in Molecular Biology*", F. M. Ausubel (Ed.), 2002, $5^{th}$ Ed., John Wiley & Sons; U.S. Pat. Nos. 4,683,195; 4,683,202 and 4,800,159). Reverse transcription reactions may be carried out using non-specific primers, such as an anchored oligo-dT primer, or random sequence primers, or using a target-specific primer complementary to the RNA for each probe being monitored, or using thermostable DNA polymerases (such as avian myeloblastosis virus reverse transcriptase or Moloney murine leukemia virus reverse transcriptase).

Determination of Protein Expression Levels

The diagnostic methods of the present invention generally involve the determination of expression levels of a plurality (i.e., one or more, e.g., at least 2, at least 3, at least 4, at least 5, at least 6, at least 7, at least 8, at least 9, at least 10 or more) of polypeptides in a biological sample obtained from a subject. Determination of protein expression levels in the practice of the inventive methods may be performed by any suitable method (see, for example, E. Harlow and A. Lane, "*Antibodies: A Laboratories Manual*", 1988, Cold Spring Harbor Laboratory: Cold Spring Harbor, N.Y.).

Binding Agents. In general, protein expression levels are determined by contacting a biological sample isolated from a subject with binding agents for one or more of the protein markers; detecting, in the sample, the levels of polypeptides that bind to the binding agents; and comparing the levels of polypeptides in the sample with the levels of polypeptides in a control sample. As used herein, the term "binding agent" refers to an entity such as a polypeptide or antibody that specifically binds to an inventive protein marker. An entity "specifically binds" to a polypeptide if it reacts/interacts at a detectable level with the polypeptide but does not react/interact detectably with peptides containing unrelated sequences or sequences of different polypeptides.

In certain embodiments, the binding agent is a ribosome, with or without a peptide component, an RNA molecule, or a polypeptide (e.g., a polypeptide that comprises a polypeptide sequence of a protein marker, a peptide variant thereof, or a non-peptide mimetic of such a sequence).

In other embodiments, the binding agent is an antibody specific for a protein marker of the invention. Suitable antibodies for use in the methods of the present invention include monoclonal and polyclonal antibodies, immunologically active fragments (e.g., Fab or $(Fab)_2$ fragments), antibody heavy chains, humanized antibodies, antibody light chains, and chimeric antibodies. Antibodies, including monoclonal and polyclonal antibodies, fragments and chimeras, may be prepared using methods known in the art (see, for example, R. G. Mage and E. Lamoyi, in "*Monoclonal Antibody Production Techniques and Applications*", 1987, Marcel Dekker, Inc.: New York, pp. 79-97; G. Kohler and C. Milstein, Nature, 1975, 256: 495-497; D. Kozbor et al., J. Immunol. Methods, 1985, 81: 31-42; and R. J. Cote et al., Proc. Natl. Acad. Sci. 1983, 80: 2026-203; R. A. Lerner, Nature, 1982, 299: 593-596; A. C. Nairn et al., Nature, 1982, 299: 734-736; A. J. Czernik et al., Methods Enzymol. 1991, 201: 264-283; A. J. Czernik et al., Neuromethods: Regulatory Protein Modification: Techniques & Protocols, 1997, 30: 219-250; A. J. Czernik et al., Neuroprotocols, 1995, 6: 56-61; H. Zhang et al., J. Biol. Chem. 2002, 277: 39379-39387; S. L. Morrison et al., Proc. Natl. Acad. Sci., 1984, 81: 6851-6855; M. S. Neuberger et al., Nature, 1984, 312: 604-608; S. Takeda et al., Nature, 1985, 314: 452-454). Antibodies to be used in the methods of the invention can be purified by methods well known in the art (see, for example, S. A. Minden, "*Monoclonal Antibody Purification*", 1996, IBC Biomedical Library Series: Southbridge, Mass.). For example, antibodies can be affinity-purified by passage over a column to which a protein marker or fragment thereof is bound. The bound antibodies can then be eluted from the column using a buffer with a high salt concentration.

Instead of being prepared, antibodies to be used in the methods of the present invention may be obtained from scientific or commercial sources.

Labeled Binding Agents. In certain embodiments, the binding agent is directly or indirectly labeled with a detectable moiety. The role of a detectable agent is to facilitate the detection step of the diagnostic method by allowing visualization of the complex formed by binding of the binding agent to the protein marker (or analog or fragment thereof). Preferably, the detectable agent is selected such that it generates a signal which can be measured and whose intensity is related (preferably proportional) to the amount of protein marker present in the sample being analyzed. Methods for labeling biological molecules such as polypeptides and antibodies are well-known in the art (see, for example, "*Affinity Techniques. Enzyme Purification. Part B*", Methods in Enzymol., 1974, Vol. 34, W. B. Jakoby and M. Wilneck (Eds.), Academic Press: New York, N.Y.; and M. Wilchek and E. A. Bayer, Anal. Biochem., 1988, 171: 1-32).

Any of a wide variety of detectable agents can be used in the practice of the present invention. Suitable detectable agents include, but are not limited to: various ligands, radionuclides, fluorescent dyes, chemiluminescent agents, microparticles (such as, for example, quantum dots, nanocrystals, phosphors and the like), enzymes (such as, for example, those used in an ELISA, i.e., horseradish peroxidase, beta-galactosidase, luciferase, alkaline phosphatase), colorimetric labels, magnetic labels, and biotin, dioxigenin or other haptens and proteins for which antisera or monoclonal antibodies are available.

In certain embodiments, the binding agents (e.g., antibodies) may be immobilized on a carrier or support (e.g., a bead, a magnetic particle, a latex particle, a microtiter plate well, a cuvette, or other reaction vessel). Examples of suitable carrier or support materials include agarose, cellulose, nitrocellulose, dextran, Sephadex, Sepharose, liposomes, carboxymethyl cellulose, polyacrylamides, polystyrene, gabbros, filter paper, magnetite, ion-exchange resin, plastic film, plastic tube, glass, polyamine-methyl vinyl-ether-maleic acid copolymer, amino acid copolymer, ethylene-maleic acid copolymer, nylon, silk, and the like. Binding agents may be indirectly immobilized using second binding agents specific for the first binding agents (e.g., mouse antibodies specific for the protein markers may be immobilized using sheep anti-mouse IgG Fc fragment specific antibody coated on the carrier or support).

Protein expression levels in the diagnostic methods of the present invention may be determined using immunoassays. Examples of such assays are radioimmunoassays, enzyme immunoassays (e.g., ELISA), immunofluorescence immunoprecipitation, latex agglutination, hemagglutination, and histochemical tests, which are conventional methods well-known in the art. As will be appreciated by one skilled in the art, the immunoassay may be competitive or non-competitive. Methods of detection and quantification of the signal generated by the complex formed by binding of the binding agent with the protein marker will depend on the nature of the assay and of the detectable moiety (e.g., fluorescent moiety).

Alternatively, the protein expression levels may be determined using mass spectrometry based methods or image (including use of labeled ligand) based methods known in the art for the detection of proteins. Other suitable methods include proteomics-based methods. Proteomics, which studies the global changes of protein expression in a sample, typically includes the following steps: (1) separation of individual proteins in a sample by electrophoresis (1-D PAGE), (2) identification of individual proteins recovered from the gel (e.g., by mass spectrometry or N-terminal sequencing), and (3) analysis of the data using bioinformatics.

Determination of Polynucleotide Expression Levels

As already mentioned above, the diagnostic methods of the present invention may involve determination of the expression levels of a set of nucleic acid molecules comprising polynucleotide sequences coding for an inventive protein marker. Determination of expression levels of nucleic acid molecules in the practice of the inventive methods may be performed by any suitable method, including, but not limited to, Southern analysis, Northern analysis, polymerase chain reaction (PCR) (see, for example, U.S. Pat. Nos. 4,683,195; 4,683,202, and 6,040,166; "*PCR Protocols: A Guide to Methods and Applications*", Innis et al. (Eds.), 1990, Academic Press: New York), reverse transcriptase PCR (RT-PCT), anchored PCR, competitive PCR (see, for example, U.S. Pat. No. 5,747,251), rapid amplification of cDNA ends (RACE) (see, for example, "Gene Cloning and Analysis: Current Innovations, 1997, pp. 99-115); ligase chain reaction (LCR) (see, for example, EP 01 320 308), one-sided PCR (Ohara et al., Proc. Natl. Acad. Sci., 1989, 86: 5673-5677), in situ hybridization, Taqman-based assays (Holland et al., Proc. Natl. Acad. Sci., 1991, 88: 7276-7280), differential display (see, for example, Liang et al., Nucl. Acid. Res., 1993, 21: 3269-3275) and other RNA fingerprinting techniques, nucleic acid sequence based amplification (NASBA) and other transcription based amplification systems (see, for example, U.S. Pat. Nos. 5,409,818 and 5,554,527), Qbeta Replicase, Strand Displacement Amplification (SDA), Repair Chain Reaction (RCR), nuclease protection assays, subtraction-based methods, Rapid-Scan™, and the like.

Nucleic acid probes for use in the detection of polynucleotide sequences in biological samples may be constructed using conventional methods known in the art. Suitable probes may be based on nucleic acid sequences encoding at least 5 sequential amino acids from regions of nucleic acids encoding a protein marker, and preferably comprise about 15 to about 50 nucleotides. A nucleic acid probe may be labeled with a detectable moiety, as mentioned above in the case of binding agents. The association between the nucleic acid probe and detectable moiety can be covalent or non-covalent. Detectable moieties can be attached directly to nucleic acid probes or indirectly through a linker (E. S. Mansfield et al., Mol. Cell. Probes, 1995, 9: 145-156). Methods for labeling nucleic acid molecules are well-known in the art (for a review of labeling protocols, label detection techniques and recent developments in the field, see, for example, L. J. Kricka, Ann. Clin. Biochem. 2002, 39: 114-129; R. P. van Gijlswijk et al., Expert Rev. Mol. Diagn. 2001, 1: 81-91; and S. Joos et al., J. Biotechnol. 1994, 35: 135-153).

Nucleic acid probes may be used in hybridization techniques to detect polynucleotides encoding the protein markers. The technique generally involves contacting and incubating nucleic acid molecules in a biological sample obtained from a subject with the nucleic acid probes under conditions such that specific hybridization takes place between the nucleic acid probes and the complementary sequences in the nucleic acid molecules. After incubation, the non-hybridized nucleic acids are removed, and the presence and amount of nucleic acids that have hybridized to the probes are detected and quantified.

Detection of nucleic acid molecules comprising polynucleotide sequences coding for a protein marker may involve amplification of specific polynucleotide sequences using an amplification method such as PCR, followed by analysis of the amplified molecules using techniques known in the art. Suitable primers can be routinely designed by one skilled in the art. In order to maximize hybridization under assay conditions, primers and probes employed in the methods of the invention generally have at least 60%, preferably at least 75% and more preferably at least 90% identity to a portion of nucleic acids encoding a protein marker.

Hybridization and amplification techniques described herein may be used to assay qualitative and quantitative aspects of expression of nucleic acid molecules comprising polynucleotide sequences coding for the inventive protein markers.

Alternatively, oligonucleotides or longer fragments derived from nucleic acids encoding each protein marker may be used as targets in a microarray. A number of different array configurations and methods of their production are known to those skilled in the art (see, for example, U.S. Pat. Nos. 5,445,934; 5,532,128; 5,556,752; 5,242,974; 5,384,261; 5,405,783; 5,412,087; 5,424,186; 5,429,807; 5,436,327; 5,472,672; 5,527,681; 5,529,756; 5,545,531; 5,554,501; 5,561,071; 5,571,639; 5,593,839; 5,599,695; 5,624,711; 5,658,734; and 5,700,637). Microarray technology allows for the measurement of the steady-state level of large numbers of polynucleotide sequences simultaneously. Microarrays currently in wide use include cDNA arrays and oligonucleotide arrays. Analyses using microarrays are generally based on measurements of the intensity of the signal received from a labeled probe used to detect a cDNA sequence from the sample that hybridizes to a nucleic acid probe immobilized at a known location on the microarray (see, for example, U.S. Pat. Nos. 6,004,755; 6,218,114; 6,218,122; and 6,271,002). Array-based gene expression methods are known in the art and have been described in numerous scientific publications as well as in patents (see, for example, M. Schena et al., Science, 1995, 270: 467-470; M. Schena et al., Proc. Natl. Acad. Sci. USA 1996, 93: 10614-10619; J. J. Chen et al., Genomics, 1998, 51: 313-324; U.S. Pat. Nos. 5,143,854; 5,445,934; 5,807,522; 5,837,832; 6,040,138; 6,045,996; 6,284,460; and 6,607,885).

OA Diagnosis and OA Staging

Once the expression levels of the biomarkers of interest have been determined (as described above) for the biological sample being analyzed, they are compared to the expression levels in one or more control samples or to at least one expression profile map for OA.

Comparison of expression levels according to methods of the present invention is preferably performed after the expression levels obtained have been corrected for both differences in the amount of sample assayed and variability in the quality of the sample used (e.g., amount of protein extracted, or amount and quality of mRNA tested). Correction may be carried out using different methods well-known in the art. For example, the protein concentration of a sample may be standardized using photometric or spectrometric methods or gel electrophoresis (as already mentioned above) before the sample is analyzed. In case of samples containing nucleic acid molecules, correction may be carried out by normalizing the levels against reference genes (e.g., housekeeping genes) in the same sample. Alternatively or additionally, normalization can be based on the mean or median signal (e.g., Ct in the case of RT-PCR) of all assayed genes or a large subset thereof (global normalization approach).

For a given set of biomarkers, comparison of an expression pattern obtained for a biological sample against an expression profile map established for a particular stage of OA may comprise comparison of the normalized expression levels on a biomarker-by-biomarker basis and/or comparison of ratios of expression levels within the set of biomarkers. In addition, the expression pattern obtained for the biological sample being analyzed may be compared against each of the expression profile maps (e.g., expression profile map for non-OA, expression profile map for OA, expression profile for subtype I OA, expression profile for subtype II OA, expression profile map for early OA, and expression profile map for late OA) or against an expression profile that defines delineations made based upon all the OA expression profile maps.

Selection of Appropriate Treatment

Using methods described herein, skilled physicians may select and prescribe treatments adapted to each individual patient based on the diagnosis and disease staging provided to the patient through determination of the expression levels of the inventive biomarkers. In particular, the present invention provides physicians with a non-subjective means to diagnose early OA, which will allow for early treatment, when intervention is likely to have its greatest effect, potentially preventing pain and long-term disability and improving patient's quality of life. Selection of an appropriate therapeutic regimen for a given patient may be made based solely on the diagnosis/staging provided by the inventive methods. Alternatively, the physician may also consider other clinical or pathological parameters used in existing methods to diagnose OA and assess its advancement.

Furthermore, the methods of OA diagnosis, OA subtype identification, and OA staging provided by the present invention allow the disease to be monitored even when signs of cartilage destruction would not be visible or when changes in joint spaces would not be detectable on X-ray images.

III—Kits

In another aspect, the present invention provides kits comprising materials useful for carrying out diagnostic methods according to the present invention. The diagnosis/characterization/staging procedures described herein may be performed by diagnostic laboratories, experimental laboratories, or practitioners. The invention provides kits which can be used in these different settings.

Materials and reagents for characterizing biological samples, diagnosing OA in a subject, identifying OA subtype, and/or staging OA in a subject according to the inventive methods may be assembled together in a kit. In certain embodiments, an inventive kit comprises at least one reagent that specifically detects expression levels of one or more inventive biomarkers, and instructions for using the kit according to a method of the invention. Each kit may preferably comprises the reagent which renders the procedure specific. Thus, for detecting/quantifying a protein marker (or an analog or fragment thereof), the reagent that specifically detects expression levels of the protein may be an antibody that specifically binds to the protein marker (or analog or fragment thereof). For detecting/quantifying a nucleic acid molecule comprising a polynucleotide sequence coding a protein marker, the reagent that specifically detects expression levels may be a nucleic acid probe complementary to the polynucleotide sequence (e.g., cDNA or an oligonucleotide). The nucleic acid probe may or may not be immobilized on a substrate surface (e.g., beads, a microarray, and the like).

Depending on the procedure, the kit may further comprise one or more of: extraction buffer and/or reagents, amplification buffer and/or reagents, hybridization buffer and/or reagents, immunodetection buffer and/or reagents, labeling buffer and/or reagents, and detection means. Protocols for using these buffers and reagents for performing different steps of the procedure may be included in the kit.

The reagents may be supplied in a solid (e.g., lyophilized) or liquid form. The kits of the present invention may optionally comprise different containers (e.g., vial, ampoule, test tube, flask or bottle) for each individual buffer and/or reagent. Each component will generally be suitable as aliquoted in its respective container or provided in a concentrated form. Other containers suitable for conducting certain steps of the disclosed methods may also be provided. The individual containers of the kit are preferably maintained in close confinement for commercial sale.

In certain embodiments, the kits of the present invention further comprise control samples. In other embodiments, the inventive kits comprise at least one expression profile map for OA, OA subtype, and/or OA progression as described herein for use as comparison template. Preferably, the expression profile map is digital information stored in a computer-readable medium.

Instructions for using the kit according to one or more methods of the invention may comprise instructions for processing the biological sample obtained from the subject and/or for performing the test, instructions for interpreting the results as well as a notice in the form prescribed by a governmental agency (e.g., FDA) regulating the manufacture, use or sale of pharmaceuticals or biological products.

IV—Screening of Candidate Compounds

As noted above, the inventive biomarkers whose expression profiles correlate with osteoarthritis, osteoarthritis subtype, and/or osteoarthritis progression are attractive targets for the identification of new therapeutic agents (e.g., using screens to detect compounds or substances that inhibit or enhance the expression of these biomarkers). Accordingly, the present invention provides methods for the identification of compounds potentially useful for treating osteoarthritis or modulating osteoarthritis progression.

The inventive methods comprise incubating a biological system, which expresses at least one inventive biomarker, with a candidate compound under conditions and for a time sufficient for the candidate compound to modulate the expression of the biomarker, thereby obtaining a test system; incubating the biological system under the same conditions and for the same time absent the candidate compound, thereby obtaining a control system; measuring the expression level of the biomarker in the test system; measuring the expression level of the biomarker in the control system; and determining that the candidate compound modulates the expression of the biomarker if the expression level measured in the test system is less than or greater than the expression level measured in the control system.

Biological Systems. The assay and screening methods of the present invention may be carried out using any type of biological systems, e.g., a cell or cells, a biological fluid, a biological tissue, or an animal. In certain embodiments, the methods are carried out using a system that can exhibit cartilage degeneration due to OA (e.g., an animal model, or whole or portion of a body part, e.g., the knee). In other embodiments, the methods are carried out using a biological entity that expresses or comprises at least one inventive biomarker (e.g., a cell or a sample of blood, urine, saliva, or synovial fluid).

In certain preferred embodiments, the assay and screening methods of the present invention are carried out using cells that can be grown in standard tissue culture plastic ware. Such cells include all appropriate normal and transformed cells derived from any recognized sources. Preferably, cells are of mammalian (human or animal, such as rodent or simian) origin. More preferably, cells are of human origin. Mammalian cells may be of any organ or tissue origin (e.g., bone, cartilage, or synovial fluid) and of any cell types as long as the cells express at least one inventive biomarker.

Cells to be used in the practice of the methods of the present invention may be primary cells, secondary cells, or immortalized cells (e.g., established cell lines). They may be prepared by techniques well known in the art (for example, cells may be isolated from bone, cartilage or synovial fluid) or purchased from immunological and microbiological commercial resources (for example, from the American Type Culture Collection, Manassas, Va.). Alternatively or additionally, cells may be genetically engineered to contain, for example, a gene of interest.

Selection of a particular cell type and/or cell line to perform an assay according to the present invention will be governed by several factors such as the nature of the biomarker whose expression is to be modulated and the intended purpose of the assay. For example, an assay developed for primary drug screening (i.e., first round(s) of screening) is preferably performed using established cell lines, which are commercially available and usually relatively easy to grow, while an assay to be used later in the drug development process is preferably performed using primary and secondary cells, which are generally more difficult to obtain, maintain and/or grow than immortalized cells but which represent better experimental models for in vivo situation.

Examples of established cell lines that can be used in the practice of the assay and screening methods of the present invention include fibroblastic and/or osseously derived cell lines. Primary and secondary cells that can be used in the inventive screening methods include, but are not limited to, chondrocytes and osteocytes.

Cells to be used in the inventive assays may be cultured according to standard cell culture techniques. For example, cells are often grown in a suitable vessel in a sterile environment at 37° C. in an incubator containing a humidified 95% air-5% $CO_2$ atmosphere. Vessels may contain stirred or stationary cultures. Various cell culture media may be used including media containing undefined biological fluids such as fetal calf serum. Cell culture techniques are well known in the art and established protocols are available for the culture of diverse cell types (see, for example, R. I. Freshney, "*Culture of Animal Cells: A Manual of Basic Technique*", $2^{nd}$ Edition, 1987, Alan R. Liss, Inc.).

In certain embodiments, the screening methods are performed using cells contained in a plurality of wells of a multi-well assay plate. Such assay plates are commercially available, for example, from Stratagene Corp. (La Jolla, Calif.) and Corning Inc. (Acton, Mass.) and include, for example, 48-well, 96-well, 384-well and 1536-well plates.

Candidate Compounds. As will be appreciated by those of ordinary skill in the art, any kind of compounds or agents can be tested using the inventive methods. A candidate compound may be a synthetic or natural compound; it may be a single molecule or a mixture or complex of different molecules. In certain embodiments, the inventive methods are used for testing one or more compounds. In other embodiments, the inventive methods are used for screening collections or libraries of compounds. As used herein, the term "collection" refers to any set of compounds, molecules or agents, while the term "library" refers to any set of compounds, molecules or agents that are structural analogs.

Collections of natural compounds in the form of bacterial, fungal, plant and animal extracts are available from, for example, Pan Laboratories (Bothell, Wash.) or MycoSearch (Durham, N.C.). Libraries of candidate compounds that can be screened using the methods of the present invention may be either prepared or purchased from a number of companies. Synthetic compound libraries are commercially available from, for example, Comgenex (Princeton, N.J.), Brandon Associates (Merrimack, N.H.), Microsource (New Milford, Conn.), and Aldrich (Milwaukee, Wis.). Libraries of candidate compounds have also been developed by and are commercially available from large chemical companies, including, for example, Merck, Glaxo Welcome, Bristol-Meyers-Squibb, Novartis, Monsanto/Searle, and Pharmacia UpJohn. Additionally, natural collections, synthetically produced libraries and compounds are readily modified through conventional chemical, physical, and biochemical means. Chemical libraries are relatively easy to prepare by traditional automated synthesis, PCR, cloning or proprietary synthetic methods (see, for example, S. H. DeWitt et al., Proc. Natl. Acad. Sci. U.S.A. 1993, 90:6909-6913; R. N. Zuckermann et al., J. Med. Chem. 1994, 37: 2678-2685; Carell et al., Angew. Chem. Int. Ed. Engl. 1994, 33: 2059-2060; P. L. Myers, Curr. Opin. Biotechnol. 1997, 8: 701-707).

Useful agents for the treatment of osteoarthritis may be found within a large variety of classes of chemicals, including heterocycles, peptides, saccharides, steroids, and the like. In certain embodiments, the screening methods of the invention are used for identifying compounds or agents that are small molecules (i.e., compounds or agents with a molecular weight <600-700 Da).

The screening of libraries according to the inventive methods will provide "hits" or "leads", i.e., compounds that possess a desired but not-optimized biological activity. The next step in the development of useful drug candidates is usually the analysis of the relationship between the chemical structure of a hit compound and its biological or pharmacological activity. Molecular structure and biological activity are correlated by observing the results of systemic structural modification on defined biological end-points. Structure-activity relationship information available from the first round of screening can then be used to generate small secondary libraries, which are subsequently screened for compounds with higher affinity. The process of performing synthetic modifications of a biologically active compound to fulfill all stereoelectronic, physicochemical, pharmacokinetic, and toxicologic factors required for clinical usefulness is called lead optimization.

Candidate compounds identified as potential OA therapeutic agents by screening methods of the present invention can similarly be subjected to a structure-activity relationship analysis, and chemically modified to provide improved drug candidates. The present invention also encompasses these improved drug candidates.

Identification and Characterization of OA Therapeutic Agents. In the screening methods of the present invention, a candidate compound is identified as a modulator of the expression of at least one inventive biomarker if the expression level of the biomarker in the test sample is lower or greater than the expression level of the same biomarker in the control sample.

Reproducibility of the results obtained using methods of the present invention may be tested by performing the analysis more than once with the same concentration of the same candidate compound (for example, by incubating cells in more than one well of an assay plate). Additionally, since candidate compounds may be effective at varying concentrations depending on the nature of the compound and the nature of its mechanism(s) of action, varying concentrations of the candidate compound may be tested (for example, by addition of different concentrations of the candidate compound in different wells containing cells in an assay plate). Generally, candidate compound concentrations from about 1 fM to about 10 mM are used for screening. Preferred screening concentrations are between about 10 pM and about 100 µM.

In certain embodiments, the methods of the invention further involve the use of one or more negative or positive control compounds. A positive control compound may be any molecule or agent that is known to modulate the expression of at least one biomarker studied in the screening assay. A negative control compound may be any molecule or agent that is known to have no detectable effects on the expression of at least one biomarker studied in the screening assay. In these embodiments, the inventive methods further comprise comparing the modulating effects of the candidate compound to the modulating effects (or absence thereof) of the positive (or negative) control compound.

As will be appreciated by those skilled in the art, it is generally desirable to further characterize the compounds identified by the inventive screening methods. For example, if a candidate compound has been identified as a modulator of the expression of a specific biomarker in a given cell culture system (e.g., an established cell line), it may be desirable to test this ability in a different cell culture system (e.g., primary or secondary cells). Alternatively or additionally, it may be desirable to evaluate the effects of the candidate compound on the expression of one or more other inventive biomarkers. It may also be desirable to perform pharmacokinetics and toxicology studies.

A candidate compound identified by the screening methods of the invention may also be further tested in assays that allow for the determination of the compound's properties in vivo. Suitable animal models of osteoarthritis are known in the art. In general, these models fall into two categories, spontaneous and induced (surgical instability or genetic manipulation). Animal models of naturally occurring OA occur in knee joints of guinea pigs, mice, and Syrian hamsters. Commonly used surgical instability models include medial meniscal tear in guinea pigs and rats, medial or lateral partial meniscectomy in rabbits, medial partial or total meniscectomy or anterior cruciate transection in dogs. Transgenic models have been developed in mice. Examples of animal models of osteoarthritis suitable for testing the candidate compounds identified as potential OA therapeutic agents include, but are not limited to, those described in M. J. Pond and G. Nuki, Ann. Rheum. Dis., 1973, 32: 387-388; T. Videman, Acta Orthop. Scand., 1982, 53: 339-347; S. B. Christensen, Scand. J. Rheumatol., 1983, 12: 343-349; A. M. Bendele et al., Vet. Pathol., 1987, 24: 436-443; K. D. Brandt et al., J. Rheumatol., 1991, 18: 436-446; K. D. Brandt, Ann. NY Acad. Sci., 1994, 732: 199-205; C. S. Carlson et al., J. Orthop. Res., 1994, 12: 331-339; A. G. Fam et al., Arthritis Rheum., 1995, 38: 201-210; K. W. Marshall and A. D. Chan, J. Rheumatol., 1996, 23: 344-350; H. J. Helminen et al., Rheumatol., 2002, 41: 848-856 and references cited therein; and J. L. Henry, Novartis Found Symp., 2004, 260: 139-145.

V—Pharmaceutical Compositions of Identified OA Therapeutic Agents

The present invention also provides pharmaceutical compositions, which comprise, as active ingredient, an effective amount of at least one compound identified by an inventive screening assay as a modulator of the expression of at least one biomarker or one set of biomarkers disclosed herein. The pharmaceutical composition may be formulated using conventional methods well known in the art. Such compositions include, in addition to the active ingredient(s), at least one pharmaceutically acceptable liquid, semi-liquid, or solid diluent acting as pharmaceutical vehicle, excipient or medium, and termed here "pharmaceutically acceptable carrier".

According to the present invention, an inventive pharmaceutical composition may include one or more OA therapeutic agents of the invention as active ingredients. Alternatively, a pharmaceutical composition containing an effective amount of one OA therapeutic agent may be administered to a patient simultaneously with or sequentially with a pharmaceutical composition containing a different inventive OA therapeutic agent.

In another embodiment of this invention, an inventive OA therapeutic agent, or a pharmaceutical composition thereof, may be administered serially or in combination with conventional therapeutics used in the treatment of OA. Such therapeutics include pain relievers such as acetaminophen; Non-steroidal Anti-inflammatory Drugs (NSAIDs), such as aspirin, ibuprofen, naproxen, and ketoprofen; COX-2 inhibitors; corticosteroids; combination of supplement glucosamine and chondroitin sulfates; and over the counter topical formulations containing capsaicin.

Alternatively or additionally, an inventive OA therapeutic agent, or a pharmaceutical composition thereof, may be administered serially or in combination with conventional therapeutic regimens for the treatment of osteoarthritis including viscosupplementation, surgery, arthroplasty (or joint replacement surgery), arthrodesis (or joint fusion), osteotomy, arthroscopy and cartilage transplantation VI—Methods of Treatment In another aspect, the present invention provides methods for the treatment and/or prevention of osteoarthritis. These methods comprise administering to a subject afflicted with OA, an effective amount of a compound that modulates the expression of at least one inventive biomarker. The compound may be known in the art to act as a modulator of the expression of the at least one biomarker. Alternatively, the compound may have been identified as an OA therapeutic agent by a screening method provided by the present invention.

Subject Selection. Subjects suitable to receive a treatment according to the present invention include individuals that have been diagnosed with OA using conventional methods (e.g., radiological examination, clinical observations) as well as individuals that have been diagnosed with OA using diagnostic methods provided herein. Suitable subjects may or may not have previously received traditional treatment for the condition.

Administration. A treatment according to the methods of the present invention may consist of a single dose or a plurality of doses over a period of time. An inventive OA therapeutic agent, or pharmaceutical composition thereof, may also be released from a depot form per treatment. The administration may be carried out in any convenient manner such as by injection (subcutaneous, intravenous, intramuscular, intraperitoneal, or the like), oral administration, topical administration, rectal administration, or sublingual administration.

Effective dosages and administration regimens can be readily determined by good medical practice and the clinical condition of the individual patient. The frequency of administration will depend on the pharmacokinetic parameters of the active ingredient(s) and the route of administration. The optimal pharmaceutical formulation can be determined depending upon the route of administration and desired dosage. Such formulations may influence the physical state, stability, rate of in vivo release, and rate of in vivo clearance of the administered compounds.

Depending on the route of administration, a suitable dose may be calculated according to body weight, body surface area, or organ size. Optimization of the appropriate dosage can readily be made by those skilled in the art in light of pharmacokinetic data observed in human clinical trials. The final dosage regimen will be determined by the attending physician, considering various factors which modify the action of drugs, e.g., the drug's specific activity, the severity of the damage and the responsiveness of the patient, the age, condition, body weight, sex and diet of the patient, the severity of any present infection, time of administration and other clinical factors. As studies are conducted, further information will emerge regarding the appropriate dosage levels and duration of treatment for various stages of advancement of OA.

EXAMPLES

The following examples describe some of the preferred modes of making and practicing the present invention. However, it should be understood that these examples are for illustrative purposes only and are not meant to limit the scope of the invention. Furthermore, unless the description in an Example is presented in the past tense, the text, like the rest of the specification, is not intended to suggest that experiments were actually performed or data were actually obtained.

Most of the results presented below have been reported by the present Applicants in two scientific publications (R. Gobezie et al., "Proteomics: Applications to the Study of Rheumatoid Arthritis and Osteoarthritis", J. Am. Orthop. Surg., 2006, 14: 325-332 and R. Gobezie et al. "High Abundance Synovial Fluid Proteome: Distinct Profiles in Health and Osteoarthritis", which was submitted to Arthritis & Rheumatism). Each scientific publication is incorporated herein by reference in its entirety.

Example 1

Identification of Marker Proteins by Proteomics

Overview

Recent studies have just begun to explore the power of mass spectroscopy to characterize the proteomes of complex protein fluids including serum, tissue and synovial fluid. However, application of this technology to the study of OA and RA has been very limited. The project undertaken by the present Applicants employs this technology to characterize the proteomes of synovial fluid from shoulders and knees in at least four patient populations: patients with early OA, patients with end-stage OA (or late OA), patients with early RA, and patients with end-stage RA (or late RA). The goal is to determine quantitative protein profiles specific for these diseases during each of these disease states in an effort to identify a distinct protein profile for OA and RA and find plausible etiologic candidate proteins for these diseases.

Site of Study

Samples for this study were collected at both the Brigham and Women's and Massachusetts General Hospital. The collective practice in orthopaedic surgery at these two hospitals allows numerous and extensive exposure to study subjects with both RA and OA throughout the course of these diseases. Internal Review Board approval from the Partners Human Studies Office has been obtained in order to conduct this study at both hospitals.

Furthermore, a collaboration with the Harvard Partners Center for Genomics and Genetics (HPCGG) in Cambridge, Mass. was established in order to recruit their expertise with the protein separation and processing of the samples using LC-MS/MS. The HPCGG is a state-of-the-art facility and is the result of collaboration between Harvard Medical School, Partners Healthcare Inc., and numerous pharmaceutical companies, whose mission is to provide access to and expertise in genomics and proteomics technology to clinicians and scientists.

Studied Individuals

This pilot study focused on 15 study subjects from each of the four disease groups, namely: early OA, early RA, late OA and late RA and twenty subjects that are healthy volunteers meeting the inclusion and exclusion criteria below.

Statistical Analysis

A sample size of 60 knee patients (early OA, early RA, late OA, late RA; 15 per group) and 20 non-arthritic knee controls will provide 90% statistical power ($\alpha=0.001$, $\beta=0.10$) to detect significant group differences with respect to identified proteins from mass spectroscopy using analysis of variance (ANOVA) with the Bonferroni procedures for multiple comparisons and a two-tailed $\alpha$-level (version 5.0, nQuery Advisor, Statistical Solutions, Boston, Mass.).

Preliminary Study

The first goal of the preliminary study was to determine the protein profiles in synovial fluid from knee joints with early and late primary idiopathic OA as compared to non-arthritic knee controls using LC-MS/MS.

Hypothesis: Protein profiles from synovial fluid of knee joints with late OA will differ from both those of early OA and non-arthritic controls.

Rationale: Prior work has shown that characterization of proteins from various stages in the development of OA differ during the course of disease. Since proteins are the functional units of genomic expression, the etiologic entities effecting disease and the mediators of cellular response are likely to differ in quantity, identity or both as disease severity progresses. Furthermore, since non-arthritic synovial fluid presumably does not contain the proteins effecting OA, the candidate proteins suspected as potential etiologic agents in this disease should not be present in the non-arthritic joint fluid.

Approach: The selection of patients in the control group as well as the early and late OA study groups was performed based on the Kellgren and Lawrence Grading System for the diagnosis of OA. No patients with complicated medical histories including diabetes, other inflammatory disorders, intra-articular fracture or steroid injection in the prior 3 months, infection, blood dyscrasias or cancer were included in any of the study groups for this project. In addition, patients included in this arm of the study have not been on NSAID therapy for 4 weeks prior to collection of synovial fluid. Patients with a history of rheumatoid arthritis were excluded from the study arm pertaining to the first goal of this project.

Normal volunteers that meet specific inclusion and exclusion criteria were solicited from within the Applicants' institutions for participation in this study as negative controls using an IRB approved protocol. These patients were less than 35 years of age and had no history of serious knee trauma, inflammatory disorders, corticosteroid use, blood dyscrasias, cancer or thrombocytopenia. The age cut-off was determined arbitrarily to minimize the possibility of including patients with sub-clinical OA including those progressing towards OA on a molecular level that may not have visible evidence of chondromalacia. Each member of this control group had a clinical history documented, an X-ray evaluation of the involved knee (AP/lateral/sunrise views), and an arthrocentesis performed in the outpatient clinic areas in the Applicants' institutions. Synovial fluid collected during the arthrocentesis was snap frozen immediately in liquid nitrogen and stored at $-135°$.

The early OA group was selected from amongst a large pool of patients presenting for elective arthroscopic knee surgery for meniscal tear debridement to the Applicants' Department. The synovial fluid from these joints was collected as 'discarded tissue' with an IRB approved protocol at the time of their surgery and snap frozen in liquid nitrogen immediately and stored at $-135°$. In the late OA group, the synovial fluid was collected and processed in a similar fashion from amongst patients selected in a consecutive series from a similarly large population of study subjects that have been diagnosed with primary idiopathic osteoarthritis and are presenting for primary total knee (TKR) replacement at our institutions.

Non-arthritic controls were analyzed simultaneously with the early and late OA samples to minimize random errors. Following LC-MS/MS analysis, the ICAT procedure for quantification of candidate proteins was performed as described in the Methods below.

Methods: Sample Preparation: One (1) mL of synovial fluid from each subject was normalized to total protein concentration with a microBCA test and diluted in 6 M urea, 100 mM ammonium bicarbonate, 1% SDS, disulfide bonds were reduced with DTT, and resulting free thiols, alkylated with iodoacetamide. The sample was diluted 8 fold, and trypsin added to a substrate to enzyme ratio of 100:1. The digest was quenched with formic acid, and the hyaluronic acid, urea and SDS removed on a Sepharose FF SP column. The eluate from this column was lyophilized and fractionated via strong cation exchange on an Amersham AKTA explorer HPLC workstation. Peptides were separated out on Mono S 5/5, with a gradient of ammonium formate into 30 peptide containing fractions. The fractions were lyophilized and resuspended in 100 µL of 5% acetonitrile 0.1% formic acid/water, and a mixture of internal peptide standards added.

LC-MS/MS: For the first run, 75 µL of this preparation was injected onto a custom packed 250 cm×30 cm C18 silica packed capillary HPLC column and eluted over a 2.5 hour gradient into a ThermoFinnigan LCQ Deca XP plus ion trap MS via a microspray interface. A second MS run was performed on samples that showed the presence of low abundance peptides from the first microspray run. For these low level peptide fractions, 10 µL of the same fraction was injected onto a 75 cm×15 cm C18 silica packed column with a segmented exclusion list of already identified masses from the first microspray run, and separated over 4 hours.

Analysis: LC-MS/MS: Raw data were processed to peptides using Bioworks (ThermoFinnigan), and Searched against the Non-redundant protein database (NCBI) using Sequest (University of Washington). Unmatched peptide fragments were remanded to sequential searches of the same database using mass shifts for common peptide modification. Any remaining peptides that have high MS/MS ion counts and fail to "hit" any of the proteins in the database were selected and submitted to De NovoX (ThermoFinnigan). Fragment patterns that generate sequence tags of greater than 6 amino acids with greater than 99% confidence were submitted for blast database searching. This iterative approach saved processing time and prevents dilution of the significance of the previous hits.

Results were scored for XCorr values greater than 1.8 for +1, 2.5 for +2, and 3.0 for +3 charged peptides, with an RSP of 1. Resultant peptides were analyzed in Bioworks and relative peak areas calculated using the built in area calculator. ICAT labeled peptides were analyzed using Express. Peptides with a calculated average peptide area ratio difference of greater than 25% were isolated and passed on for further analysis.

Principle Component Analysis (PCA) and Wilcoxon Rank Sum Tests were used to analyze the data and identify plausible biomarkers with p<0.001.

Example 2

Identification of Highly Sensitive and Specific Candidate Protein Biomarkers

Methods

The experimental design for this study involved differential protein profiling of knee synovial fluid using LC-MS/MS from 20 healthy subjects [without OA] against two cohorts of 21 patients each diagnosed with early and late OA, respectively. All samples for this study were collected from subjects within our tertiary care referral center. The Applicants' institution's Internal Review Board approved all aspects of this study. All synovial fluid samples included in this study were snap-frozen in liquid nitrogen immediately after acquisition from the knee joint.

Healthy subjects. Twenty (20) subjects without any history of knee trauma, chronic knee pain, prior knee surgery, blood dyscrasias, cancer, chondrocalcinosis, corticosteroid injection, or NSAID use in the preceding 8 weeks were recruited for plain anterior-posterior, lateral and sunrise view x-rays of their right/left knee. A total of seventy-eight (78) subjects qualified for entry into the study based on these criteria. An arthrocentesis was attempted on each of these patients in order to obtain the twenty samples required for the study design. Samples that were free of blood contamination and consisted of a minimum of 500 µL were included in the study.

Early OA subjects. Samples were procured from twenty-one (21) patients presenting for elective arthroscopic debridement of an inner-third tear of the medial meniscus with a minimum age of 45 years. The inner-third meniscal tears are relatively avascular, and, therefore, are least likely to generate an inflammatory response that might confound protein expression related expressly to OA during proteomic analysis. No subjects with prior history of clinically significant knee trauma or infection, surgery, blood dyscrasia, cancer, corticosteroid injection or chondrocalcinosis were included in our study. As a result of their meniscal tear, prior NSAID use was not a plausible exclusion criterion. The diagnosis of early OA was made at the time of arthroscopy by the presence of arthroscopically visible chondral erosion. Synovial fluid was acquired at the time of arthroscopic trocar placement so as to avoid blood contamination of the samples.

Late OA subjects. One synovial fluid sample was procured from each of twenty-one (21) patients presenting for elective total knee replacement for the diagnosis of primary idiopathic osteoarthritis. The exclusion criteria were identical to those above. Each patient had documented erosion of all three compartments of the knee on plain radiographs. The synovial fluid was acquired from the knee joint prior to arthrotomy so as to avoid blood contamination.

Power analysis. Supervised pairwise-comparisons were performed between the three disease classes ($n_{Nor}$=20, $n_{EOA}$=21, $n_{LOA}$=18). Here, in the least optimal two class comparison scenario, two disease classes of sample sizes 18 and 20, respectively, possess a minimal statistical power of 80% at 0.05 level of significance (alpha) for detecting a 50% relative difference in the presence/abundance of a tested protein biomarker between the classes. The null hypothesis being that there is no difference in the tested biomarker presence in the two classes.

Reduction/Alkylation of Synovial Fluid Samples and Electropheresis. Each sample was reduced and alkylated in a lysis buffer prior to being subjected to electrophoresis. Each sample was fractionated into 9 molecular weight regions. An in-gel tryptic digestion was performed on the 9 slices from each sample. After 24 hours of tryptic digestion, the peptides were extracted and lyophilized to dryness. The lyophilate was redissolved into a loading buffer for mass spectrometry.

Mass Spectrometry. Samples are run on a LCQ DECA XP plus Proteome X workstation from Thermo-Finnigan. For each run (2.5 hrs.), half of each sample was separated on a 75 µm i.d.×18 cm column packed with C18 media. In between each sample a standard of a 5 Angio mix peptides (Michrom BioResources) to ascertain column performance, and observe any potential carryover that might have occurred. The LCQ is run in a top five configuration, with one MS scans and five MS/MS scans.

Processing of Mass Spectrometry Data.

There were 62 human subjects (20 healthy subjects (N), 21 with early osteoarthritis (EOA), and 21 with late osteoarthritis (LOA). Clinical parameters for each human subject are detailed above.

Spectra were searched against human RefSeqHuman (ftp-.ncbi.nih.gov) with the addition of contaminants using SEQUEST. Variable modifications for oxidized methione and carboxyamidomethylated cysteine were permitted. Data was filtered using the following criteria (1) Xcorr greater than or equal to 1.5, 2.5 and 3.0 for a charge state 1, 2 and 3 respectively, (2) a ΔCn of greater than 0.1 and (3) an RSp equal to 1. All peptides passing these criterions were then mapped back to all human protein sequences in RefSeq with a string search for exact matches. For each gene, for each slice a minimal (duplicates removed) set of peptides was determined. This list was sorted by the total number of peptides in descending order. The first peptide array in this list was defined as a cluster and compared pair wise to every other array in the list by determining whether the N-1 comparison was an equal or a proper subset. If the peptide array was determined to be an equal or proper subset, it was added to the cluster and removed from list. The process was repeated until all comparisons were exhausted. For each cluster, the gene with the greatest number peptides elements was assigned to designate the cluster. If multiple genes within the cluster had the same number of peptides, an arbitrary member was assigned as representative of the cluster. Peptides shared between clusters were identified and removed from further analysis.

Peptide area was calculated using the area function in BioWorks 3.1 (Thermo Electron Corporation) with scan window of 60. Gene area was calculated as the sum of the areas for each independent analyte for all unique peptides within a cluster. If multiple areas were identified for a given analyte, the largest area was selected and used in the area calculation. An independent analyte is defined as unique mass to charge identified in the SEQUEST search passing the filtering criterion.

One hundred thirty-five (135) proteins with unique GenInfo accession numbers (GI#) were identified by LC/MS/MS for all 62 human samples with each sample divided into 9 protein gel slices. Note that if one counted two proteins with the same GI# that were detected in distinct gel slices as separate protein elements, then there are 342 such gel-centric protein elements. It is reasonable to consider this gel-centric counting scheme since one protein (with its unique GI#) could be degraded during a biological process into distinct peptide sequences that are detected by LC/MS/MS in distinct gel slices. Two measures of abundance were considered for each detected peptide/protein in each gel slice: Area and Coverage. Area, the primary measure of abundance in this study, is a non-negative real number referring to the sum of the areas for each independent analyte for all unique peptides within a cluster. Analyte area was calculated using the area function in BioWorks 3.1 (Thermo Electron Corporation) with scan window of 60. If multiple areas were identified for a given analyte, the largest area was selected and used in the area calculation. An independent analyte is defined as unique mass to charge identified in the SEQUEST search passing the filtering criterion. Coverage, the secondary measure of abundance, is a non-negative area number referring to the number of unique non-overlapping peptide residues that can be mapped to a given gene divided by the length of the gene—the same peptide is often sequenced multiple times and the searches were allowed to identify peptides with internal tryptic cleavage sites. The dataset may be expressed as an algebraic matrix of 342 gel-centric protein elements×62 human samples, whose entries are either Area or Coverage.

Principal component analysis. Principal component analysis (PCA) was used to assess the dominant global sample variations between all 62 samples and 342-protein profiles, and to summarize the dataset in terms of a reduced number of dominant features that most affect the global sample variation (O. Alter et al., Proc Natl Acad Sci USA, 2000, 97: 10101-10106; A. T. Kho et al., Genes Dev., 2004, 18: 629-640; J. Misra et al., Genome Res., 2002, 12: 1112-1120). With Area as a measure of gel-centric protein abundance, the first three PC's alone capture 98.33% of global sample variation.

Wilcoxon's ranksum test. For each protein, non-parametric Wilcoxon's ranksum test was used to test the null hypothesis that its abundance measurements (Area or Coverage) from any two distinct human disease conditions—N, EOA, or LOA—derive from a common distribution. The null hypothesis was rejected for p<0.000001, i.e., when p<0.000001, that particular protein was differentially abundant between the two disease conditions.

Results

Proteomic profile relationship between samples. The proteomic profile relationship between all 62 human synovial samples was investigated. Each sample was represented as a 342-gel-centric protein profile. The entire dataset was a matrix of 342-proteins×62 human samples, with the Area-based measure of abundance as entries.

Using PCA on all 62 human samples, 3 LOA sample profiles were observed to be statistical outliers from the remaining 59 (data not shown). These 3 outliers were removed from subsequent data analyses, leaving the dataset under consideration as 342-proteins×59 human samples. PCA of this data in the two maximal and important directions of sample variance—principal component 1 (PC1) and 2 (PC2), accounting for 90.35% of total sample variance—is shown in FIG. 3. Healthy subject profiles (n=20) were observed to be proteomically more homogeneous than the EOA (n=21) and LOA (n=19) profiles. The direction of maximal variance PC1 appeared to be correlated with the disease state. Remarkably, this unsupervised analysis showed no definitive distinction between EOA and LOA at the 342-protein profile level.

Differentially abundant proteins in Healthy versus OA proteomic profiles. Proteins, which were differentially abundant (by Area measures) between the Healthy and OA groups, were then investigated here. OA refers to the combined EOA and LOA samples, minus 3 LOA outliers. This EOA-LOA consolidation is justified by the foregoing unsupervised PCA showing a lack of distinction between global EOA and LOA proteomic profiles.

Figure 12:
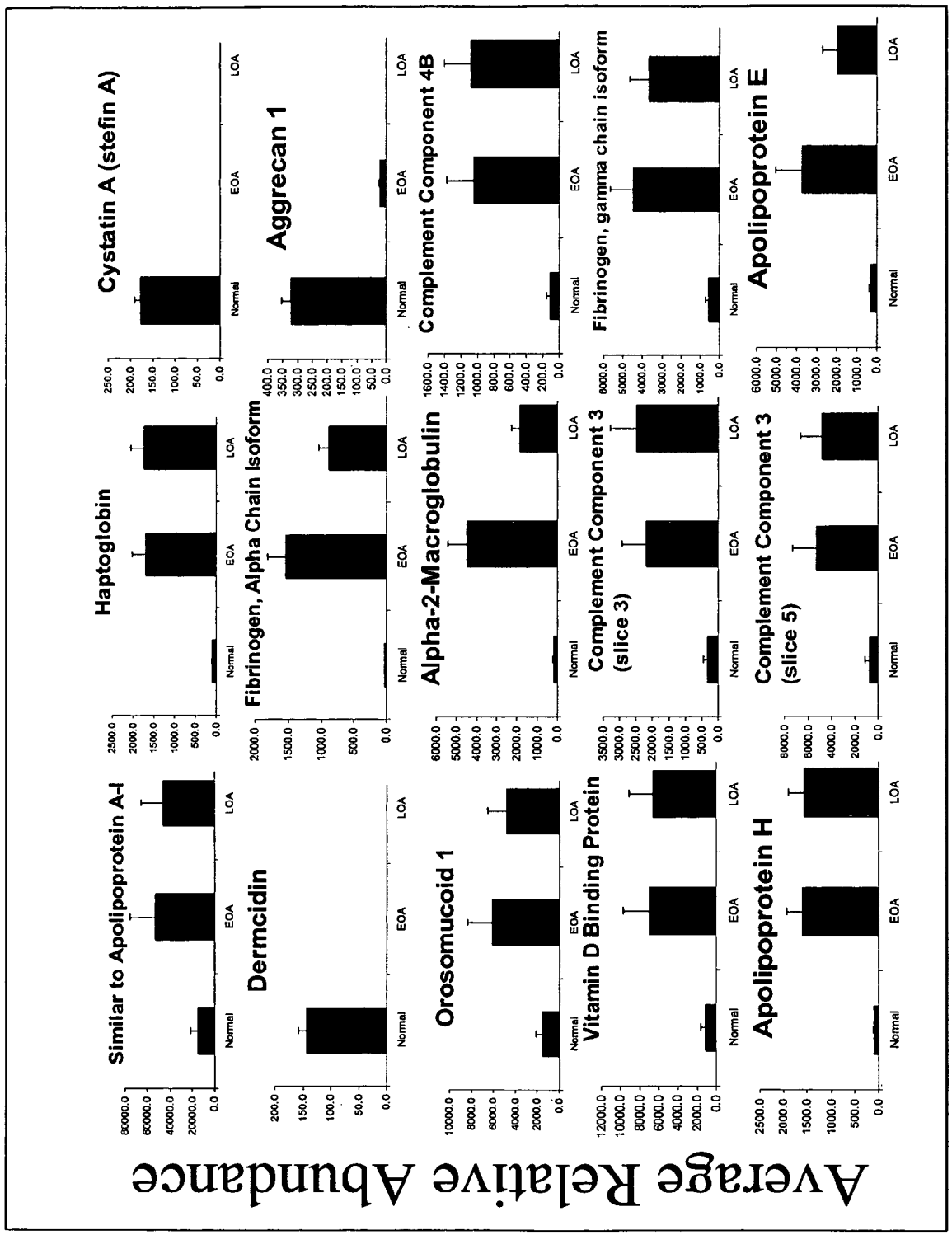
FIG. 12 is a graph showing results of the relative quantitation of biomarkers using total ion current data from mass spectrometry (see Example 2). Determining cutoff values between controls and 'diseased' cohorts is one of the necessary criterion towards the establishment of protein or gene targets as 'biomarkers'.
Figure 16A:
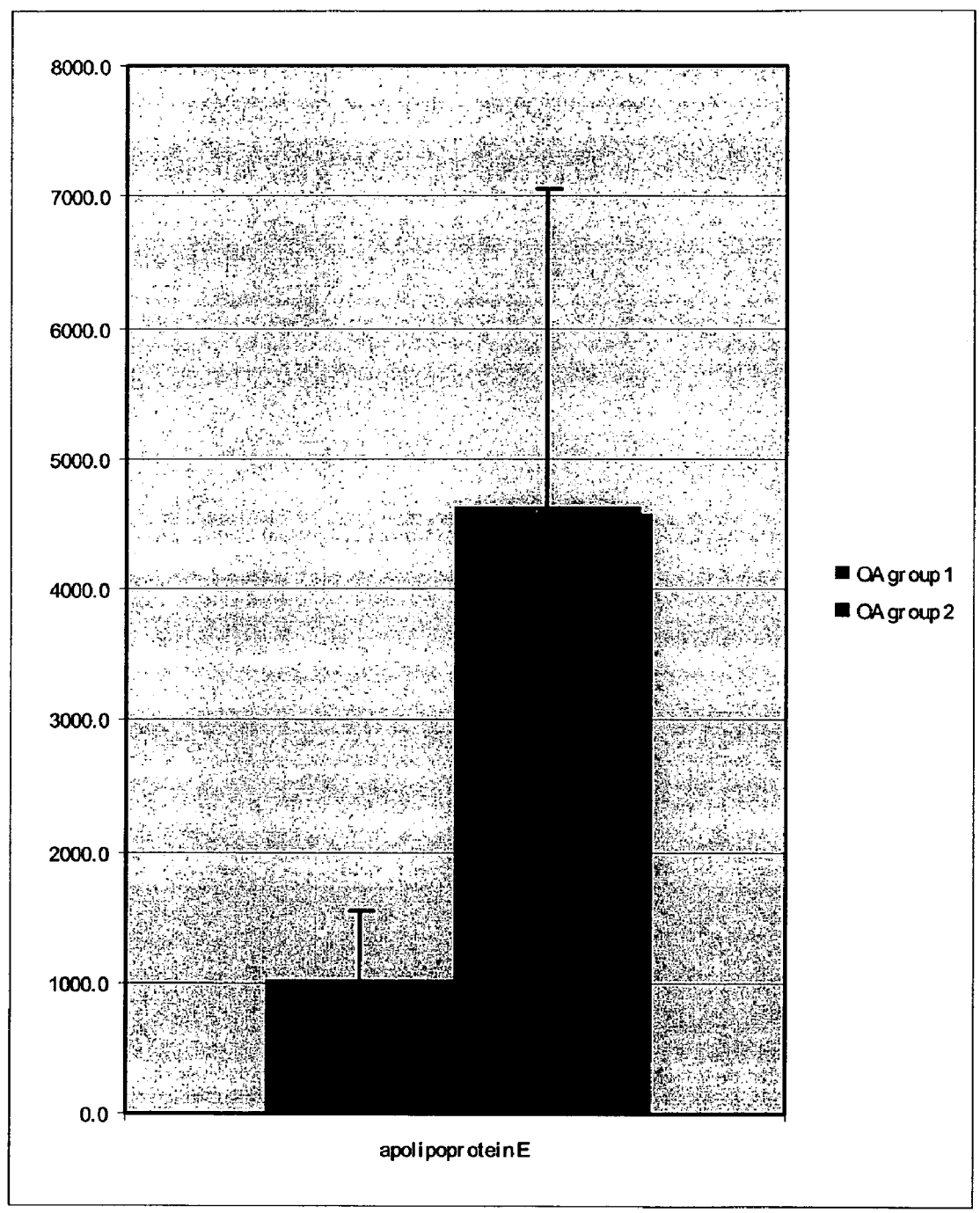
FIG. 16(A-L) is a set of graphs showing the differential expression of the 12 proteins listed in the table presented in FIG. 15 (see Example 3).
Figure 16B:
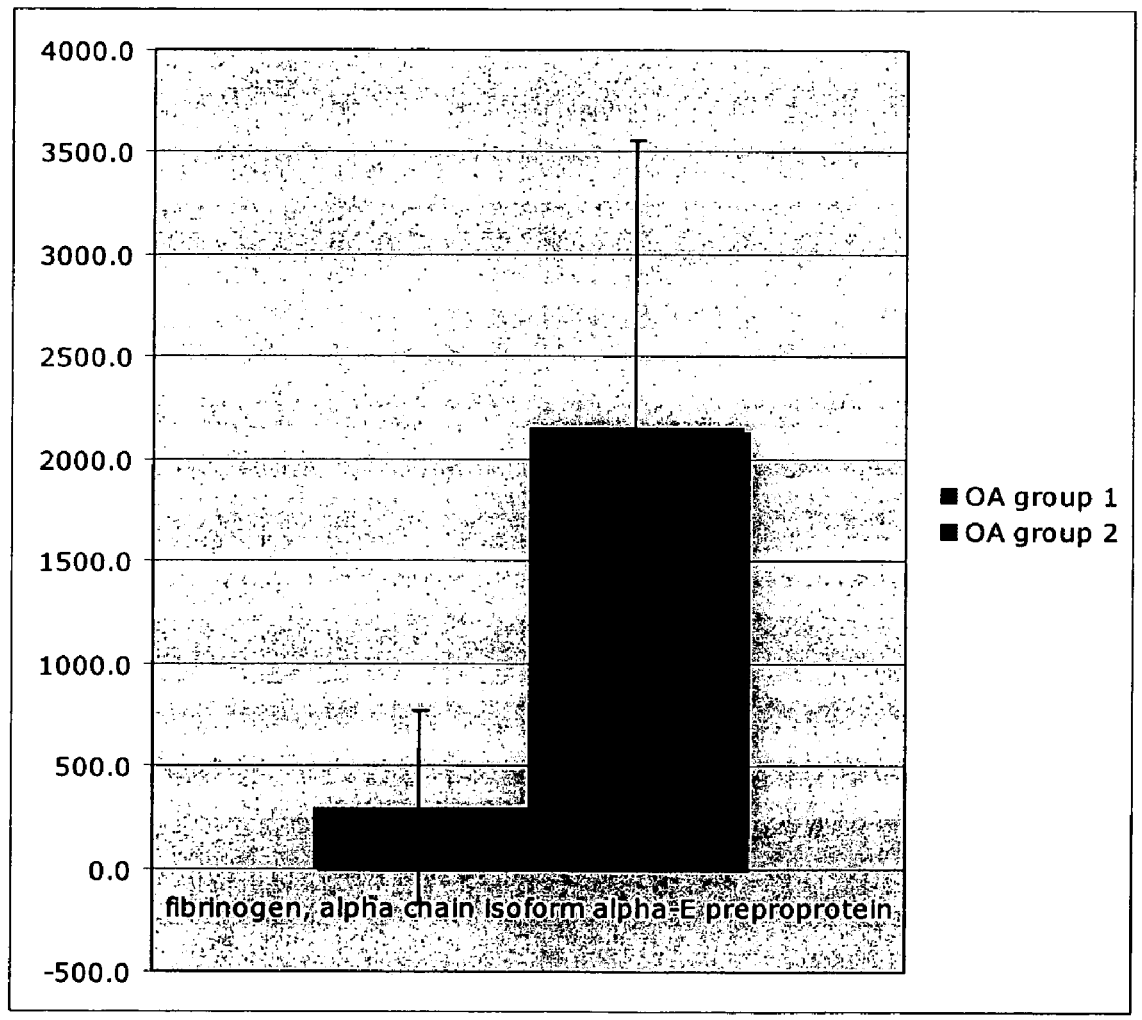
Figure 16C:
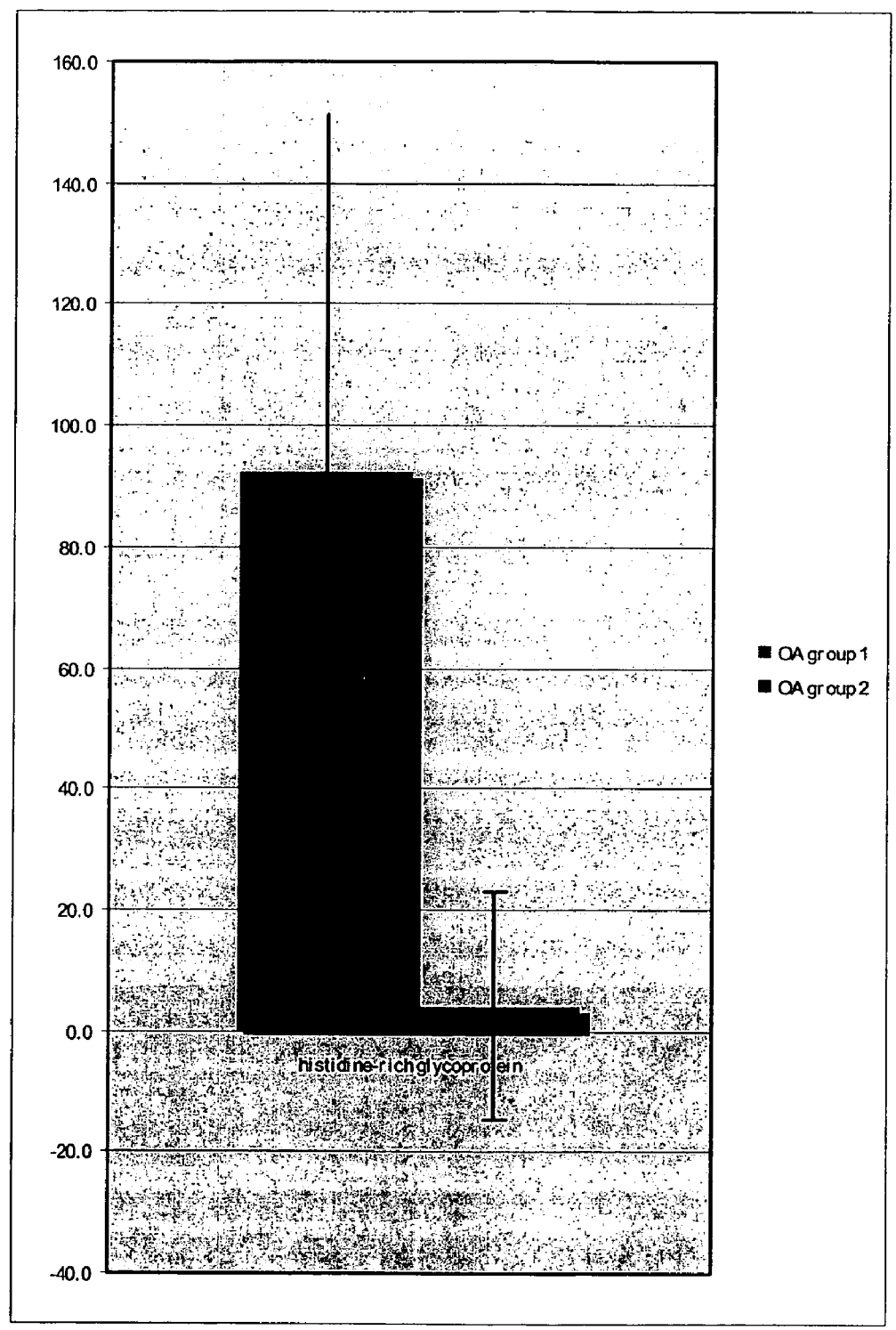
Figure 16D:
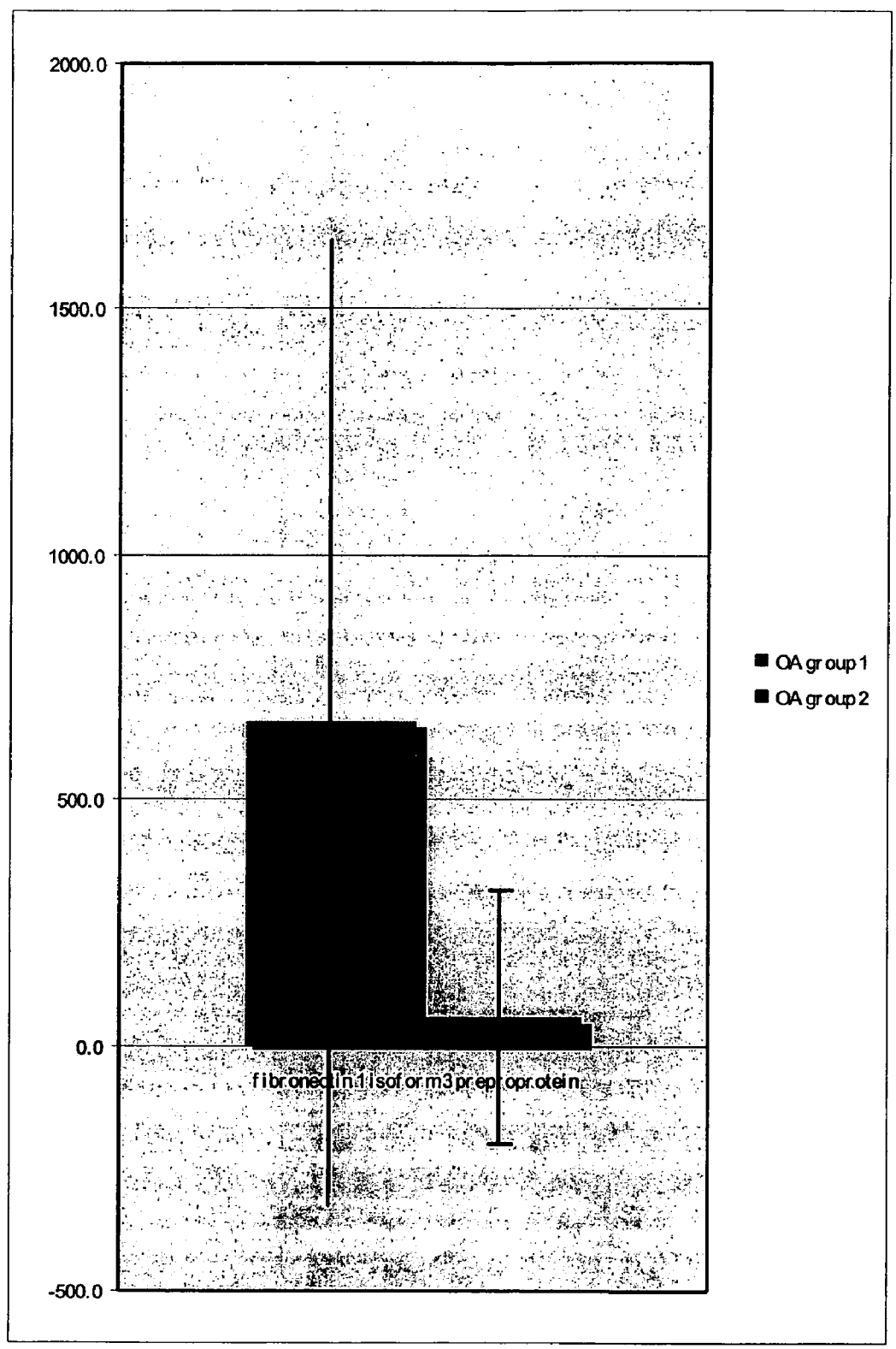
Figure 16E:
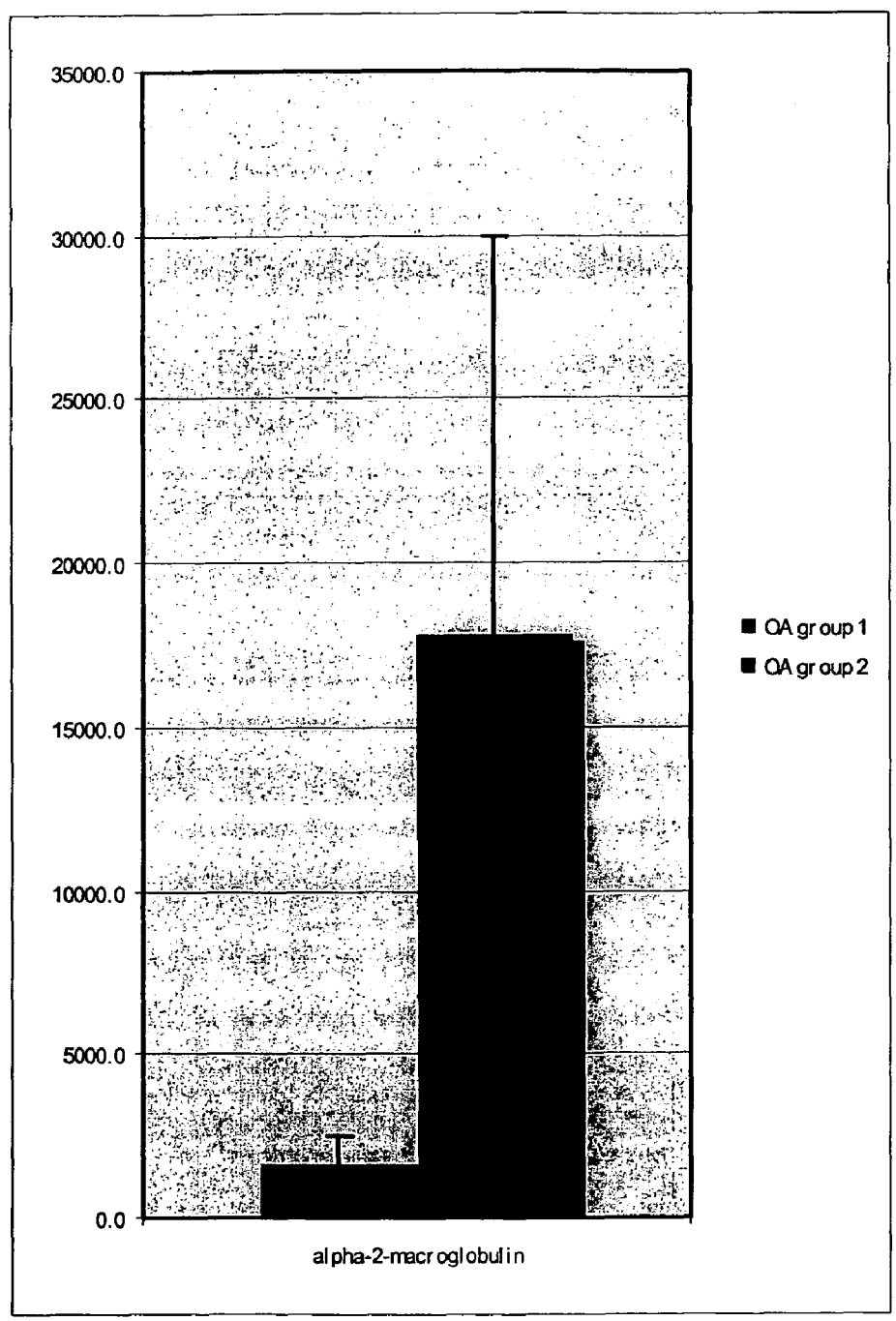
Figure 16F:
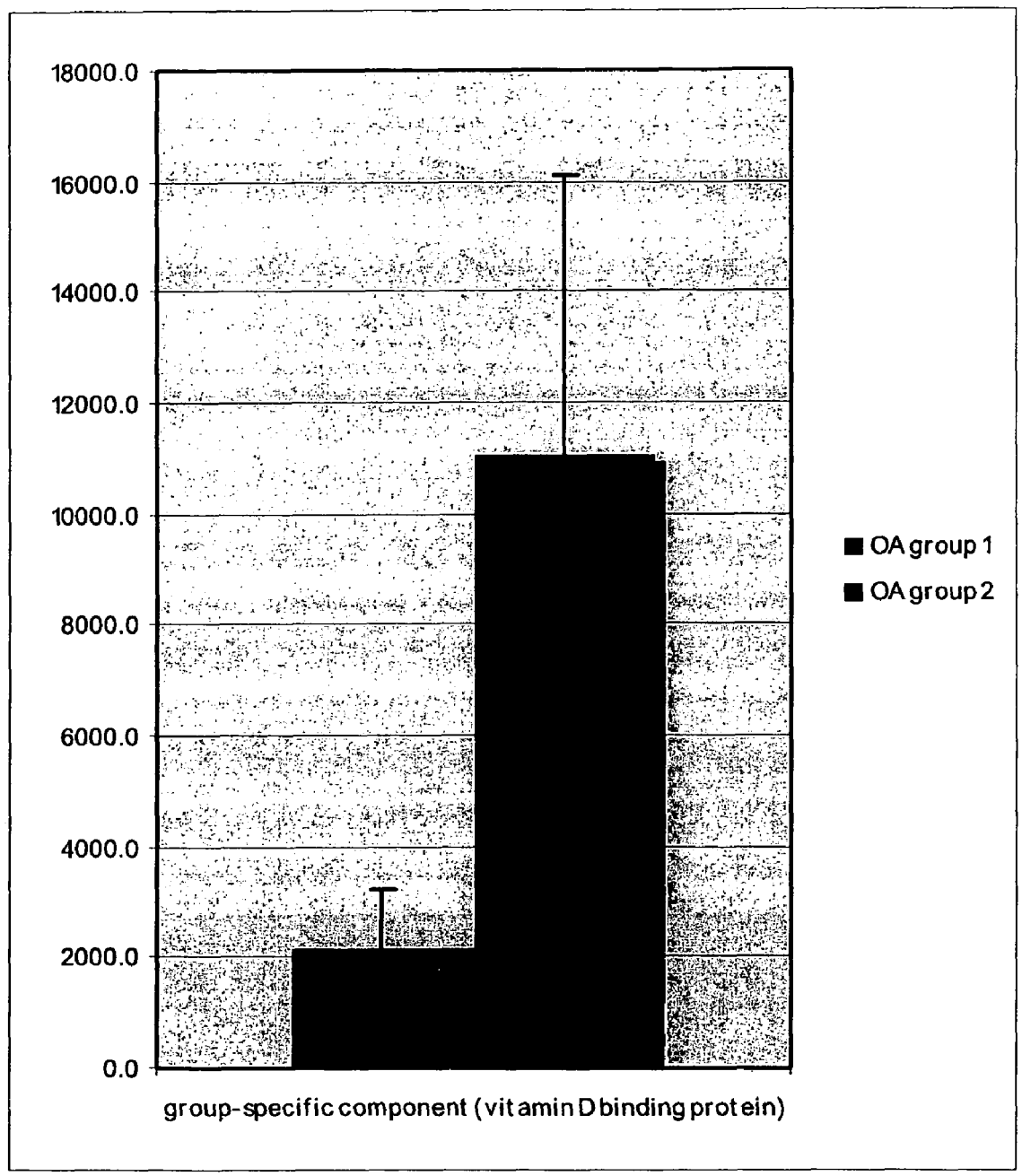
Figure 16G:
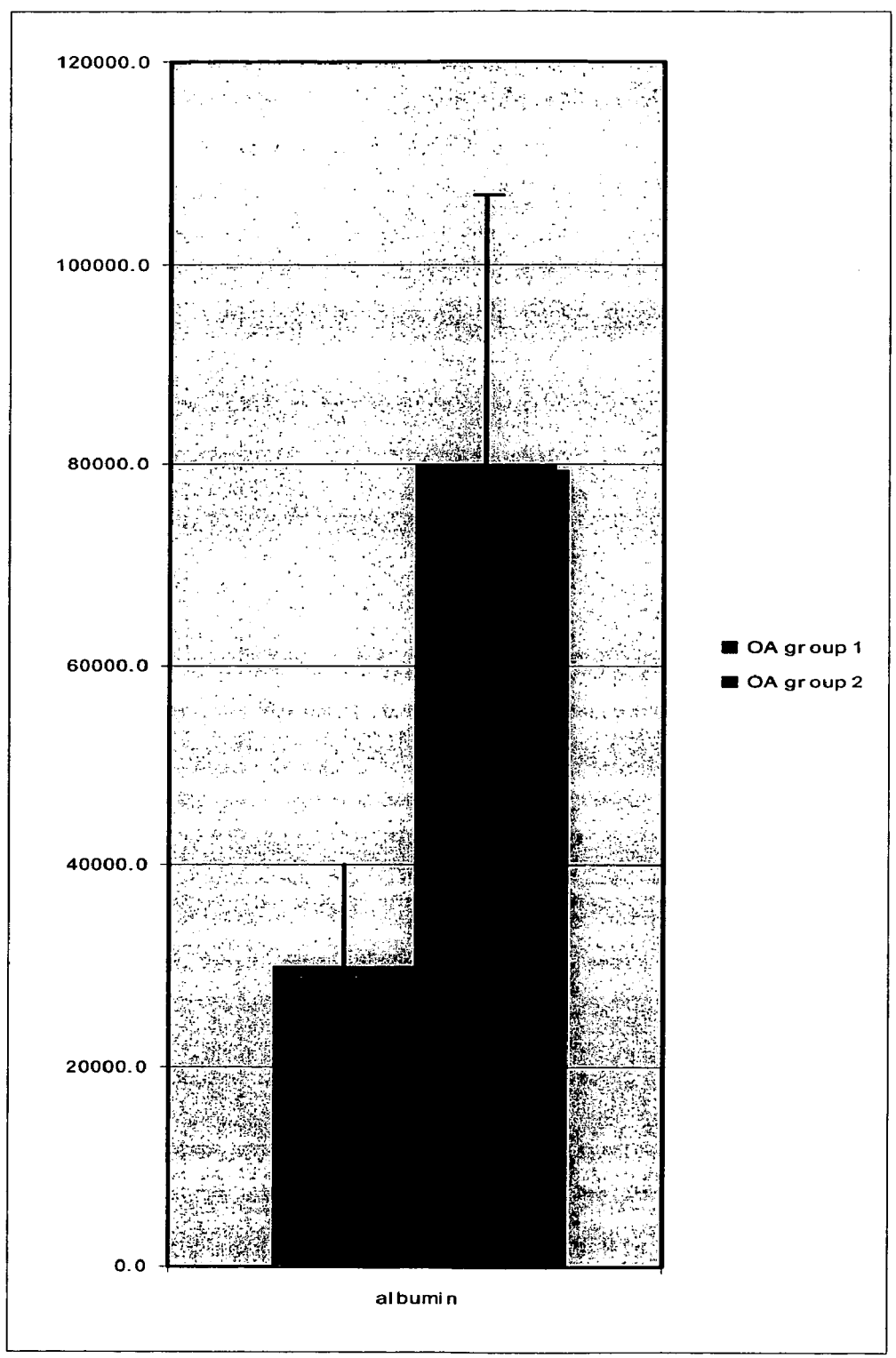
Figure 16H:
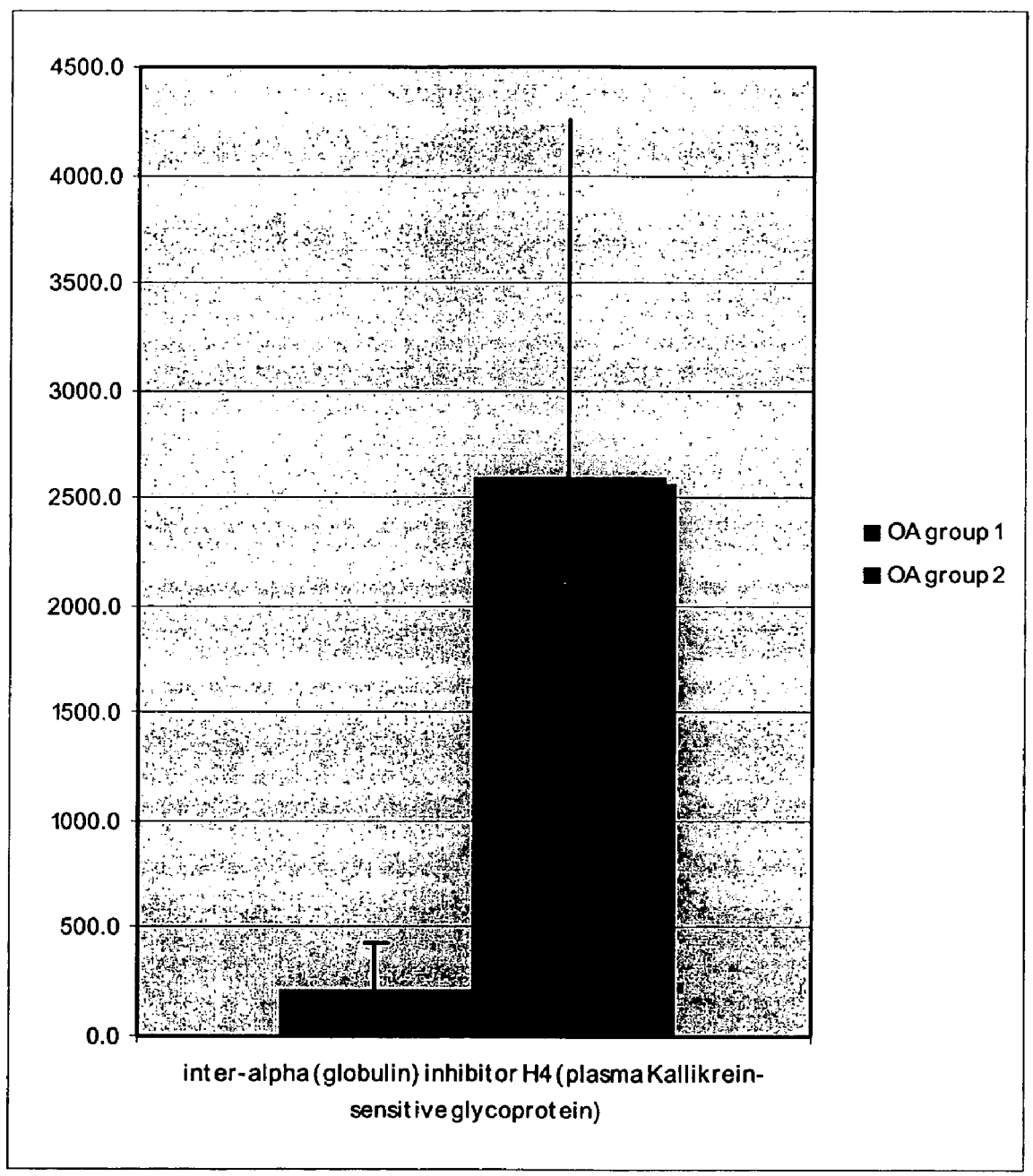
Figure 16I:
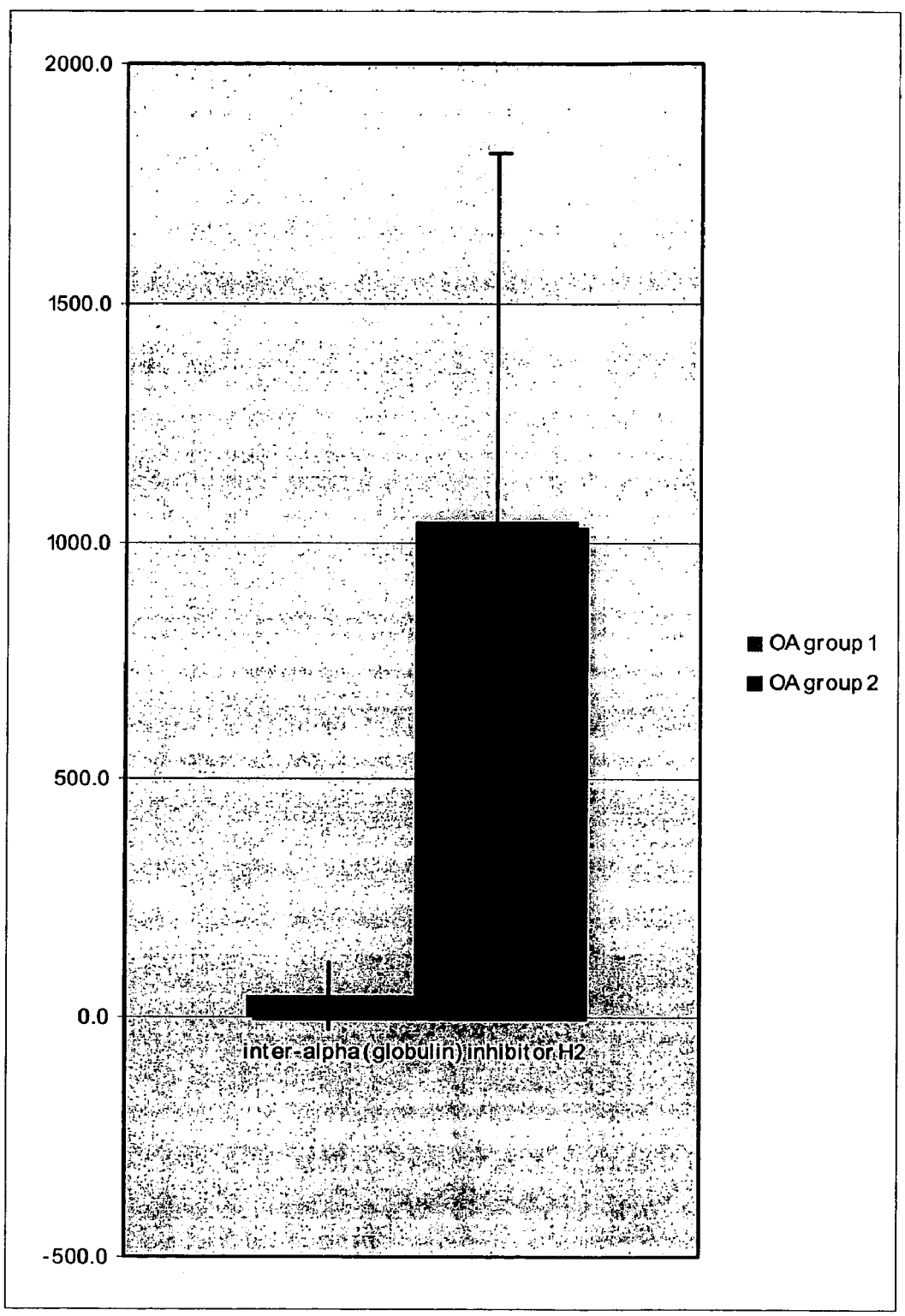
Figure 16J:
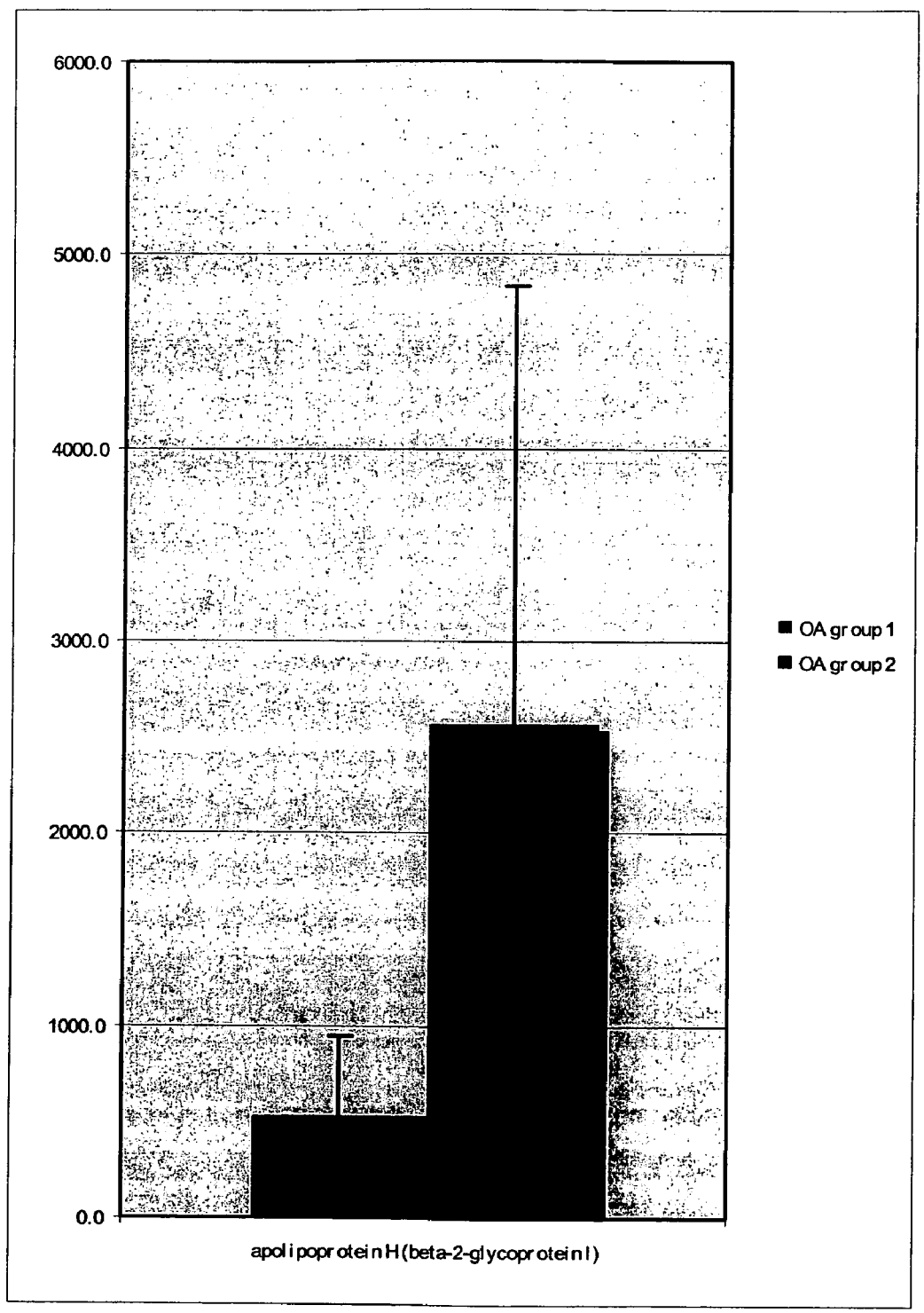
Figure 16K:
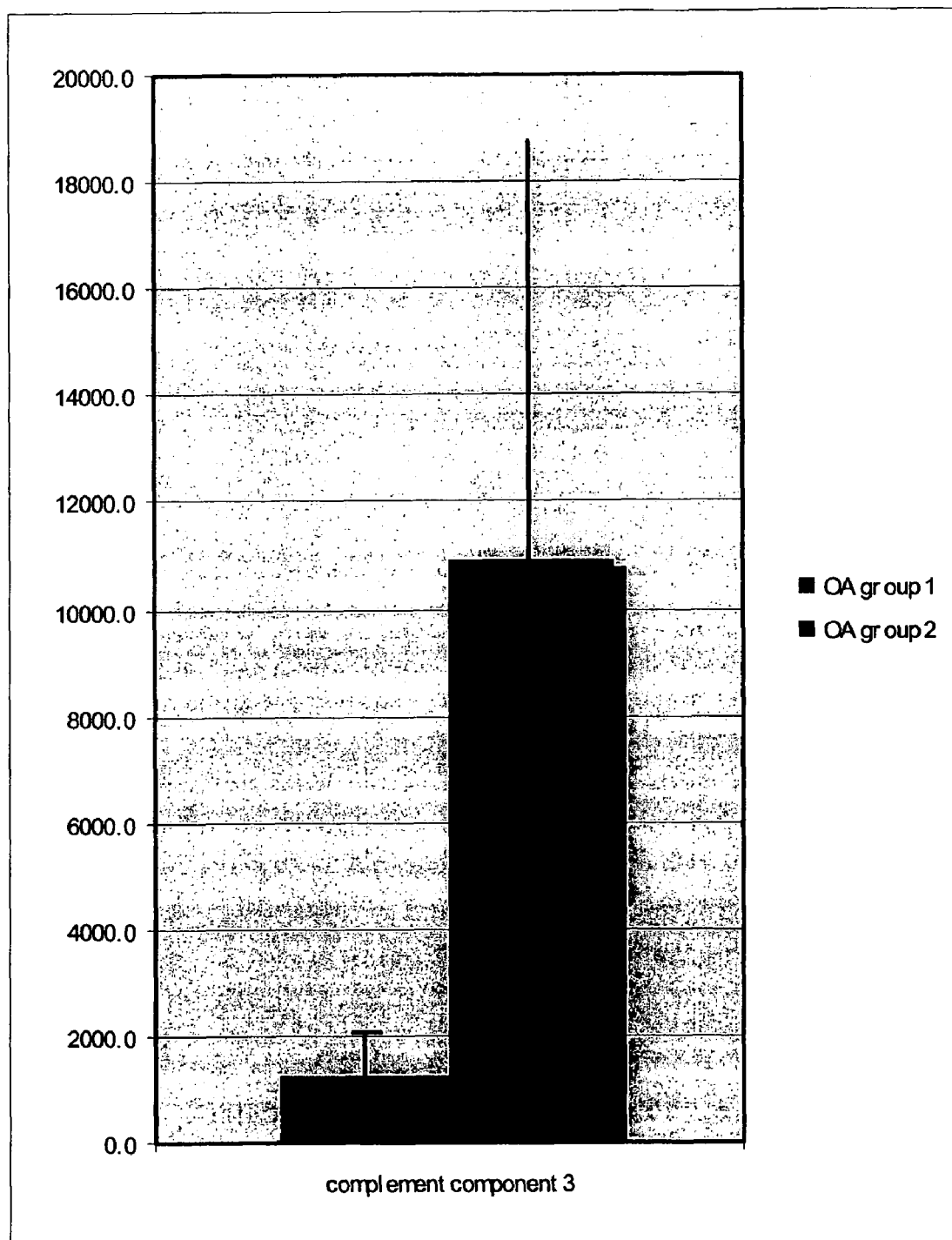
Figure 16L:
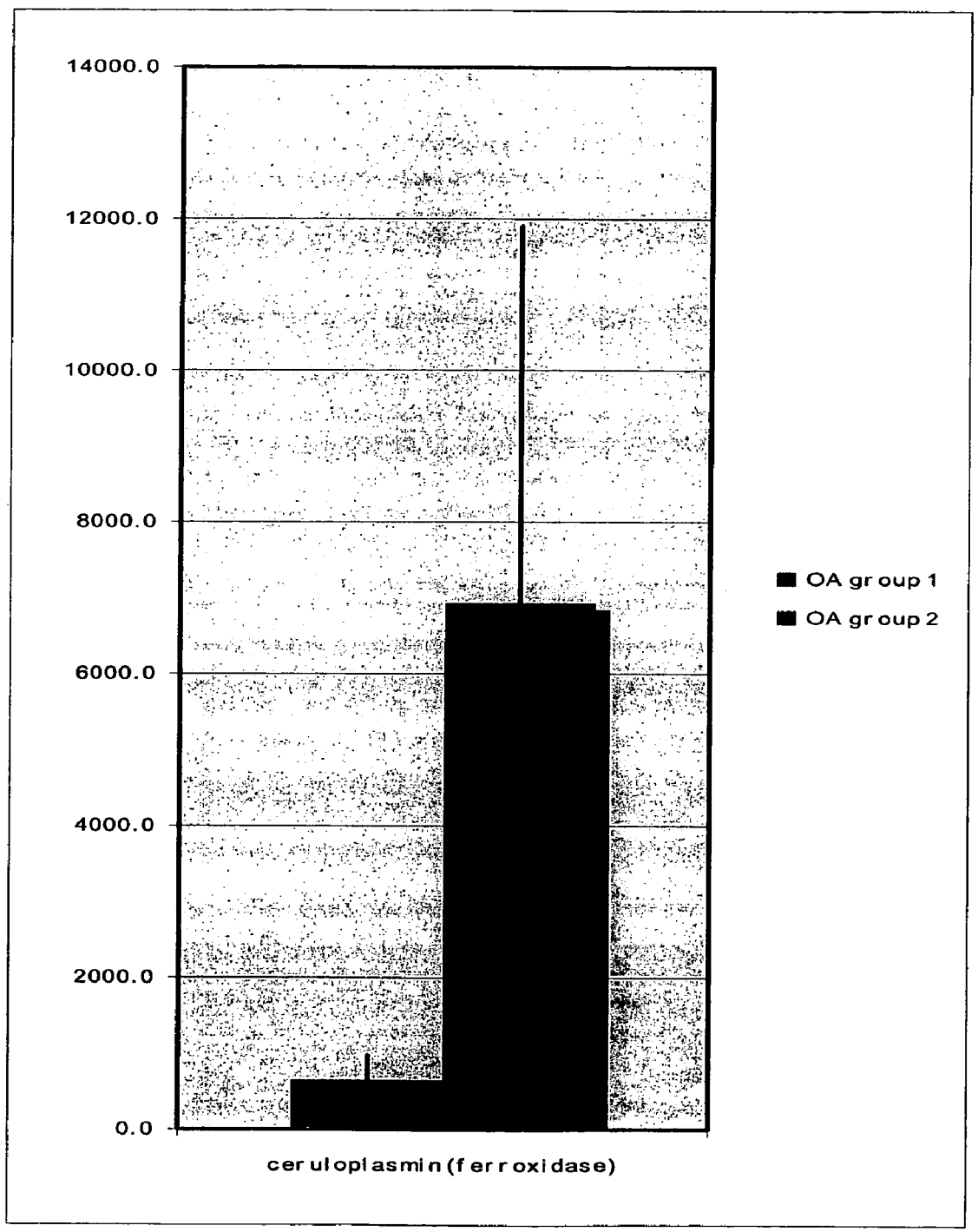

Supervised Wilcoxon's ranksum test returns unique proteins with significant differential abundance between the Healthy and OA group (p<0.00001) (see FIG. 4) The small p value used in this mathematical algorithm was chosen arbitrarily in order to reduce the number of candidate protein biomarkers identified to a manageable number appropriate for selective future study using more conventional techniques. These proteins are among the top 100 sample variation-contributing genes in PC1 and PC2 in the foregoing PCA. With the exception of 3 proteins, all were found to be significantly more abundant in the OA than Healthy group (see FIG. 12 and FIG. 14).

Sensitivity and Specificity of Biomarkers. For the proteins differentially expressed between any one of three comparisons above—Healthy versus EOA, Healthy versus LOA, or EOA versus LOA—the specificity and sensitivity of each protein (their differential expression) were computed (FIG. 13). The specificity and sensitivity calculation is illustrated for an example protein Q in the Healthy versus EOA comparison. Suppose that the median expression value of protein Q in the 20 Healthy and 20 EOA samples is $v_Q$, and that Q level is positively correlated with the Healthy class. A 2×2 contingency table is formed by counting the number of samples in each disease class (Healthy or EOA) and the expression level of protein Q in each sample relative to $v_Q$:

|  | Healthy (n = 20) | EOA (n = 20) |
|---|---|---|
| Q level ≧ $v_Q$ | # True Positive (TP) | # False Positive (FP) |

-continued

|  | Healthy (n = 20) | EOA (n = 20) |
|---|---|---|
| Q level < $v_Q$ | # False Negative (FN) | # True Negative (TN) |

Sensitivity was defined as (# TN)/(# TN+# FP), whereas specificity was defined as (# TP)/(# TP+# FN). The combined average sensitivity and specificity of these differentially expressed proteins are 84.58% and 84.58% respectively. However, using this panel of candidate protein biomarkers, a sensitivity and specificity of greater than 99% for identifying early and late OA, respectively, can be achieved (see FIG. 13).

Sensitivity and specificity of the subset of proteins identified with significantly different expression levels between subjects with OA and healthy controls (see FIG. 14) were also assessed. Examining sensitivity and specificity of individual proteins demonstrated that several of the proteins in this panel hold promise as potential biomarkers to distinguish health from OA. Indeed, the best sensitivity and specificity for proteins in this subset was noted for complement component 3, which displayed sensitivity and specificity of 90% and 85%, respectively.

Differentially Abundant Proteins in Discrete OA Subsets. Two apparent subsets of patients with OA were observed in the unsupervised PCA of the rank-normalized protein data. These two subpopulations did not seem to be segregated by age, gender, ethnicity, or number of medications taken. A supervised Wilcoxon Ranksum test to identify differential protein expression between these two OA subsets irrespective of the disease duration was performed. Using a highly significant P-value cut-off (P<0.00005), 12 proteins (see FIG. 15) were identified that demonstrate differential expression between these two OA subsets (see FIG. 16).

Discussion

The development of reliable biomarkers for OA would contribute significantly to progress in improving the treatment and understanding the mechanism of this disorder in at least three ways. First, the biomarkers may be used as a diagnostic in order to identify osteoarthritis in the early stages of disease. The clinical impact of using a biomarker in this capacity for any disease is related to the efficacy of existing therapeutics to cure or halt that disease once it is identified. At present, there are several pharmaceuticals used to treat OA and none of them have been convincingly shown to halt disease progression or reverse joint destruction with clinical trials. The role of OA biomarkers as diagnostics for early disease will grow increasingly valuable as the development of therapeutics that reverse joint destruction or prevent disease progression matures. A second and more immediate need for biomarkers that detect early OA is for their potential use as monitors for the efficacy of therapeutic interventions. One of the most expensive facets of drug development for OA is the cost and time associated with determining whether or not a particular candidate pharmaceutical therapy is effective and safe in patients. This difficulty stems from the absence of a sensitive and specific biomarker for OA that has been validated with clinical studies and whose level tracks with disease severity. The third important application for OA biomarkers relates to the potential to utilize them in order to define the clinical subclasses of this disorder. Recent studies and clinical experience has implicated the existence of phenotypically differing subclasses for non-inflammatory arthritis. However, very little is known about these phenotypes scientifically and there is currently no method to identify patients with the more aggressive subtypes of OA clinically during the early stages of the disease. The ability to distinguish subtypes within OA biochemically during early stages of disease might lead to valuable insight into the pathophysiology of this disorder and inform clinical decision making once effective therapeutics have been developed.

At present, there are no biomarkers in clinical use for the early detection of osteoarthritis. The present comparative proteomic analysis of synovial fluid from the knees of healthy subjects and patients with osteoarthritis resulted in the identification of differentially expressed protein biomarkers. Although no single biomarker possessed both high sensitivity and specificity, the panel of biomarkers as a group demonstrated a combined sensitivity and specificity of nearly 100%, respectively. To our knowledge, this study represents the first successful identification of sensitive and specific candidate biomarkers for osteoarthritis identified using proteomics analysis.

Biomarker discovery for OA and rheumatoid arthritis (RA) is an area of active research and progress. Several candidate biomarkers have been identified for osteoarthritis using various techniques. One of the most promising of these biomarkers is CTX-II, a marker for cartilage degradation. Investigators have shown that this biomarker has the ability to distinguish RA and OA from healthy controls (S. Chrisgau et al., Bone, 2001, 29: 209-215). Other studies have demonstrated the potential of this candidate biomarker to detect cartilage breakdown in the urine (M. Jung et al., Pathobiology, 2004, 71: 70-75). If this candidate biomarker quantitatively tracks with the severity of disease, as some studies have indicated (S. Chrisgau et al., Bone, 2001, 29: 209-215; P. Garnero et al., Ann. Rheum. Dis., 2001, 60: 619-626), it might useful as a monitor for the efficacy of therapeutics under development. CTX-II has been shown in one study to be predictive of radiological disease progression (M. Reigman et al., Arthritis Rheum., 2004, 50: 2471-2478). However, in order to truly transition from a candidate biomarker or measurement to a clinically useful biomarker, it is critical that the sensitivity, specificity and predictive values be determined in a large validated patient population.

Another protein of interest identified as a potential biomarker for OA and RA is cartilage oligomatrix protein (COMP) (C. S. Carlson et al., J. Orthop. Res., 2002, 20: 92-100; A. D. Recklies et al., Arthritis Rheum., 1998, 41: 997-1006; M. Sharif et al., Br. J. Rheumatol., 1995, 34: 306-310; M. Skoumal et al., Scand. J. Rheumatol., 2003, 32: 156-161). As with CTX-II, some investigators have reported that this candidate biomarker may have levels that follow disease progression in the serum and correlate with joint destruction radiographically (M. Sharif et al., Arthritis Rheum., 2004, 50: 2479-2488; V. Vilim et al., Arch. Biochem. Biophys., 1997, 341: 8-16). YLK-40 is another candidate biomarker with the reported ability to be found in the serum and synovial fluid of patients with end-stage OA and active RA. The evidence indicating that it is not found during early OA makes its candidacy as a potential biomarker for OA far less appealing (T. Conrozier et al., Ann. Rheum. Dis., 2000, 59: 828-231; S. Harvey et al., Scand. J. Rheumatol., 2000, 29: 391-393; J. S. Johansen et al., Br. J. Rheumatol., 1996, 35: 553-559; J. S. Johansen et al., Br. J. Rheumatol., 1993, 32: 949-955). The levels of another protein, 5D4, have reportedly been shown to decrease in the synovial fluid and serum of OA and RA patients (A. R. Poole et al., J. Clin. Invest., 1994, 94: 35-33; M. Sharif et al., Br. J. Rheumatol., 1996, 35: 951 957) although this date is confused with other investigators reporting elevated levels in OA patients (G. V. Campion et al., Arthritis Rheum., 1991, 34: 1254-1259; F. Mehraban et al., Arthritis Rheum., 1991, 34: 383-392). Aggrecan, a large molecule that aggregates with hyaluronan, has also been identified as a potential biomarker and is considered an indicator of cartilage formation (P. Garnero et al., Arthritis Rheum., 2000, 43: 953-968). Aggrecan 846 has been found in high concentrations within the synovial fluid and cartilage of OA patients (L. S. Lohmander et al., Arthritis Rheum., 1999, 42: 534-544; A. R. Poole et al., J. Clin. Invest., 1994, 94: 25-33; G. Rizkalla et al., J. Clin. Invest., 1992, 90: 2268-2277). The serum levels of aggrecan 846 have been reported to be at their highest levels during the latest stages of OA (A. R. Poole et al., J. Clin. Invest., 1994, 94: 25-33) whereas the implication from studies in RA patients is that these levels vary with the subtype of disease (Mansson et al., J. Clin. Invest., 1995, 1071-1077). Our preliminary data implicate aggrecan as a highly sensitive candidate biomarker for early and late OA with levels that are at their highest within synovial fluid in the healthy non-arthritic knee (see FIG. 13) Several cartilage breakdown products and COMP were identified from our samples on the mass spectrometer although they did not retain predictive value, as represented by sensitivity and specificity, once the statistical and mathematical analysis of our data was performed.

The absence of cystatin A, an extracellular cysteine protease inhibitor, in the osteoarthritic samples from the present study confirms results from previous studies that have linked the downregulation of cystatins to the development of osteoarthritis (M. Abrahamson et al., Biochem. Soc. Symp., 2003, 70: 179-199; B. Lenarcic et al., Biol. Chem. Hoppe Seyler, 1988, 369 Suppl: 257-261; J. Martel-Pelletier et al., J. Orthop. Res., 1990, 8: 336-344; V. Turk and W. Bode, FEBS Lett., 1991, 285: 213-219). The finding also provides support to studies suggesting an important role for cathepsins in the development of early osteoarthritis (R. A. Dodds et al., Arthritis Rheum., 1999, 42: 1588-1593; D. Gabrijelcic et al., J. Clin. Chem. Clin. Biochem., 1990, 28: 149-153; W. S. Hou et al., Arthritis Rheum., 2002, 46: 663-674; G. M. Keyszer et al., Arthritis Rheum., 1995, 38: 976-984; Y. T. Konttinen et al., Arthritis Rheum., 2002, 46: 953-960; J. P Morko et al., Ann. Rheum. Dis., 2004, 63: 649-655). This supposition is further supported by the functional capacity of cathepsin to degrade aggrecan-1. Absence of cystatin protease inhibitors in OA synovial fluid may allow the degradation of aggrecan-1 and other cartilage components and thereby contribute to the pathogenesis of OA. The precise interplay between cathepsins, cystatins and aggrecans in osteoarthritis remains a subject for further investigation.

Comparison of protein abundance between healthy and OA subjects in the present study has demonstrated 18 highly significant (P<0.000001) and a large number of less statistically significant differentially expressed proteins, many of which have previously been identified by other investigators. Of these 18 proteins, 3 display decreased expression levels in OA subjects while 15 are more abundant in OA than healthy subjects (see FIGS. 12 and 14). This differential profile provides insight into the pathophysiology of OA. Increased abundance of aggrecan and cystatin-A in synovial fluid from healthy subjects is consistent with the current concept that the loss of cartilage observed in OA results from proteolytic destruction of extracellular matrix (M. A. Pratta et al., Osteoarthritis Cartilage, 2006, 14: 702-713; A. Struglics et al., Osteoarthritis Cartilage, 2006, 14: 101-113; A. R. Poole et al., J. Clin. Invest., 1994, 94: 25-33; L. S. Lohmander et al., 1999, 42: 534-544; G. Rizkalla et al., J. Clin. Invest., 1992, 90: 2268-2277; M. G. Chambers et al., Osteoarthritis Cartilage, 2002, 10: 51-61; J. P. Morko et al., Ann. Rheum. Dis., 2004, 63: 649-655; D. Gabrijelcic et al., J. Clin. Chem. Clin. Biochem., 1990, 28: 149-153; B. Lenarcic et al., Biol., Chem. Hoppe Seyler, 1988, 369 (Suppl.): 257-261; J. Martel-Pelletier et al., J. Orthop. Res., 1990, 8: 336-344). It is particularly interesting that cystatin-A, an inhibitor of cystein proteases (e.g., cathepsins), is elevated in healthy synovial fluid while serine protease inhibitors, abundant in health and disease in our analyses and implicated in the pathogenesis of OA (1 J. P. Morko et al., Ann. Rheum. Dis., 2004, 63: 649-655; M. Abrahamson et al., Biochem. Soc. Symp., 2003, 70: 179-199; W. S. Hou et al., Arthritis Rheum., 2002, 46: 663-674; R. A. Dodds et al., Arthritis Rheum., 1999, 42: 1588-1593), are not among the panel of highly statistically significantly differentially expressed proteins. This observation provides strong rationale for continued focus in the contribution of both classes of protease inhibitors to OA pathogenesis.

Dermcidin, the third abundant synovial fluid protein demonstrating increased expression in normal vs. OA subjects, is a novel antimicrobial peptide previously identified in human sweat (B. Schittek et al., Nat. Immunol., 2001, 2: 1133-1137). Dermcidin peptides derive from post-translational and post-secretion processing by a series of proteases present in sweat glands (B. Schittek et al., Nat. Immunol., 2001, 2: 1133-1137; S. Rieg et al., J. Invest. Dermatol., 2006, 126: 354-365). To our knowledge, this is the first report identifying dermcidin expression in synovial fluid; the role of this protein in healthy joint physiology and the pathophysiologic consequences of decreased expression in OA require further investigation.

The analysis of the data from this study has two other potentially important implications with regards to our understanding of OA pathophysiology. First, principle component analysis using peak area revealed two distinct populations within the OA cohorts. These distinct groups were present both in early and late OA. Since the inclusion criteria for the OA cohorts were designed to identify patients with primary idiopathic osteoarthritis, this observation suggests that 'primary' osteoarthritis is, in fact, a heterogeneous disorder. Our analysis of the medical history and medication records for each patient in our study was not able to identify any statistically significant relationship in the variation for protein expression resulting from medications, diseases or demographics. Therefore, these candidate biomarkers may be useful in selecting specific subclasses of OA amongst patients for future study. Second, the candidate biomarker profile for OA derived from this study suggests that the pathomechanism of osteoarthritis does not change significantly, on a molecular level, throughout the course of disease. If early and late osteoarthritis were represented by a progression of molecular changes, we would expect to see a variance in the protein expression profile between these two disease groups with disease progression. Rather, the pathophysiology of OA may resemble a 'wrecking-ball' phenomenon. That is, a continuous and unchanging cycle of pathophysiologic changes within arthritic joints continues over a period of many months to years gradually resulting in the destruction of articular cartilage resulting in phenotypically late OA.

Intriguingly, the unsupervised analyses in the present study have identified 2 clearly distinct subpopulations of patients with OA that are independent of disease duration. Supervised (Wilcoxon rank-sum) analysis identified 12 protein species differentially populating the synovial fluid of these OA subjects. It is noteworthy that proteins present in blood comprise the entire cohort of proteins that contribute to identification of these OA subpopulations. This observation could result from differences in vascular permeability as a distinguishing pathophysiologic feature of a disease subject in patients with OA. However, most of these proteins have been identified more recently as products of the cells within joint tissue: chondrocytes and synoviocytes (C. Ruiz-Romero et al., Proteomics, 2005, 5: 3048-3059; C. Ruiz-Romero et al., Osteoarthritis Cartilage, 2006, 14: 507-518). Thus, the differences observed could also reflect differences resulting from OA joint physiology. Unfortunately, the design of this study precludes examination of the phenotype differences in these subgroups. Utilizing these 12 proteins in future expanded longitudinal cohorts of OA subjects will further clarify both the presence of disease phenotype subsets and the utility of quantifying these proteins in synovial fluid as a method of identifying OA sub-phenotypes for prognostic and therapeutic purposes.

Although one of the primary objectives of the present study was examination of differential protein expression of abundant synovial fluid proteins between healthy and OA subjects, the analysis also provided a wealth of information about the abundant protein composition of synovial fluid in health. Many proteins identified have been implicated in pathways thought to contribute to the physiologic homeostasis of cartilage, synovial tissue and synovial fluid. These proteins are considered below in the context of the pathways with which they have previously been associated in order to provide a synopsis of their potential biologic significance.

Serine Protease Inhibitors. Numerous serine protease inhibitors have been identified in the synovial fluid of both healthy and diseased patients. The abundance and large number of species of serine proteinase inhibitors is consistent with the importance of the diverse and highly regulated functions of serine proteinases in joint function. Included among the host of physiologic processes in diarthrodial joints regulated by these species are regulation of MMP's, aggrecanase, plasmin, tissue mitogens and angiogenesis activity as well as inhibition of inflammatory leukocyte proteases such as neutrophil elastase and regulation of fibroblast mitogen binding to extracellular matrix. Numerous lines of evidence demonstrate that synovial lining and cartilage extracellular matrix undergo active remodeling with joint homeostasis resulting from a delicate balance between matrix degradation, matrix synthesis and matrix assembly. The importance of this remodeling has been underscored by oncology trials of MMP inhibitors whose side effects included a progressive polyarthritis with joint pain and stiffness. Since the regulation and biologic function for a number of these serine proteinase inhibitors remains incompletely defined, the present analyses provide further rational for their continued study.

Inflammatory Cascades and Response to Oxidative Stress. Oxidative damage and activation of MAP kinases have been reported to be involved in the pathogenesis of OA; the present studies identify proteins implicated in these pathways as high abundance species in synovial fluid. S100 activates the receptor for advanced glycation end products (RAGE) (M. W. Hofmann et al., Cell, 1999, 97: 889-901; J. V. Valencia et al., Diabetes, 2004, 53: 743-751). Among the RAGE stimulated MAP kinase downstream signaling cascades is the increased activity of NF-kB which results in increased expression of MMPs and inflammatory mediators. Afamin has recently been identified as a novel Vit E binding protein (L. Jerkovic et al., J. Proteome Res., 2005, 4: 889-999). Vit E provides protection from oxidative damage by scavenging reactive oxygen and nitrogen species (R. Ricciarelli et al., Faseb J., 2001, 15: 2314-2325). Clusterin is produced in numerous tissues during tissue injury or in disease states, and has also been shown to be produced by normal and arthritic chondrocytes (J. R. Connor et al., Osteoarthritis Cartilage, 2001, 9: 727-737). It has numerous proposed functions including modulation of apoptosis by inhibition of Bax. In situ hybridization demonstrates upregulation of clusterin mRNA after exposure of chondrocytes to oxidative stress and may represent another pathway by which chondrocytes protect themselves from reactive oxygen and nitrogen species. Paraoxonase 1 is another antioxidant protein whose activity is likely to mirror those of the other antioxidants identified in this study. The presence of high concentrations of these species in healthy synovial fluid suggests that protection from oxidative stress is of particular importance in the avascular cartilage and highly specialized tissue of the joint lining.

The kallikrein-kinin system has been proposed to play a significant role in the inflammatory processes underlying OA (K. Worthy et al., Int. J. Exp. Pathol., 1990, 71: 587-601; K. D. Bhoola et al., Br. J. Rheumatol., 1992, 31: 509-518). Kallikrein cleaves high molecular weight kininogen to yield bradykinin, a potent β2 agonist on endothelial cells resulting in the release of prostacyclin and nitric oxide as well as increased vascular permeability via opening endothelial cell tight junctions and relaxing smooth muscles. Two elements of this systems have been identified here, kininogen-1 and N-carboxypeptidase, a zinc metalloprotease that degrades bradykinin and anaphylactic peptides of the complement system (I. A. Sheikh and A. P. Kaplan, Arthritis Rheum., 1987, 30: 138-145). These observations are congruent with previous work that has shown that synovial fluid contains all of the components to generate kinins (A. P. Bond et al., Immunopharmacology, 1997, 36: 209-216). It is impossible that disequilibrium between the rate of formation and breakdown of kinins resulting in the inflammation, joint pain and swelling seen in patients with arthritis.

The present analyses have also identified members of the potently pro-inflammatory complement cascade including components C1, C3, C4, C6 and C8 as well as complement inhibitory proteins factors H and I. Although blood (via ultrafiltration) could deliver complement found in synovial fluid, numerous groups have demonstrated that complement component production by synovial tissue cells (E. Neumann et al., Arthritis Rheum., 2002, 46: 934-945; S. Ruddy and H. R. Colten, New Engl. J. Med., 1974, 290: 1284-1288; Y. Katz and R. C. Strunk, Arthritis Rheum., 1988, 31: 1365-1370; G. S. Firestein et al., Arthritis Rheum., 1991, 34: 1094-1105; S. Breitner et al., Arthritis Rheum., 1995, 38: 492-498). These observations raise the possibility that synovial tissue generates these abundant protein species locally. Functionally, the complement cascade is implicated in innate immunologic defense of the avascular cartilage and synovial fluid as wall as in the pathophysiology of both OA and RA (E. Neumann et al., Arthritis Rheum., 2002, 46: 934-945; G. S. Firestein et al., Arthritis Rheum., 1991, 34: 1094-1105; U. Olmez et al., Scand. J. Rheumatol., 1991, 20: 183-189; C. D. Collard et al., Mol. Immunol., 1999, 36: 941-948; M. Doherty et al., Ann. Rheum. Dis., 1988, 47: 190-197; A. Corvetta et al., Clin. Exp. Rheumtol., 1992, 10: 433-438; T. Collins et al., Clin. Diagn. Lab. Immunol., 1996, 3: 5-9).

Extracellular Matrix and Cartilage Metabolism. Numerous extracellular matrix and cartilage metabolism proteins also comprise a significant fraction of abundant soluble proteins in synovial fluid. Collagen type VI, a minor species found in hyaline cartilage, cartilage oligomatrix protein (COMP), a non-collagenous cartilage glycoprotein and lumican, a member of the small leucine-rich proteoglycans (SLRPs) that bind collagen and cartilage intermediate layer protein (CILP) are all constituents of either cartilage or synovial tissue extracellular matrix (D. R. Eyre et al., J. Rheumatol., 1987, 14 (Spec. No): 25-27; B. Swoboda et al., J. Orthop. Res., 1998, 16: 96-99; L. S. Lohmander et al., Ann. Rheum. Dis., 1994, 53: 8-13; T. Saxne et al., Arthritis Rheum., 1993, 36: 20-25; E. Hedbom et al., J. Biol. Chem., 1992, 267: 6132-6136; C. B. Knudson et al., Semin. Cell Dev. Biol., 2001, 12: 69-78).

Their presence in high abundance within healthy synovial fluid underscores the highly active tissue repair and remodeling that is present in joint tissues. Other proteins associated with cartilage physiology that are present in high abundance in synovial fluid include proteoglycan 4 (PRG4) a lubricating glycoprotein homologous to lubricin and insulin-like growth factor binding proteins (IGFBPs) regulate the activity of the anabolic protein insulin-like growth factor I (IGF-I). It is noteworthy that IGF-I is one of the most important trophic factors for cartilage (G. D. Jay et al., Orthop. Res., 2001, 19: 677-687; P. Lorenzo et al., J. Biol. Chem., 1998, 273: 23464-23468; P. Lorenzo et al., J. Biol. Chem., 1998, 273L 23469-23475).

Interestingly, the present studies also identified a number of protein species not previously appreciated as abundant components of synovial fluid. Demonstrating expression of hemopexin, tetranectin, inter-α-trypsin inhibitor, histidine-rich glycoprotein, gelsolin, vimentin and numerous other protein species suggests contribution by these classes of protein to synovial fluid function. Further analyses of these species promise to provide novel insights into synovial fluid physiology in health and disease.

Finally, the results from this study also hold promise for use of differentially expressed abundant protein species in synovial fluid as biomarkers for diagnosis and monitoring therapeutic responses in OA. The ability of these candidate biomarkers to adequately distinguish OA patients from normal subjects will require validation in larger independent cohorts of patients.

While the present studies identify a large number of abundant proteins, there are a number of anticipated proteins absent from the present list. A striking example is lubricin, a protein whose lubricating properties are critical for both cartilage and synovial lining physiology (D. K. Rhee et al., J. Clin. Invest., 2005, 115: 622-631). Lubricin is present at 200 μg/mL in healthy synovial fluid (D. K. Rhee et al., J. Biol. Chem., 2005, 280: 31325-31332; D. K. Rhee et al., J. Clin. Invest., 2005, 115: 622-631). Absence of this protein in the present studies suggests that the level of sensitivity is less than 200 μg/mL, or could represent a technical limitation of the present approach. Lubricin has a Mr of >200 KDa and penetration of large proteins into the primary PAGE separation technique may limit sensitivity (D. K. Rhee et al., J. Clin. Invest., 2005, 115: 622-631). The present results must be interpreted in light of both of these technical limitations.

The articular cartilage matrix undergoes many changes to its structure, molecular configuration and mechanical properties with age including surface fibrillations, increased collage cross-linking, and alterations in proteoglycan structure. Prevalence studies have shown that after the age of 40 years the incidence of OA increases with every passing decade. In an attempt to minimize confounding variables with regards to the analysis of synovial fluid from patients with sub-clinical and pre-radiographic OA, the control group for this study was chosen from volunteers that were under the age of 40 years. Implicit in this design was lack of age matched controls as most patients with early and late OA are greater than 40 years of age. In addition, the early OA cohort did not control for patients with inner-third meniscal tears that did not have OA. Finally, the disease specific performance of these candidate biomarkers was not studied nor were these biomarkers tested against patient populations with varying age, gender, race or disease etiology (traumatic, infectious, etc.).

The present method of obtaining synovial fluid necessitated penetration of the articular space using 18 gauge needle, a process with obligatory passage through skin and subcutaneous tissue. The method identified skin specific keratin species within the abundant proteins in synovial fluid. Knowing these species could only derive from skin, these proteins were removed from the subsequent analyses. The extent of contamination by other skin constituents in our analyses remains undefined.

OTHER EMBODIMENTS

Other embodiments of the invention will be apparent to those skilled in the art from a consideration of the specification or practice of the invention disclosed herein. It is intended that the specification and examples be considered as exemplary only, with the true scope of the invention being indicated by the following claims.

What is claimed is:

1. A method for identifying subtype II osteoarthritis suffered by a human subject, said method comprising the steps of:
providing synovial fluid obtained from the subject;
determining, in the synovial fluid, the levels of a first subset of polypeptides comprising alpha-2-macroglobulin, ceruloplasmin (ferroxidase), albumin, group-specific component (vitamin D binding protein), inter-alpha (globulin) inhibitor H4 (plasma Kallikrein-sensitive glycoprotein), complement component 3, apolipoprotein E, fibrinogen alpha chain isoform alpha-E preproprotein, apolipoprotein H (beta-2-glycoprotein I), and inter-alpha (globulin) inhibitor H2 to obtain a first test polypeptide expression profile, or the levels of a second subset of polypeptides comprising fibronectin I isoform 3 preproprotein and histidine-rich glycoprotein to obtain a second test polypeptide expression profile; and
comparing the first test polypeptide expression profile or the second test polypeptide expression profile to a control polypeptide expression profile, wherein the control polypeptide expression profile is a subtype I osteoarthritis expression profile comprising the levels of all the polypeptides of the first subset and the second subset in the determining step, and wherein an increase in the levels of polypeptides of the first subset of polypeptides in the subject, or a decrease in the levels of the polypeptides of the second subset identifies the subject as having subtype II osteoarthritis.

2. The method of claim 1 further comprising a step of:
selecting a therapy for the subject based on the osteoarthritis diagnosis.

3. A method for identifying subtype I osteoarthritis suffered by a human subject, said method comprising the steps of:
providing synovial fluid obtained from the subject;
determining, in the synovial fluid, the levels of a first subset of polypeptides comprising alpha-2-macroglobulin, ceruloplasmin (ferroxidase), albumin, group-specific component (vitamin D binding protein), inter-alpha (globulin) inhibitor H4 (plasma Kallikrein-sensitive glycoprotein), complement component 3, apolipoprotein E, fibrinogen alpha chain isoform alpha-E preproprotein, apolipoprotein H (beta-2-glycoprotein I), and inter-alpha (globulin) inhibitor H2 to obtain a first test polypeptide expression profile, or the levels of a second subset of polypeptides comprising fibronectin I isoform 3 preproprotein and histidine-rich glycoprotein to obtain a second test polypeptide expression profile; and
comparing the first test polypeptide expression profile or the second test polypeptide expression profile to a control polypeptide expression profile, wherein the control polypeptide expression profile is a subtype II osteoarthritis expression profile comprising the levels of all the polypeptides of the first subset and the second subset in the determining step, and wherein a decrease in the levels of polypeptides of the first subset of polypeptides in the subject, or an increase in the levels of the polypeptides of the second subset identifies the subject as having subtype I osteoarthritis.

4. The method of claim 3 further comprising a step of:
selecting a therapy for the subject based on the osteoarthritis diagnosis.

* * * * *